(12) United States Patent
Zhou et al.

(10) Patent No.: US 11,964,160 B2
(45) Date of Patent: Apr. 23, 2024

(54) METHOD AND APPARATUS FOR DELIVERING BUNDLE BRANCH PACING

(71) Applicant: Medtronic, Inc., Minneapolis, MN (US)

(72) Inventors: Xiaohong Zhou, Woodbury, MN (US); Wade M. Demmer, Coon Rapids, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 315 days.

(21) Appl. No.: 17/370,303

(22) Filed: Jul. 8, 2021

(65) Prior Publication Data
US 2022/0023640 A1  Jan. 27, 2022

Related U.S. Application Data

(60) Provisional application No. 63/112,980, filed on Nov. 12, 2020, provisional application No. 63/057,263, filed on Jul. 27, 2020.

(51) Int. Cl.
A61N 1/37 (2006.01)
(52) U.S. Cl.
CPC ........... *A61N 1/371* (2013.01); *A61N 1/3702* (2013.01)
(58) Field of Classification Search
None
See application file for complete search history.

(56) References Cited

U.S. PATENT DOCUMENTS

| 6,148,234 A | 11/2000 | Struble |
| 6,687,545 B1 | 2/2004 | Lu |
| 8,050,756 B2 | 11/2011 | Zhu et al. |
| 8,467,871 B2 | 6/2013 | Maskara |
| 8,538,521 B2 | 9/2013 | Zhu et al. |
| 8,755,881 B2 | 6/2014 | Kaiser et al. |
| 8,761,880 B2 | 6/2014 | Maskara et al. |
| 8,838,237 B1 | 9/2014 | Niazi |
| 8,954,138 B2 | 2/2015 | Maskara et al. |
| 8,972,228 B2 | 3/2015 | Ghosh et al. |
| 9,061,158 B2 * | 6/2015 | Rockweiler .......... A61N 1/3712 |
| 9,352,159 B2 | 5/2016 | Fishel |

(Continued)

FOREIGN PATENT DOCUMENTS

WO   2008058265 A9   5/2008

OTHER PUBLICATIONS (PCT/US2021/041034) PCT Notification of Transmittal of the International Search Report and the Written Opinion of the International Searching Authority, dated Oct. 29, 2021, 12 pages.

*Primary Examiner* — Catherine M Voorhees
*Assistant Examiner* — Elizabeth K So

(57) ABSTRACT

A medical device processor is configured to receive at least one cardiac electrical signal that is sensed during bilateral bundle branch pacing delivered from a bipolar electrode pair comprising an anode positioned along a first bundle branch and a cathode positioned along a second bundle branch opposite the first bundle branch, determine at least one feature from the first cardiac electrical signal, determine that the at least one feature meets first bundle branch capture criteria; and determine anodal bundle branch capture in response to the first bundle branch capture criteria being met.

21 Claims, 19 Drawing Sheets

(56) References Cited

U.S. PATENT DOCUMENTS

| | | |
|---|---|---|
| 10,773,086 B2 | 9/2020 | Sheldon et al. |
| 11,253,699 B1* | 2/2022 | Williams ............ A61N 1/0573 |
| 2010/0069983 A1 | 3/2010 | Peacock, III et al. |
| 2011/0264158 A1 | 10/2011 | Dong et al. |
| 2012/0101542 A1 | 4/2012 | Arcot-Krishnamurthy et al. |
| 2012/0283587 A1 | 11/2012 | Ghosh et al. |
| 2015/0283388 A1 | 10/2015 | Rockweiler et al. |
| 2017/0232261 A1 | 8/2017 | Stadler et al. |
| 2018/0263522 A1 | 9/2018 | Ghosh et al. |
| 2018/0280057 A1 | 10/2018 | Seifert et al. |
| 2019/0083800 A1 | 3/2019 | Yang et al. |
| 2019/0111264 A1 | 4/2019 | Zhou |
| 2019/0111270 A1 | 4/2019 | Zhou |
| 2019/0126050 A1 | 5/2019 | Shuros et al. |
| 2019/0160288 A1* | 5/2019 | Stegemann ........ A61N 1/36514 |
| 2019/0192860 A1 | 6/2019 | Ghosh et al. |
| 2019/0201698 A1* | 7/2019 | Herrmann ............ A61N 1/3712 |
| 2020/0101279 A1 | 4/2020 | Drake et al. |
| 2020/0129772 A1 | 4/2020 | Casavant et al. |
| 2021/0015389 A1 | 1/2021 | Zhou et al. |
| 2021/0015390 A1 | 1/2021 | Zhou et al. |

\* cited by examiner

METHOD AND APPARATUS FOR DELIVERING BUNDLE BRANCH PACING

REFERENCE TO RELATED APPLICATIONS

This application claims the benefit of U.S. Patent Application No. 63/057,263, filed provisionally on Jul. 27, 2020, and the U.S. Patent Application No. 63/112,980, filed provisionally on Nov. 12, 2020, both of which are incorporated herein by reference in their entirety.

TECHNICAL FIELD

This disclosure relates to a system for determining capture of the right and left bundle branches for delivering bundle branch pacing.

BACKGROUND

During normal sinus rhythm (NSR), the heartbeat is regulated by electrical signals produced by the sino-atrial (SA) node located in the right atrial wall. Each depolarization signal produced by the SA node spreads across the atria, causing the depolarization and contraction of the atria, and arrives at the atrioventricular (AV) node. The AV node responds by propagating a depolarization signal through the bundle of His of the atrioventricular septum and thereafter to the bundle branches and the Purkinje muscle fibers of the right and left ventricles, sometimes referred to as the "His-Purkinje system."

Patients with a conduction system abnormality, e.g., poor AV node conduction, poor SA node function, or other conduction abnormalities, may receive a pacemaker to restore a more normal heart rhythm. Ventricular pacing may be performed to maintain the ventricular rate in a patient having AV conduction abnormalities. A single chamber ventricular pacemaker may be coupled to a transvenous ventricular lead carrying electrodes placed in the right ventricle (RV), e.g., in the right ventricular apex. The pacemaker itself is generally implanted in a subcutaneous pocket with the transvenous ventricular lead tunneled to the subcutaneous pocket. Intracardiac pacemakers have been introduced or proposed for implantation entirely within a patient's heart, eliminating the need for transvenous leads. An intracardiac pacemaker may provide sensing and pacing from within a chamber of the patient's heart, e.g., from within the right ventricle in a patient having AV conduction block.

Dual chamber pacemakers are available which include a transvenous atrial lead carrying electrodes which are placed in the right atrium and a transvenous ventricular lead carrying electrodes that are placed in the right ventricle via the right atrium. A dual chamber pacemaker senses atrial electrical signals and ventricular electrical signals and can provide both atrial pacing and ventricular pacing as needed to promote a normal atrial and ventricular rhythm and promote AV synchrony when SA and/or AV node or other conduction abnormalities are present.

Ventricular pacing via electrodes at or near the right ventricular apex has been found to be associated with increased risk of atrial fibrillation and heart failure. Alternative pacing sites have been investigated or proposed, such as pacing of the His bundle or left bundle branch (LBB). Cardiac pacing along the His-Purkinje system has been proposed to provide ventricular pacing along the heart's native conduction system. Pacing the ventricles via the His bundle or the LBB, for example, allows recruitment along the heart's natural conduction system, including the Purkinje fibers, and is hypothesized to promote more physiologically normal cardiac electrical activation than other pacing sites, such as the ventricular apex.

SUMMARY

The techniques of this disclosure generally relate to a medical device system for guiding implantation of a cardiac pacing electrode for delivering ventricular pacing pulses to a target site along the His-Purkinje system, e.g., along the His bundle, which may be along the lower His bundle, or along or in the vicinity of the left bundle branch (LBB) and/or the right bundle branch (RBB) of the His bundle. In some examples, a medical device operating according to the methods disclosed herein determines anodal and cathodal capture during bipolar pacing within the ventricular septum to provide simultaneous capture of the LBB and the RBB. In some examples, a bipolar bilateral bundle branch (BBB) capture threshold is determined based on the higher one of the anodal capture threshold and the cathodal capture threshold. The pacing pulse output, e.g., pacing pulse amplitude and/or pacing pulse width, can be set according to the bipolar BBB capture threshold for delivering cardiac pacing to the ventricular conduction system. When the bipolar BBB capture threshold exceeds a maximum pacing pulse output limit, a different bundle branch pacing electrode configuration may be selected. A bundle branch pacing electrode configuration that is associated with a relative improvement in ventricular electrical synchrony compared to the native heart rhythm and/or associated with a pacing energy required to achieve capture that is within acceptable limits may be selected.

Accordingly, the techniques of this disclosure are related to determining capture of the RBB and the LBB for achieving BBB pacing. Capture may be achieved in the area of the RBB by anodal stimulation when a pacing cathode is located in the area of the LBB and a pacing anode is located in the area of the RBB for delivering bipolar pacing pulses. Alternatively, an electrode positioned in the vicinity of the RBB may function as the pacing cathode and an electrode positioned in the vicinity of the LBB may function as the pacing anode. Simultaneous BBB capture may be achieved by cathodal capture of the RBB and anodal capture of the LBB or vice versa. A medical device operating according to the techniques disclosed herein may detect one or more features in one or more ECG and/or EGM signals for determining when BBB pacing capture is achieved. In some examples, multiple pacing configurations may be available using multiple electrodes which may be carried by one or more leads and the medical device housing. Capture thresholds for multiple pacing electrode configurations, which may include different combinations of available electrodes and/or different cathode and anode assignments to pacing electrodes may be determined by a processor of a medical device according to techniques disclosed herein. An optimal pacing electrode configuration may be identified by a medical device processor based on one or more features of sensed ECG and/or EGM signals representative of ventricular electrical synchrony and based on acceptable capture thresholds of the RBB and/or LBB and overall pacing pulse energy requirements. Capture may be verified periodically to promote effective BBB pacing.

In one example, the disclosure provides a medical device including a processor configured to receive at least one cardiac electrical signal that is sensed during bilateral bundle branch pacing delivered from a bipolar electrode pair comprising an anode positioned along a first bundle branch and a cathode positioned along a second bundle branch opposite the first bundle branch. The processor is further configured to determine at least one feature from the at least one cardiac electrical signal, determine that the at least one feature meets bundle branch capture criteria, and determine anodal bundle branch capture in response to the bundle branch capture criteria being met.

In another example, the disclosure provides a method including receiving at least one cardiac electrical signal that is sensed during bilateral bundle branch pacing delivered from a bipolar electrode pair comprising an anode positioned along a first bundle branch and a cathode positioned along a second bundle branch opposite the first bundle branch. The method further includes determining at least one feature from the first cardiac electrical signal, determining that the at least one feature meets bundle branch capture criteria, and determining anodal bundle branch capture in response to the bundle branch capture criteria being met.

In another example, the disclosure provides a non-transitory computer readable medium storing instructions which, when executed by a processor of a medical device, cause the device to receive at least one cardiac electrical signal that is sensed during bilateral bundle branch pacing delivered from a bipolar electrode pair comprising an anode positioned along a first bundle branch and a cathode positioned along a second bundle branch opposite the first bundle branch, determine at least one feature from the first cardiac electrical signal, determine that the at least one feature meets bundle branch capture criteria, and determine anodal bundle branch capture in response to the bundle branch capture criteria being met.

Further disclosed herein is the subject matter of the following clauses:

1. A medical device, comprising:
   a processor configured to:
      receive at least a first cardiac electrical signal that is sensed during bilateral bundle branch pacing delivered from a bipolar electrode pair comprising an anode positioned along a first bundle branch and a cathode positioned along a second bundle branch opposite the first bundle branch;
      determine at least one feature from the first cardiac electrical signal;
      determine that the at least one feature meets first bundle branch capture criteria; and
      determine anodal bundle branch capture in response to the first bundle branch capture criteria being met.

2. The medical device of clause 1, wherein the processor is further configured to:
   determine a pacing pulse output for bilateral bundle branch pacing in response to determining the anodal bundle branch capture; and 3. The medical device of clause 2, further comprising:
   a pulse generator configured to generate pacing pulses according to the determined pacing pulse output.

4. The medical device of any of clauses 1-3, wherein the processor is configured to:
   determine the at least one feature from the first cardiac electrical signal by determining at least one of a QRS width, a QRS amplitude, a QRS morphology, a QRS polarity, and an activation time.

5. The medical device of any of clauses 1-4, further comprising a sensing circuit configured to:
   receive the first cardiac electrical signal as a first unipolar signal via a first one of the anode and the cathode as a sensing electrode.

6. The medical device of clause 5, wherein:
   the sensing circuit is configured to receive a second cardiac electrical signal as a second unipolar signal via a second one of the anode and the cathode; and
   the processor is configured to determine the at least one feature by determining an activation time difference as a time interval between the first feature of the first cardiac electrical signal and a second feature of the second cardiac electrical signal; and
   determine that the activation time difference meets the first bundle branch capture criteria.

7. The medical device of any of clauses 1-6, further comprising a sensing circuit configured to pass at least the first cardiac electrical signal to the processor by sensing a bipolar signal via the anode and the cathode.

8. The medical device of clause 7, further comprising:
   a pulse generator configured to generate pacing pulses delivered via the anode and the cathode at each of a plurality of pacing pulse outputs;
   wherein the processor is further configured to:
      determine the at least one feature from the first cardiac electrical signal by:
         determining, from the bipolar signal, a first QRS morphology corresponding to a first pacing pulse output of the plurality of pacing pulse outputs;
         determining, from the bipolar signal, a second QRS morphology corresponding to a second pacing pulse output of the plurality of pacing pulse outputs, wherein the second pacing pulse output is greater than the first pacing pulse output and the second QRS morphology is different than the first QRS morphology; and
         detecting in the bipolar signal a change between the first QRS morphology and the second QRS morphology; and
      determine that the at least one feature meets the first bundle branch capture criteria in response to detecting the change in the bipolar signal between the first QRS morphology and the second QRS morphology.

9. The medical device of any of clauses 1-8, further comprising:
   a pulse generator configured to:
      generate a unipolar pacing pulse delivered via the cathode; and
      generate a bipolar pacing pulse delivered via the cathode and the anode; a sensing circuit configured to receive at least the first cardiac electrical signal by:
      receiving the first cardiac electrical signal as a first unipolar signal via the anode; and
      receiving a second cardiac electrical signal as a second unipolar signal via the cathode; and
   wherein the processor is further configured to:
      determine, from the first unipolar signal and the second unipolar signal following the unipolar pacing pulse, a first activation time difference from a first fiducial point of the first unipolar signal to a second fiducial point of the second unipolar signal;

determine, from the first unipolar signal and the second unipolar signal following the bipolar pacing pulse, a second activation time difference from the first fiducial point of the first unipolar signal to the second fiducial point of the second unipolar signal;

determine that the second activation time difference is less than the first activation time difference; and determine that the at least one feature meets the first bundle branch capture criteria in response to the second activation time difference being less than the first activation time difference.

10. The medical device of clause 9, wherein:
the pulse generator is configured to deliver a bipolar pacing pulse via the anode and the cathode at each of a plurality of pacing pulse outputs;
the processor is further configured to:
determine a first lowest pacing pulse output of the plurality of pacing pulse outputs that is associated with the first bundle branch capture criteria being met;
determine a bipolar bilateral bundle branch pacing capture threshold as the first lowest pacing pulse output of the plurality of pacing pulse outputs;
set a pacing therapy pulse output based on the bipolar bundle branch pacing capture threshold; and
control the pulse generator to deliver bipolar pacing pulses at the bipolar bilateral bundle branch pacing pulse output for capturing the first bundle branch via the anode and the second bundle branch via the cathode.

11. The medical device of clause 10, wherein the processor is further configured to:
determine that the bipolar bilateral bundle branch capture threshold is greater than a maximum pacing output limit; and
determine a second lowest pacing pulse output of the plurality of pacing pulse outputs that is associated with the second cardiac electrical signal meeting second bundle branch capture criteria; and
setting the pacing therapy pacing output based on the second lowest pacing pulse output that is associated with the second cardiac electrical signal meeting second bundle branch capture criteria; and
control the pulse generator to deliver pacing pulses at the single bundle branch pacing pulse output for capturing the second bundle branch via the cathode.

12. A method, comprising:
receiving at least a first cardiac electrical signal that is sensed during bilateral bundle branch pacing delivered from a bipolar electrode pair comprising an anode positioned along a first bundle branch and a cathode positioned along a second bundle branch opposite the first bundle branch;
determining at least one feature from the first cardiac electrical signal;
determining that the at least one feature meets first bundle branch capture criteria; and
determining anodal bundle branch capture in response to the first bundle branch capture criteria being met.

13. The method of clause 12, further comprising:
determining a pacing pulse output for bilateral bundle branch pacing in response to determining the anodal bundle branch capture; and 14. The method of clause 13, further comprising generating pacing pulses according to the determined pacing pulse output.

15. The method of any of clauses 12-14, further comprising:
determining the at least one feature from the first cardiac electrical signal by determining at least one of a QRS width, a QRS amplitude, a QRS morphology, a QRS polarity, and an activation time.

16. The method of any of clauses 12-15, further comprising receiving the first cardiac electrical signal as a first unipolar signal via a first one of the anode and the cathode as a sensing electrode.

17. The method of clause 16, further comprising:
receiving a second cardiac electrical signal as a second unipolar signal via a second one of the anode and the cathode; and
determining the at least one feature by determining an activation time difference as a time interval between the first feature of the first cardiac electrical signal and a second feature of the second cardiac electrical signal; and
determine that the activation time difference meets the first bundle branch capture criteria.

18. The method of any of clauses 12-17, further comprising receiving at least the first cardiac electrical signal by sensing a bipolar signal via the anode and the cathode.

19. The method of clause 18, further comprising:
delivering pacing pulses via the anode and the cathode at each of a plurality of pacing pulse outputs;
determining the at least one feature from the first cardiac electrical signal by:
determining, from the bipolar signal, a first QRS morphology corresponding to a first pacing pulse output of the plurality of pacing pulse outputs;
determining, from the bipolar signal, a second QRS morphology; and corresponding to a second pacing pulse output of the plurality of pacing pulse outputs, wherein the second pacing pulse output is greater than the first pacing pulse output and the second QRS morphology is different than the first QRS morphology;
detecting a change in the bipolar signal between the first QRS morphology and the second QRS morphology; and
determining that the at least one feature meets the first bundle branch capture criteria in response to detecting in the bipolar signal the change between the first QRS morphology and the second QRS morphology.

20. The method of any of clauses 12-19, further comprising:
generating a unipolar pacing pulse delivered via the cathode;
generating a bipolar pacing pulse delivered via the cathode and the anode;
receiving at least the first cardiac electrical signal by:
receiving a first unipolar signal via the anode; and
receiving a second cardiac electrical signal as a second unipolar signal via the cathode;
determining, from the first unipolar signal and the second unipolar signal following the unipolar pacing pulse, a first activation time difference from a first fiducial point of the first unipolar signal to a second fiducial point of the second unipolar signal;
determining, from the first unipolar signal and the second unipolar signal following the bipolar pacing pulse, a second activation time difference from the first fiducial point of the first unipolar signal to the second fiducial point of the second unipolar signal;
determining that the second activation time difference is less than the first activation time difference; and
determining that the at least one feature meets the first bundle branch capture criteria in response to the second activation time difference being less than the first activation time difference.

21. The method of clause 20, further comprising:
delivering a bipolar pacing pulse via the anode and the cathode at each of a plurality of pacing pulse outputs;
determining a first lowest pacing pulse output of the plurality of pacing pulse outputs that is associated with the first bundle branch capture criteria being met;
determining a bipolar bilateral bundle branch pacing capture threshold as the first lowest pacing pulse output of the plurality of pacing pulse outputs;
setting a bipolar bilateral bundle branch pacing pulse output based on the bipolar bundle branch pacing capture threshold; and
delivering bipolar pacing pulses at the bipolar bilateral bundle branch pacing pulse output for capturing the first bundle branch via the anode and the second bundle branch via the cathode.

22. The method of clause 21, further comprising:
determining that the bipolar bilateral bundle branch capture threshold is greater than a maximum pacing output limit; and
determining a second lowest pacing pulse output of the plurality of pacing pulse outputs that is associated with the second cardiac electrical signal meeting second bundle branch capture criteria;
setting a single bundle branch pacing pulse output based on the second lowest pacing pulse output that is associated with the second cardiac electrical signal meeting second bundle branch capture criteria; and
delivering pacing pulses at the at the single bundle branch pacing pulse output for capturing the second bundle branch via the cathode.

23. A non-transitory computer readable medium storing instructions which, when executed by a processor of a medical device, cause the device to:
receive at least a first cardiac electrical signal that is sensed during bilateral bundle branch pacing delivered from a bipolar electrode pair comprising an anode positioned along a first bundle branch and a cathode positioned along a second bundle branch opposite the first bundle branch;
determine at least one feature from the first cardiac electrical signal;
determine that the at least one feature meets first bundle branch capture criteria; and determine anodal bundle branch capture in response to the first bundle branch capture criteria being met.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
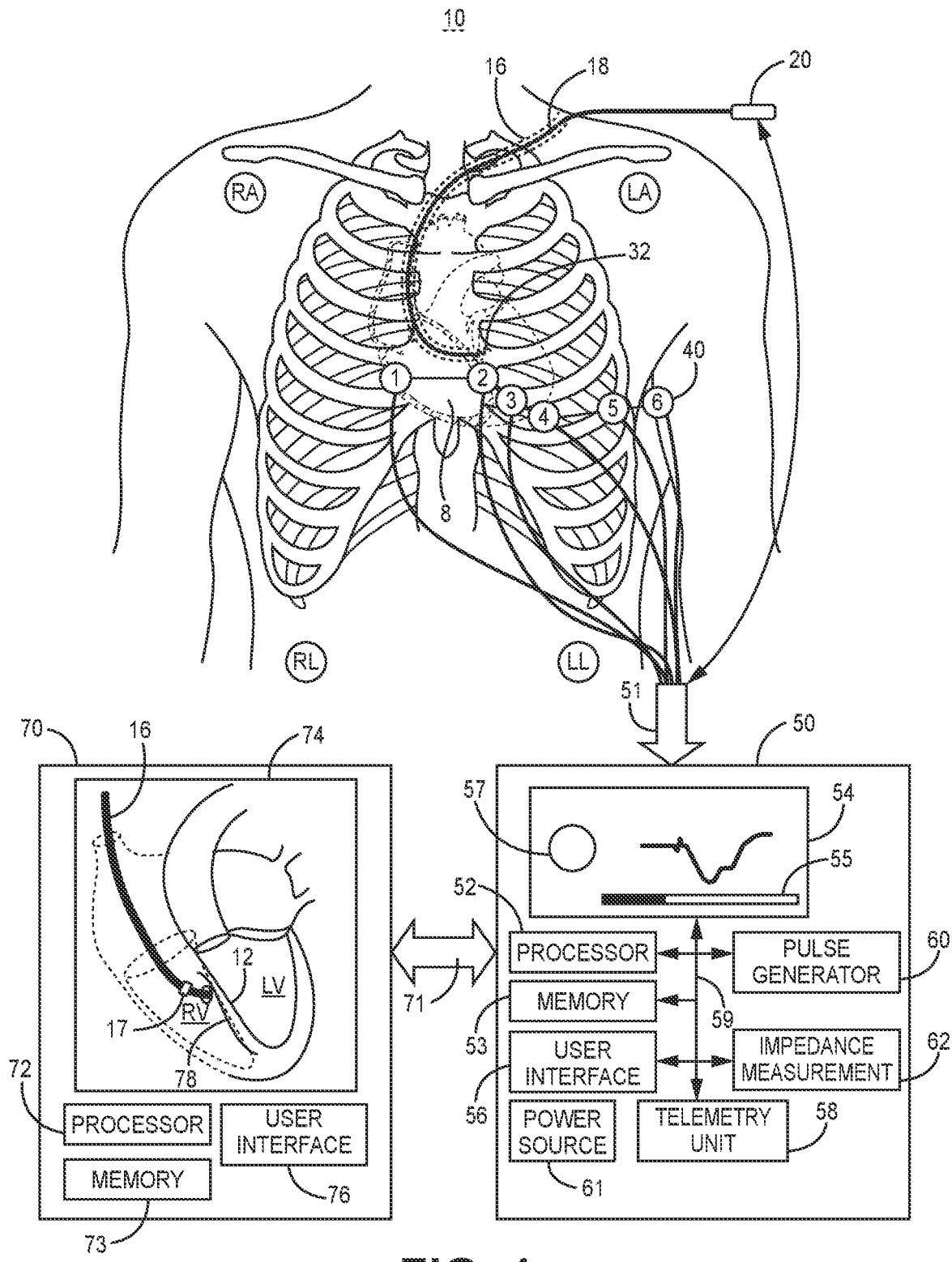
FIG. 1 is a conceptual diagram of a medical device system capable of sensing and analyzing cardiac electrical signals and generating and delivering cardiac pacing pulses.

A medical device system capable of delivering bundle branch pacing to improve electrical synchrony of the heart is disclosed herein. A processor of the medical device system is configured to receive cardiac electrical signals sensed during bundle branch pacing for determining bundle branch capture. Based on the determined bundle branch capture, the processor may select a pacing electrode configuration and/or pacing pulse output settings for delivering bundle branch pacing. As used herein, the term "pacing electrode configuration" refers to the number of pacing electrodes and their assigned polarities included in one or more unipolar and/or bipolar pacing electrode vectors selected for delivering ventricular pacing. In the examples presented herein the pacing electrode configuration includes at least one unipolar or bipolar electrode vector for delivering ventricular pacing via at least one bundle branch, e.g., the LBB or the RBB or both.

The term "pacing pulse output" refers to the pacing pulse amplitude and pulse width of a generated pacing pulse. For example, the pacing pulse output delivered by a given pacing electrode vector may be increased by increasing the pacing pulse amplitude and/or increasing the pacing pulse width. The pacing pulse output may be decreased by decreasing the pacing pulse amplitude and/or decreasing the pacing pulse width. The pacing pulse amplitude and pacing pulse width of a pacing pulse contribute to the pacing pulse energy delivered, which also depends on the pacing electrode impedance.

As used herein, the term "LBB pacing" refers to delivery of pacing pulses to or in the vicinity of the His bundle or LBB such that the LBB is captured by the pacing pulses. Accordingly a "LBB pacing site" or "LBB pacing location" may refer to a location in the tissue adjacent to the His-Purkinje system, e.g., generally in the area of the LBB or distal His bundle. The LBB pacing site may be accessed from the right ventricular septum such that a pacing electrode may be advanced toward the LBB pacing site. The term "RBB pacing" refers to delivery of pacing pulses to or in the vicinity of the His bundle or RBB such that the RBB is captured by the pacing pulses. The term "BBB pacing" refers to delivery of pacing pulses via one or more than one pacing electrode vector for capturing both the LBB and the RBB. As used herein, the term "bipolar BBB pacing" refers to BBB pacing using a single bipolar electrode pair that captures both the LBB and the RBB simultaneously by capturing one bundle branch via anodal capture at the pacing anode electrode and one bundle branch via cathodal capture at the pacing cathode electrode. BBB pacing may be achieved, however, using other pacing electrode configurations that include one pacing electrode vector, unipolar or bipolar, for pacing the RBB and a second pacing electrode vector, unipolar or bipolar, for pacing the LBB. Furthermore, in some instances, unipolar pacing of one bundle branch, right or left, may directly capture that bundle branch while virtual current or break excitation generated by the pacing electrode may excite the other bundle branch, potentially resulting in unipolar BBB pacing, with capture of both the LBB and RBB.

FIG. 1 is a conceptual diagram of a medical device system 10 capable of sensing and analyzing cardiac electrical signals and generating and delivering cardiac pacing pulses. In some examples, system 10 is capable of processing and analyzing cardiac electrical signals for guiding pacing electrode implantation in an area of the His bundle, the LBB or the RBB for delivering bundle branch pacing. The pacing electrode(s) may be lead-based electrodes, e.g., pacing tip electrode 32 carried by lead 18 as shown in FIG. 1, or housing-based electrodes of a leadless intracardiac pacemaker as described below in conjunction with FIG. 3.

In FIG. 1, cardiac pacing lead 18 is shown advanced within a patient's heart 8 for positioning pacing tip electrode 32 within the ventricular septum at an LBB pacing site. While tip electrode 32 is referred to herein as "pacing tip electrode 32," it is to be understood that the tip electrode 32 and other "pacing electrodes" referred to herein are not necessarily used only for pacing. Tip electrode 32 and other electrodes included in various pacing electrode configurations described herein may also be used for sensing cardiac electrical signals. The terms "pacing electrode," "pacing tip electrode," and "pacing ring electrode," therefore, are not intended to limit the function of a given electrode for pacing only since the electrode may be used for both pacing and sensing. Depending on selected pacing and sensing electrode vectors, in some instances a "pacing electrode" may be used only for pacing, only for sensing, both pacing and sensing, or not used at all for pacing or sensing when other electrodes are selected instead for pacing and sensing.

The system 10 includes an external device 50 for receiving and analyzing cardiac electrical signals during the pacing electrode implantation procedure. External device 50 may be embodied as a programmer used in a hospital, clinic or physician's office to acquire and analyze cardiac signals. External device 50 may alternatively be embodied as a handheld device or pacing system analyzer. External device 50 may receive ECG signals from one or more cutaneous or subcutaneous electrodes. In the example shown, ECG electrodes 40 including cutaneous electrodes 1-6 along with the four limb leads (R1, L1, R2 and L2) may be placed for acquiring a 12-lead ECG by external device 50. Additionally or alternatively, external device 50 may generate an EGM signal from cardiac electrical signals received via pacing lead 18. Pacing lead 18 may be electrically coupled to external device 50, e.g., via lead connector 20 before being coupled to an implantable medical device, for providing raw cardiac electrical signals received via electrode 32 paired with another sensing electrode, which may be another electrode carried by lead 18 as described below or a cutaneous or subcutaneous indifferent electrode.

Figure 2A:
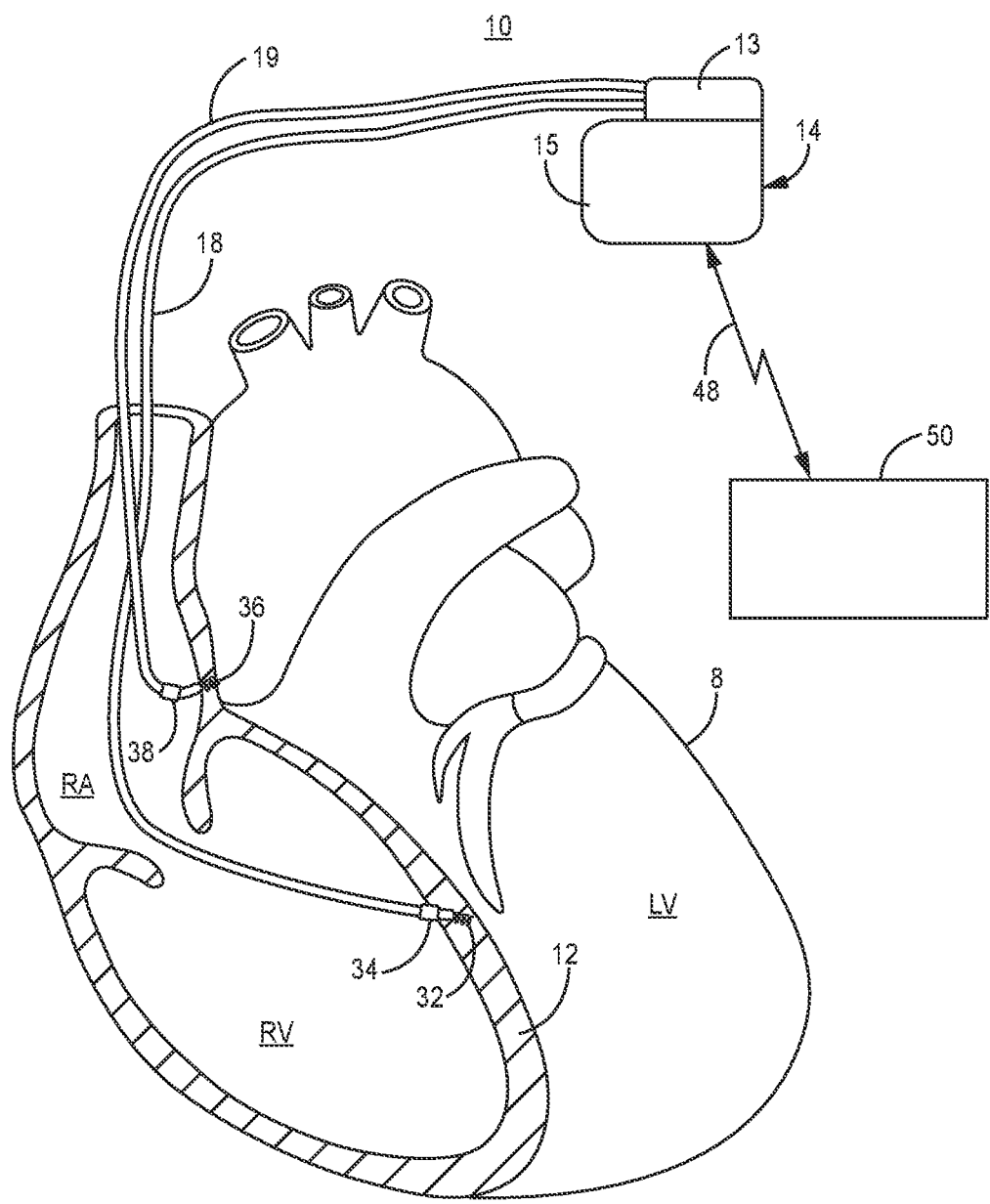
FIG. 2A is a conceptual diagram of pacing lead coupled to an implantable pacemaker capable of pacing a patient's heart and sensing cardiac electrical signals via a medical electrical lead.

External device 50 may include an electrode/lead interface 51 for receiving input from ECG electrodes 40 and/or lead 18, processor 52, memory 53, display unit 54, user interface unit 56, telemetry unit 58, pulse generator 60 and impedance measurement unit 62. Processor 52 is configured for processing cardiac electrical signals received from ECG electrodes 40 and/or pacing lead 18 for generating ECG and/or EGM signals, respectively, representative of cardiac electrical events during advancement of one or more pacing electrodes to one or more pacing sites and during bundle branch pacing. For example, during an implantation procedure, processor 52 may be configured to analyze the ECG and/or EGM signals for detecting signal features indicative of the location of tip electrode 32 within the interventricular septum. Based on the signal analysis, processor 52 may determine a location of tip electrode 32 (and a proximal ring electrode 34 as shown in FIG. 2A) relative to the RBB and LBB and generate user feedback signals based on the determined location.

Processor 52 may be coupled to the other components and units of external device 50, e.g., via a data bus 59, for controlling the functions attributed to external device 50 herein. For example, processor 52 may pass generated ECG and/or EGM signals and user feedback signals to a display unit 54, control pulse generator 60 to generate pacing pulses, control impedance measurement unit 62 to perform an electrode impedance measurement, etc. During an implant procedure or during patient follow up visits, pulse generator 60 may generate pacing pulses delivered via electrodes carried by lead 18. Pacing pulses may be delivered according to one or more pacing electrode configurations and pacing pulse output settings.

According to the techniques disclosed herein, processor 52 may determine capture of the RBB, capture of the LBB and BBB capture based on an analysis of the ECG and/or EGM signals acquired during bundle branch pacing according to the different pacing electrode configurations and/or pacing pulse output settings. As described below, processor 52 may be configured to determine anodal and/or cathodal pacing capture threshold of the RBB and/or the LBB for use in selecting a pacing electrode configuration and/or pacing pulse output settings for delivering BBB pacing. As used herein, the term "bundle branch capture criteria" refers to criteria applied to one or more cardiac signals, e.g., ECG and/or EGM signals, for determining that a pacing pulse has captured a bundle branch (RBB or LBB), causing depolarization of the bundle branch. The criteria may include one or more thresholds, ranges or other values applied to features of the cardiac electrical signal(s) for determining if the cardiac electrical signal is representative of bundle branch capture. The depolarization of the bundle branch due to pacing capture is conducted further along the native conduction system of the heart to cause ventricular myocardial depolarization. The bundle branch capture criteria applied to one or more cardiac signal features may be defined uniquely for determining capture of the RBB and for determining capture of the LBB. When a pacing pulse is delivered with the cathode electrode of the pacing electrode vector in the vicinity of a bundle branch (RBB or LBB), cathodal bundle branch capture (of the RBB or LBB) is determined when the corresponding bundle branch capture criteria are met by one or more cardiac signal features. When a pacing pulse is delivered with the anode electrode of the pacing electrode vector in the vicinity of a bundle branch (RBB or LBB), anodal bundle branch capture (of the RBB or LBB) is determined when the corresponding bundle branch capture criteria are met by one or more cardiac signal features. In some instances, BBB capture criteria may be applied to the cardiac signal(s) for determining RBB and LBB capture, which may include anodal and cathodal capture when a single bipolar pacing electrode vector is used to deliver BBB pacing. At other times, the BBB capture may occur when each of the RBB and LBB are captured by pacing pulses delivered via a cathode electrode positioned in the vicinity of the RBB and a cathode electrode positioned in the vicinity of the LBB (in unipolar or bipolar pacing electrode vectors), respectively.

In some examples, processor 52 may analyze the ECG and/or EGM signals for determining a recommended pacing electrode configuration based on the pacing pulse output settings required for achieving capture of the RBB and the LBB. A sensed EGM signal may be a near-field or far-field electrical signal, meaning that a sensing electrode pair may include an electrode located in the vicinity of the pacing site (near-field) or located remotely from the pacing site (far-field). As described below, the capture determination of the RBB and/or the LBB may be based on an improvement in ventricular electrical synchrony based on features of the ECG and/or EGM signals. For instance, a minimized cardiac electrical event signal width or a minimized interventricular activation time may indicate improvement in ventricular electrical synchrony. In some examples, this improvement in ventricular electrical synchrony is evidence of bundle branch capture. As used herein the "cardiac electrical event signal" generally refers to the cardiac electrical signal waveform attendant to the depolarization of the cardiac tissue. The cardiac electrical event signal may also be referred to as the "QRS signal" even though in some examples the waveform representing the depolarization of the cardiac tissue, which may be intrinsic or a pacing evoked response, may have a QS, QR, QSr' (a relatively large negative wave followed by a relatively small positive wave) or other waveform morphology that is different than the normal QRS complex.

Processor 52 executes instructions stored in memory 53. Processor 52 may include any one or more of a microprocessor, a controller, a digital signal processor (DSP), an application specific integrated circuit (ASIC), a field-programmable gate array (FPGA), or equivalent discrete or analog logic circuitry. In some examples, processor 52 may include multiple components, such as any combination of one or more microprocessors, one or more controllers, one or more DSPs, one or more ASICs, or one or more FPGAs, as well as other discrete or integrated logic circuitry. The functions attributed to processor 52 herein may be embodied as software, firmware, hardware or any combination thereof.

Memory 53 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 53 may be configured to store instructions executed by processor 52 for obtaining and analyzing cardiac electrical signals for determining a location of a pacing electrode relative to cardiac structures, such as the RBB and LBB and for determining pacing capture of the RBB and/or LBB and for determining the pacing capture threshold of the RBB and/or LBB. Memory 53 may store cardiac signal features determined by processor 52 for use in determining when the signal features meet capture criteria or other criteria indicative of pacing electrode placement at a bundle branch pacing site.

Display unit 54, which may include a liquid crystal display, light emitting diodes (LEDs) and/or other visual display components, may generate a display of the ECG and/or EGM signals and/or data derived therefrom. Display unit 54 may be configured to generate a graphical user interface (GUI) including various windows, icons, user selectable menus, etc. to facilitate interaction by a user with the external device 50. Display unit 54 may function as an input and/or output device using technologies including liquid crystal displays (LCD), quantum dot display, dot matrix displays, light emitting diode (LED) displays, organic light-emitting diode (OLED) displays, cathode ray tube displays, e-ink, or monochrome, color, or any other type of display capable of generating tactile, audio, and/or visual output. In some examples, display unit 54 is a presence-sensitive display that may serve as a user interface device that operates both as one or more input devices and one or more output devices.

In some examples, display unit 54 may generate a visual implant progress indicator 55 in response to data signals from processor 52 indicating the progress made in advancing pacing tip electrode 32 toward an LBB pacing site. Implant progress indicator 55 may include an advancing bar, arrow, wheel or other icon or a variable speed blinking icon, variable speed blinking LED or other visual indicator of the progress made in advancing pacing tip electrode 32 from the right border of the interventricular septum toward a left portion of the septum to an LBB pacing site. In some examples, user feedback generated and displayed by display unit 54 may include a report of the results of cardiac electrical signal analysis. Parameters determined from the signal analysis, such as shape of intrinsic QRS or evoked response morphology, intrinsic QRS or evoked response duration (width), right and/or left ventricular activation time data, or other parameters determined or detected from the cardiac electrical signals, may be reported to the user as quantitative values or qualitative indicators (e.g., increased, decreased, RBB block pattern, LBB block pattern, etc.).

In other examples, display unit 54 may produce an output to a user in another fashion, such as via a sound card, video graphics adapter card, speaker, one or more USB interfaces, video and/or audio output interfaces, or any other type of device capable of generating audio, video, or other output. For instance, display unit 54 may include a speaker 57 configured to generate an audible implant progress indicator in response to signals from processor 52. The audible implant progress indicator may be a variable speed beeping sound or tone that changes in frequency and/or tone as the pacing tip electrode 32 is advanced closer to or arrives at an LBB pacing site within the left portion of the interventricular septum. Audible user feedback signals generated by display unit 54 and broadcast by speaker 57 may include voiced notifications, e.g., indicating an electrode location or recommending advancement or retraction of the pacing tip electrode 32. Various user feedback signals described herein may be generated as visual, audible or a combination of visual and audible feedback signals.

In response to data received from processor 52, display unit 54 may generate a visual representation of RBB and/or LBB capture determinations and in some cases corresponding RBB capture threshold and/or LBB capture threshold according to one or more pacing electrode configurations and pacing pulse outputs. The visual representation may further include representations of cardiac electrical signals received during bundle branch pacing to enable a user to observe changes in the cardiac electrical signals that occur during bundle branch pacing, which may be indicative of worsening or improving ventricular electrical synchrony. Processor 52 may determine values of one or more cardiac electrical event signal features, e.g., QRS width, QRS amplitude, RBB activation time, LBB activation time, interventricular activation time difference or the like, during bundle branch pacing according to different pacing electrode configurations and/or pacing pulse output settings. Values or relative comparisons of determined cardiac electrical event signal features may be displayed by display unit 54 for review by a clinician. The display of pacing capture data and/or cardiac electrical event signal data may include an indication of a recommended or selected pacing electrode configuration and/or pacing pulse output settings in some examples.

User interface unit 56 may include a mouse, touch screen, keypad or the like to enable a user to interact with external device 50, e.g., to initiate and terminate an implant session, adjust settings of display unit 54, or make other user requests. Telemetry unit 58 includes a transceiver and antenna configured for bidirectional communication with a telemetry circuit included in an implantable pacemaker, which may be coupled to pacing lead 18 after pacing tip electrode 32 is deployed to an acceptable LBB pacing site. Telemetry unit 58 is configured to operate in conjunction with processor 52 for sending and receiving data relating to pacemaker functions via a wireless communication link with the implantable pacemaker.

External device 50 may include a pulse generator 60 for generating and delivering pacing pulses via lead 18 during the implant procedure. As described below, post-pace ECG and/or EGM signals may be analyzed for determining when criteria are met for detecting implantation of tip electrode 32 at an acceptable LBB pacing site and/or determining capture. In some examples, external device 50 may control pulse generator 60 to generate pacing pulses to perform ventricular capture tests during the electrode implantation procedure for verifying the location of one or more electrodes within the septum. Pulse generator 60 may vary the pacing pulse output for verifying capture and determining a pacing capture thresholds. Pulse generator 60 may include one or more holding capacitors charged to a pacing pulse voltage amplitude by a power source 61 of external device 50. The holding capacitor(s) may be coupled to an output capacitor via switching circuitry to deliver the pacing pulse via a selected pacing electrode configuration, e.g., tip electrode 32 and ring electrode 34 (seen in FIG. 2A), as the holding capacitor(s) are discharged for a selected pacing pulse width.

In some examples, external device 50 may include an impedance measurement unit 62 which may include a drive circuit for generating a drive current or voltage signal for measuring the pacing electrode impedance. The drive current or voltage signal may be applied to pacing tip electrode 32 and a return anode electrode, which may be an electrode carried by lead 18 (e.g., return anode electrode 34 shown in FIG. 2A) or another available cutaneous or subcutaneous electrode. Impedance measurement unit 62 may receive a resulting voltage or current signal in response to applying the drive signal and may use the resulting signal as an impedance measurement signal or convert the resulting signal to an impedance signal by determining the impedance based on the applied drive signal and measured signal. In some examples, the impedance measurement unit 62 may be incorporated in or share components with pulse generator 60. For example, a pacing pulse may be generated at a starting pacing voltage amplitude and processor 52 may determine the voltage change on a holding capacitor of pulse generator 60. The voltage of the holding capacitor may be sampled at the beginning and end of the pacing pulse width. The discharge of the holding capacitor during a pacing pulse, from a starting voltage to an ending voltage, is inversely correlated to the electrode impedance. The greater the voltage change, the lower the impedance. A low impedance may indicate that the pacing tip electrode 32 is in a blood volume rather than within septal tissue, e.g., within the RV chamber prior to advancement into the septum 12 or in the left ventricular chamber due to over advancement and perforation through the septum 12 into the left ventricle (LV). Impedance measurements may be performed by external device 50 for confirming an acceptable pacing site location of pacing tip electrode 32 within the interventricular septum in some examples.

External device 50 includes a power source 61 that is coupled to the various units of external device 50 for providing power to various circuits and components of external device 50 as needed. Power source 61 may include one or more rechargeable or non-rechargeable batteries or may be coupled to an external power source, such as plugged into an electrical outlet.

In some examples, system 10 may include an imaging unit 70 capable of generating an image of heart 8 on imaging display unit 74. The generated image may include markers or images of cardiac landmark structures such as the right ventricular septum and the location of tip electrode 32, one or more proximal ring electrodes (not shown in FIG. 1) and/or pacing lead 18 relative to cardiac structures. Imaging unit 70 may be a fluoroscopy unit or an ultrasound or echocardiography unit as examples. A catheter 16 may be advanced within heart 8 during the pacing lead implantation procedure to guide the distal end of pacing lead 18 and pacing tip electrode 32 to a location along the RV border of the interventricular septum 12 as represented in the image on imaging display unit 74. A catheter 16 may be used to deliver contrast dye for visualizing the location of the distal end of the pacing lead 18 and pacing tip electrode 32 relative to cardiac structures such as the RV septal border and the ring of the tricuspid valve annulus.

Imaging unit 70 may include a processor 72, memory 73 and user interface 76. In some examples, imaging unit 70 may be in communication with external device 50 via data link 71 for providing imaging data to processor 52. Processor 72 and/or processor 52 may be configured individually or cooperatively to execute firmware or software stored in imaging unit memory 73 and/or external device memory 53 for automatically generating cardiac structure landmark markers on the cardiac image generated by imaging display unit 74 to guide a user in advancing tip electrode 32 (and other electrodes in a pacing electrode configuration) to a pacing site. For example, an RV septal boundary marker 78 may be automatically generated by system 10 to provide a user with a visual marker of the RV septal border. The boundary marker 78 may be automatically generated by execution of an algorithm stored in memory 73 or 53 that determines the RV septal border location based on contrast between pixels corresponding to blood or contrast dye in the RV and the septal tissue, for example. Other cardiac structure landmark markers that may be generated automatically or in response to user input received via user interface 76 or display unit 74 may correspond to the tricuspid valve annulus and/or tricuspid septal leaflet or other landmark cardiac structures that may guide the user in navigating and advancing a pacing electrode toward a septal entry point and to a desired pacing site, which may be along the LBB, the RBB or other portion of the native conduction system such as along the His bundle or a distal portion of the His bundle.

The location of the pacing tip electrode 32 as it is advanced through the septum 12 may be tracked by imaging unit 70 and external device 50 based on analysis of ECG and/or EGM signals during an intrinsic (non-paced) ventricular rhythm and/or during delivery of pacing pulses via tip electrode 32. In some examples, external device 50 may additionally or alternatively perform pacing capture tests and/or impedance measurements using tip electrode 32 and in some cases an anode ring electrode as described below for generating data indicative of the location of pacing tip electrode 32 during advancement in interventricular septum 12.

Because the location of the tip electrode 32 within septum 12 relative to the LBB and the LV septal border may not be discernable from the image on display 74, analysis of ECG signals, EGM signals, pacing capture tests, and/or impedance signals may be performed by external device processor 52 to enable external device processor 52 to generate user feedback signals to guide advancement of tip electrode 32 to an acceptable LBB pacing site, and thereby position a proximal ring electrode in the area of the RBB for delivering BBB pacing. The user feedback signals may include the visual progress indicator 55, an audible progress indicator generated by speaker 57, visual markers generated on imaging display unit 74 of imaging unit 70, text or voiced notifications or graphical images generated on external device display unit 54 or any combination thereof.

In some examples, the catheter 16 or other delivery tool used to implant pacing tip electrode 32 may include a return anode electrode 17 (seen in the image on imaging display unit 74) for use in combination with the tip electrode 32 for sensing cardiac signals, performing pacing capture tests, and/or acquiring a pacing electrode impedance signal during implantation of lead 18. Lead 18 may include one or more ring electrodes that may be selected for use as a return anode electrode, as shown in FIG. 2A. However, in some instances an anode electrode carried proximally along lead 18 may be insulated within the body of catheter 16 or another delivery tool such that it is not available during the implant procedure. In this case, catheter 16 may carry one or more electrodes, such as ring electrode 17, for use as an anode electrode paired with pacing tip electrode 32. In other examples, any of ECG electrodes 40 or another dedicated cutaneous or subcutaneous electrode may be provided and coupled to external device 50 via interface 52 to serve as an indifferent electrode in combination with tip electrode 32 during the implant procedure. Examples of cardiac electrical signal and image based guidance techniques for implanting an electrode for use in delivering bundle branch pacing are described in U.S. Patent Application No. 62/876,634 filed provisionally on Jul. 20, 2019 (Zhou, et al.) and corresponding non-provisional U.S. patent application Ser. No. 16/931,567, filed Jul. 17, 2020 (Zhou, et al.) and U.S. patent application Ser. No. 16/990,804 filed Aug. 11, 2020 (Zhou, et al.), all of which are incorporated herein by reference in their entirety.

Pacing tip electrode 32 may be advanced into interventricular septum 12 for delivery of pacing pulses to the LBB or along the distal His bundle, for example. A user may be guided by user feedback signals generated by system 10 of FIG. 1 to an appropriate septal entry site of the tip electrode 32 generated by imaging display unit 74 and/or external device display unit 54 based on cardiac image processing by imaging unit 70 and/or cardiac electrical signal processing by external device 50. For example, a user may be guided to insert the pacing tip electrode 32 into septum 12 in a target region marked on a cardiac image displayed by imaging unit 74 that is approximately 10 to 20 millimeters below the tricuspid valve annulus, as identified by imaging unit processor 72. ECG and or EGM signal analysis as described below may be performed by external device processor 52 to guide the advancement of tip electrode 32 into a left portion of septum 12.

FIG. 2A is a conceptual diagram of pacing lead 18 coupled to an implantable pacemaker 14 capable of pacing a patient's heart 8 and sensing cardiac electrical signals via lead 18. After pacing tip electrode 32 is positioned at an acceptable pacing site under the guidance of system 10, as shown in FIG. 1, lead 18 may be coupled to an implantable pacemaker, such as pacemaker 14, for delivery of ventricular pacing pulses at a desired pacing site, e.g., the LBB. Pacemaker 14 may be a single chamber device capable of delivering ventricular pacing pulses and sensing electrical signals in the ventricles via lead 18. In the example shown in FIG. 2A, pacemaker 14 is a dual chamber device configured to receive an atrial pacing and sensing lead 19, which may be positioned in the right atrial chamber for delivering atrial pacing pulses and sensing atrial electrical signals via atrial electrodes 36 and 38. Pacemaker 14 may be configured to sense intrinsic atrial P-waves and deliver atrial pacing pulses in the absence of sensed, intrinsic P-waves. Pacemaker 14 may be configured to deliver atrial synchronized ventricular pacing by setting an AV delay in response to each sensed P-wave or atrial pacing pulse and delivering ventricular pacing pulses via lead 18 upon the expiration of the AV delay to improve the overall synchrony of the heart chambers. In still other examples, pacemaker 14 may be a multi-chamber pacemaker or biventricular pacemaker including additional or different leads and/or electrodes than shown in FIG. 2A. Examples of pacing electrode configurations that may include additional leads and electrodes than those shown in FIG. 2A are described below in conjunction with FIGS. 2B-2D.

Pacemaker 14 includes a housing 15, which may be hermetically sealed, to enclose internal circuitry corresponding to the various circuits and components for sensing cardiac signals from heart 8 and controlling electrical stimulation therapy, e.g., pacing therapy, delivered by pacemaker 14. Pacemaker 14 includes a connector block 13 coupled to housing 15 including at least one lead connector bore configured to receive the proximal end (e.g., lead connector 20 shown in FIG. 1) of pacing lead 18. Connector block 13 may have additional connector bores for optionally receiving an atrial pacing and sensing lead 19 or other leads in other examples. Lead 18 may be advanced transvenously into the RV via the RA for positioning pacing and sensing electrodes 32 and 34 within the interventricular septum 12. In particular, pacing tip electrode 32 is advanced within the septum 12 from the RV toward the LV to position tip electrode 32 at an LBB pacing site in some examples. Pacing tip electrode 32 may be a helical "screw-in" electrode that may be rotatably advanced into the septum 12, e.g., by rotation of the proximal lead connector 20 (shown in FIG. 1) though other types of electrodes may be used. A ring electrode 34 may be spaced proximally from pacing tip electrode 32 and may be used as the return anode electrode with the cathode tip electrode 32 for delivering pacing pulses and for sensing ventricular electrical signals.

While lead 18 is described herein as being deployed in the interventricular septum 12 for LBB pacing, it is recognized that techniques disclosed herein may be adapted for delivering BBB pacing at other locations based on processing and analysis of cardiac electrical signals, pacing capture tests, electrode impedance signals for determining and verifying capture of both the RBB and LBB. In the illustrative examples presented herein, the targeted cardiac tissue for pacing therapy delivery is the LBB and the RBB by delivering pacing pulses via a pacing electrode configuration selected for capturing both the LBB and the RBB. In other examples, however, the targeted pacing site may be only the LBB, only the RBB, either or both of the LBB or the RBB and a ventricular myocardial pacing site of the RV and/or the LV, as examples. The bundle branch capture determination techniques disclosed herein may be implemented in conjunction with or other multi-site pacing therapies which may include includes multiple unipolar and/or bipolar pacing electrode vectors for pacing multiple sites of heart 8.

The electrodes 32 and 34 are coupled to respective insulated conductors extending within the elongated, insulative body of ventricular lead 18. Each connector provides electrical connection of a respective electrode 32 or 34 to the proximal lead connector 20 (seen in FIG. 1). Proximal lead connector 20 provides connectability to external device 50, e.g., using electrical connectors such as alligator clips or other types of electrical connectors and wires, via electrode/lead interface 51. After confirmation of the location of pacing tip electrode 32 at a desired pacing site, e.g., based on output displayed by external device 50, proximal lead connector 20 may be coupled to connector block 13 of pacemaker 14, and thereby to circuitry enclosed within pacemaker 14.

As described below in conjunction with FIG. 4, cardiac electrical signal sensing circuitry included in pacemaker 14 may receive a cardiac electrical signal from electrodes 32 and/or 34 of pacing lead 18 for sensing ventricular signals including QRS signals attendant to ventricular depolarization. Electrodes 32 and 34 may be selected in a bipolar ventricular pacing and/or sensing electrode pair or one or both electrodes carried by pacing lead 18 may be used in combination with pacemaker housing 15 for delivering unipolar pacing pulses and/or receiving a unipolar cardiac electrical signal for sensing cardiac electrical events by cardiac electrical signal sensing circuitry. Techniques disclosed herein enable a processor of pacemaker 14 or external device 50 to determine anodal capture of the RBB and cathodal capture of the LBB for providing bipolar BBB pacing using a single bipolar pacing electrode vector (with tip electrode 32 as the cathode and ring electrode 34 as the anode). Alternatively, tip electrode 32 may be selected as the anode and ring electrode 34 may be selected as the cathode in a bipolar pacing electrode configuration for delivering bipolar BBB pacing by cathodal capture of the RBB and anodal capture of the LBB.

It is to be understood that although pacemaker 14 is illustrated in FIG. 2A as a pacemaker capable of delivering atrial pacing via lead 19 and ventricular pacing (of the ventricular conduction system) via lead 18, pacemaker 14 may be configured as an implantable cardioverter defibrillator capable of delivering both low voltage cardiac pacing therapies and high voltage cardioversion and defibrillation (CV/DF) shocks. In this case, pacemaker 14 may be coupleable to at least one lead carrying at least one high voltage CV/DF electrode such as an elongated coil electrode, which may be carried by lead 18 in addition to pacing and sensing electrodes 32 and 34.

Pacemaker 14 is shown in telemetric communication with external device 50 by a communication link 48. Communication link 48 may be established between pacemaker 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by pacemaker 14, including physiological signals or associated data derived therefrom, results of device diagnostics, and histories of detected rhythm episodes and delivered therapies, may be retrieved from pacemaker 14 by external device 50 following an interrogation command. In some examples, in addition to the pacing electrode implant guidance techniques described herein, external device 50 may be used in a hospital, clinic or physician's office to retrieve data from pacemaker 14 and to program cardiac signal sensing parameters, cardiac rhythm detection parameters and therapy control parameters used by pacemaker 14 in sensing the heart rhythm and delivering pacing therapies.

Figure 2B:
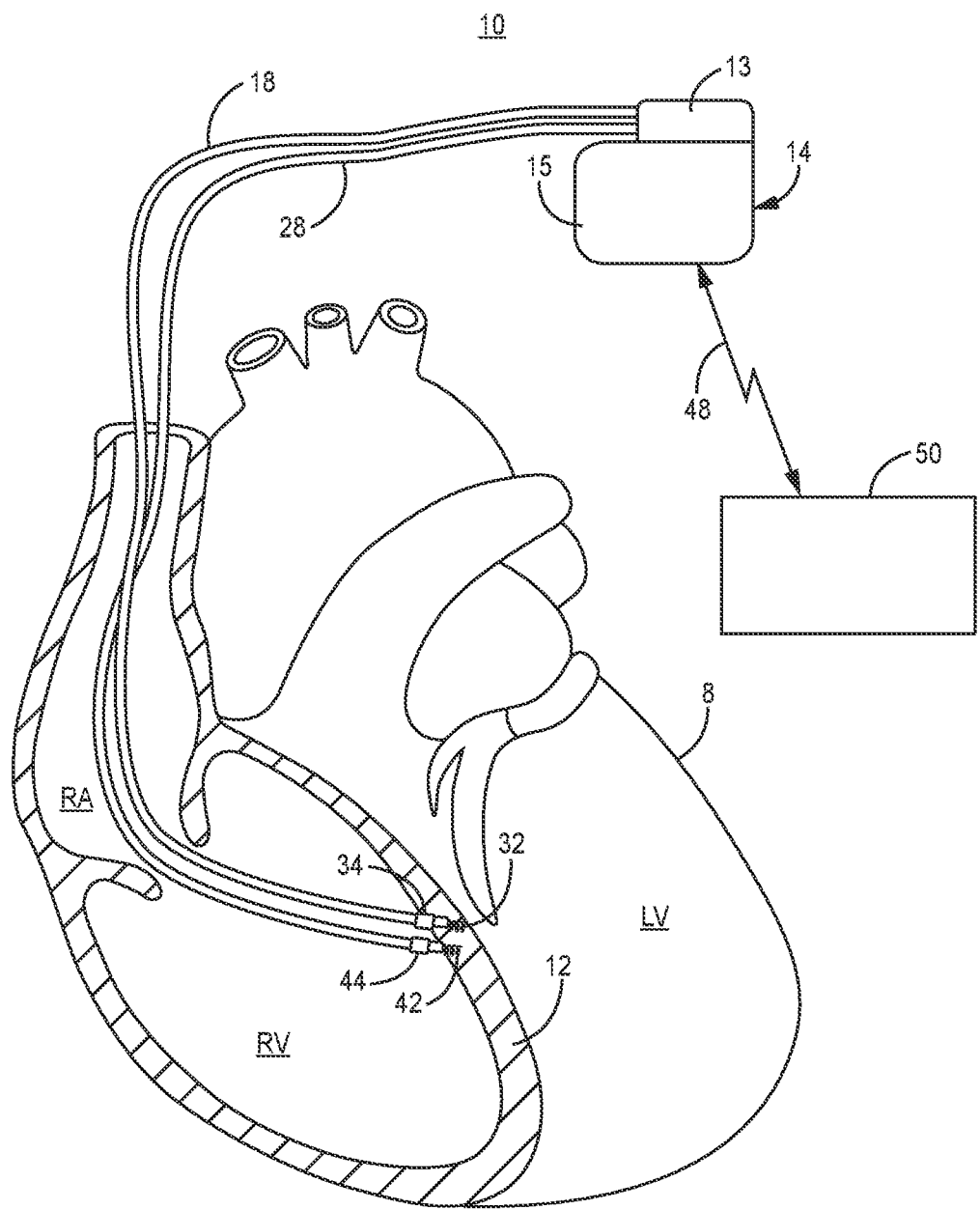
FIG. 2B is a conceptual diagram of the pacemaker of FIG. 2A coupled to two bipolar pacing and sensing leads for providing bilateral bundle branch (BBB) pacing according to one example.

FIG. 2B is a conceptual diagram of pacemaker 14 coupled to two bipolar pacing and sensing leads 18 and 28 that may be implanted in heart 8 for providing BBB pacing according to another pacing electrode configuration. In this example, lead 18 may be advanced to position tip electrode 32 in the left portion of the interventricular septum 12, in the vicinity of the LBB, for pacing the LBB in a bipolar pacing electrode configuration between tip electrode 32 as the cathode and ring electrode 34 as the return anode electrode. A second bipolar lead 28 may be advanced to position tip electrode 42 in the right portion of the ventricular septum 12, in the vicinity of the RBB for pacing the RBB in a bipolar pacing electrode configuration between tip electrode 42 and ring electrode 44.

In this pacing electrode configuration, two bipolar electrode vectors are used to individually pace the LBB and the RBB. The LBB pacing pulses and the RBB pacing pulses may be delivered via the two separate bipolar pacing electrode vectors simultaneously or separated by an interventricular pacing interval. The timing of the LBB pacing pulses and the RBB pacing pulses may be controlled relative to each other and/or relative to an atrial pacing pulse or sensed P-wave at a respective AV delay.

When two leads 18 and 28 are provided, one or both may be unipolar leads carrying a single electrode for pacing in a unipolar pacing electrode vector with pacemaker housing 15. One or both leads may be bipolar leads as shown and each electrode may be individually selectable as the anode or the cathode of a bipolar pacing electrode vector. Additionally, each electrode 32 or 34 and each electrode 42 or 44 may be selectable as the cathode electrode in a unipolar pacing electrode vector including pacemaker housing 15. Any available pacing electrode vector may be selected from the four electrodes 32, 34, 42, and 44 and pacemaker housing 15 for delivering LBB pacing, RBB pacing or BBB pacing. Thus multiple pacing electrode configurations may be selectable from among the electrodes 32, 34, 42 and 44 including bipolar pacing electrode vectors for providing bipolar BBB pacing using a single bipolar pacing electrode vector to achieve anodal and cathodal capture, BBB pacing using two different bipolar pacing electrode vectors, BBB pacing using two different unipolar pacing electrode vectors, BBB pacing using one unipolar and one bipolar pacing electrode vector, or single bundle branch pacing of only the LBB or only the RBB using a selected unipolar or bipolar pacing electrode vector.

Figure 2C:
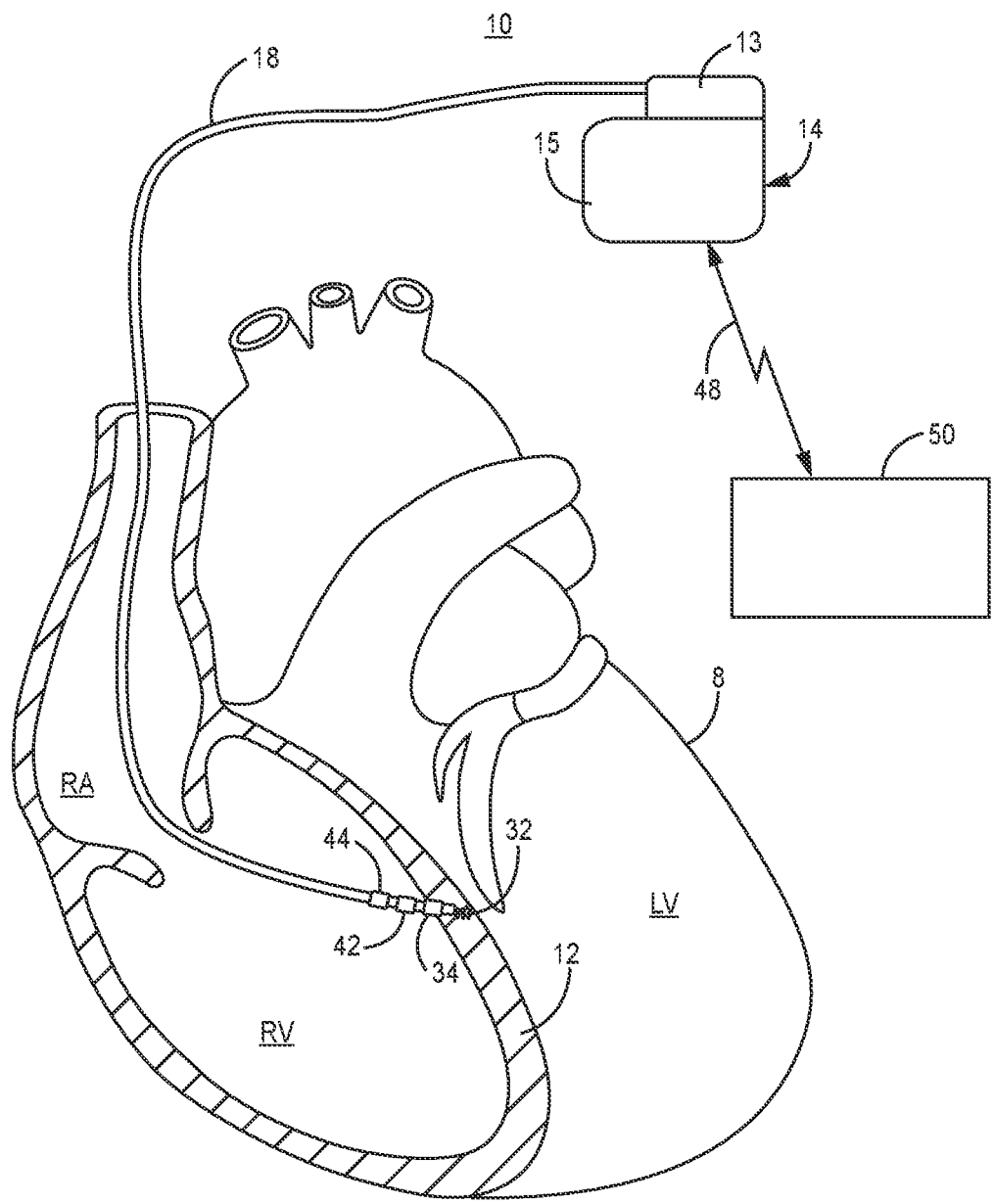
FIG. 2C is a conceptual diagram of the lead of FIG. 2A provided as a quadripolar lead.

FIG. 2C is a conceptual diagram of lead 18 provided as a quadripolar lead carrying four electrodes 32, 34, 42 and 44 along a single lead body of lead 18 rather than on two different lead bodies as shown in FIG. 2B. As described above, multiple pacing electrode configurations are selectable for delivering bundle branch pacing using electrodes 32, 34, 42 and/or 44 in various unipolar and/or bipolar pacing electrode vectors and selectable anode and cathode polarity assignments of each electrode 32, 34, 42 and 44. For example, tip electrode 32 and ring electrode 34 may deliver bipolar pacing pulses for capturing the LBB and ring electrodes 42 and 44 may deliver bipolar pacing pulses for capturing the RBB using two distinct bipolar pacing electrode vectors. Alternatively, a single bipolar pacing electrode vector, e.g., tip electrode 32 paired with any one of electrodes 34, 42 or 44, may be selected to deliver bipolar BBB pacing including cathodal and anodal capture. Any combination of two electrodes out of electrodes 32, 34, 42 and 44 may be selected in a bipolar pacing electrode vector with selectable anode and cathode polarities to achieve bipolar BBB pacing using a single bipolar pacing electrode vector. The selected electrode combination may be based on anodal and cathodal pacing capture thresholds of the LBB and RBB and/or the greatest improvement in ventricular synchrony based on an analysis of ECG and/or EGM signals according to the techniques disclosed herein.

Furthermore, any of the electrodes 32, 34, 42 and 44 may be selected as a pacing cathode electrode in a unipolar pacing electrode vector including pacemaker housing 15 for pacing either the RBB or the LBB. Two unipolar pacing electrode vectors may be selected based on the lowest pacing pulse output required to capture both of the RBB and the LBB. However in some examples, a maximum improvement in ventricular electrical synchrony may be achieved using single bundle branch pacing, e.g., only LBB pacing or only RBB pacing, using a selected bipolar or unipolar pacing electrode vector with only cathodal capture at the selected cathode electrode.

As described below, a processor of pacemaker 14 or external device processor 52 may analyze ECG and/or EGM signals and determine capture thresholds for selecting an optimal pacing electrode configuration and pacing pulse output settings. The optimal pacing electrode configuration may be identified as the pacing electrode configuration that results in a maximized improvement in ventricular electrical synchrony based on at least one feature of the cardiac electrical signal without exceeding a maximum limit of the pacing pulse output. In some examples, the optimal pacing electrode configuration may be identified as a pacing electrode configuration having the lowest pacing pulse output required to achieve capture and the maximized improvement in ventricular electrical synchrony.

Figure 2D:
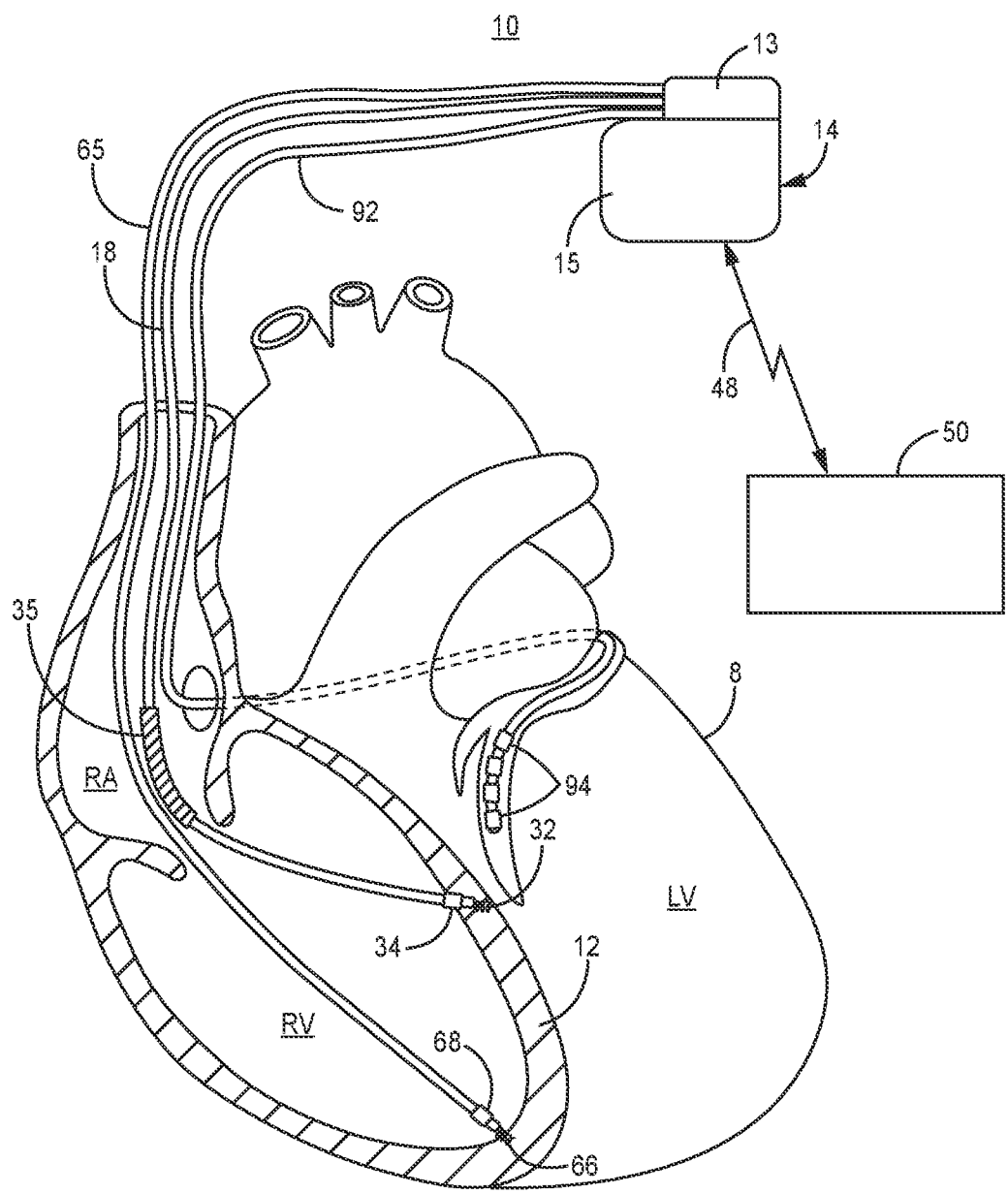
FIG. 2D is a conceptual diagram of the pacemaker of FIG. 2A configured as a multi-chamber pacemaker.

FIG. 2D is a conceptual diagram of pacemaker 14 configured as a multi-chamber pacemaker including an RV pacing and sensing lead 65 and a coronary sinus (CS) lead 92 in addition to lead 18 configured for delivering bundle branch pacing. While atrial lead 19 (shown in FIG. 2A) is not shown in FIGS. 2B-2D for the sake of clarity, it is to be understood that various pacing lead and electrode configurations described herein and shown in the accompanying drawings may include an atrial lead 19 for providing atrial sensing and pacing and enabling pacemaker 14 to deliver atrial synchronized ventricular pacing, e.g., in a DDD pacing mode. Furthermore, any of the leads carrying one or more electrodes shown in FIGS. 2A-2D may be combined in other combinations than the illustrative examples presented herein.

In FIG. 2D, pacemaker 14 is shown coupled to an RV lead 65 carrying a pacing tip electrode 66 and proximal ring electrode 68 which may be used for sensing RV signals and delivering myocardial pacing to the RV, e.g., from an RV apical pacing site as shown. CS lead 92 may be advanced into the RA, through the coronary sinus ostium and into a cardiac vein of the LV for positioning electrodes, collectively electrodes 94, along the LV myocardium for sensing LV signals and pacing the LV myocardium. CS lead 92 is shown as a quadripolar lead carrying four electrodes 94 that may be selected in various bipolar pacing electrode pairs for pacing the LV myocardial tissue.

In this example, pacemaker 14 may be capable of delivering high voltage therapies for cardioverting or defibrillating the heart 8 in response to detecting a ventricular tachyarrhythmia. As such, lead 18 is shown carrying a coil electrode 35 for delivering high voltage shock pulses. One or more coil electrodes may be included along one or more of leads 18, 65 or 92 in various examples. A coil electrode such as coil electrode 35 may be selected in a unipolar pacing electrode vector and for sensing EGM signals for detecting bundle branch capture. For example, BBB pacing may be achieved using ring electrode 34 paired with coil electrode 35 in one unipolar pacing electrode vector for pacing the RBB and using tip electrode 32 paired with coil electrode 35 in a second unipolar pacing electrode vector for pacing the LBB. Coil electrode 35 may be used with housing 15 for sensing a far-field EGM signal (a relatively more global EGM signal than the near field EGM signals sensed using electrodes 32 and 34 for example) for detecting changes in the QRS signal for confirming RBB capture, LBB capture and/or BBB capture.

When pacing lead 18 is positioned for delivering bundle branch pacing, of one or both bundle branches, bundle branch pacing may be combined with ventricular myocardial pacing in the RV (using RV lead 65) and/or in the LV (using CS lead 92) to achieve electrical and mechanical synchrony of the RV and LV. As such, in some examples, a processor of pacemaker 14 may select a pacing electrode configuration that includes two or more pacing electrode vectors for providing a combination of single bundle branch pacing or bilateral bundle branch pacing and ventricular myocardial pacing.

In some examples, an electrode 94 carried by CS lead 92 may be selected as a return anode electrode with one or both of the electrodes 32 and 34 selected as cathode electrodes. The pacing vector between tip electrode 32 and/or ring electrode 34 and the CS lead electrode 94 may capture the LBB and/or the RBB. The cathode electrode may be selected as either or both of electrodes 32 and 34 based on a capture threshold determination. For instance, the tip electrode 32 may be advanced to a location that is to the right of the LBB so that a pacing vector from tip electrode 32 to an electrode 94 carried by CS lead 92 encompasses the LBB and results in a relatively low pacing capture threshold of the LBB. In other instances, the tip electrode 32 may be advanced to a location that is more to the left of the LBB so that a pacing vector from the right electrode 34 to a CS lead electrode 94 results in a lower LBB capture threshold than the pacing electrode vector between the tip electrode 32 and a CS lead electrode 94. Using the techniques disclosed herein, multiple pacing electrode configurations using any of the available electrodes 32, 34, 35, 94, 66, and 68 and pacemaker housing 15 may be tested, including different electrode polarity assignments, to determine pacing capture thresholds and improvement in ventricular synchrony based on EGM and/or ECG signal analysis. Furthermore, electrodes 94 and electrodes 66 and 68 may be selected for use in one or more sensing electrode vectors for sensing EGM signal(s) analyzed for detecting pacing capture and ventricular synchrony improvement.

Figure 3:
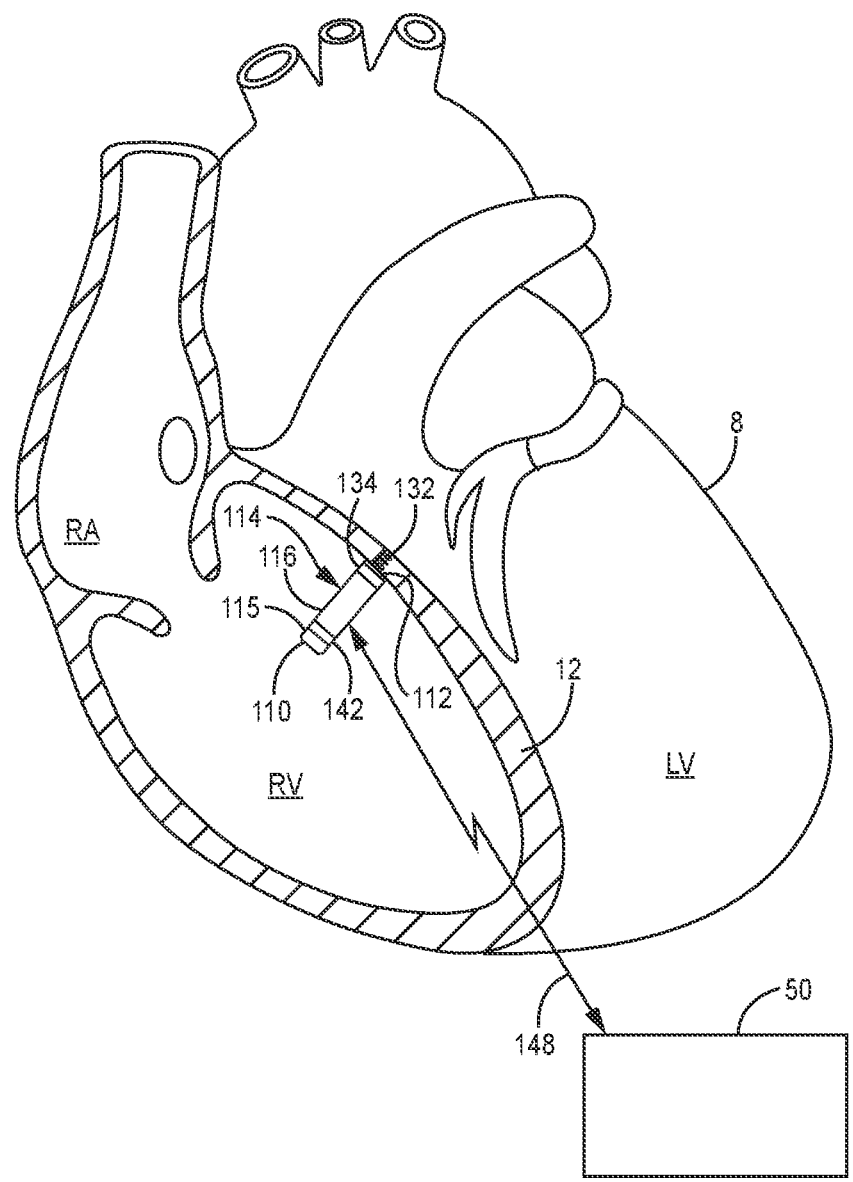
FIG. 3 is a conceptual diagram of a leadless intracardiac pacemaker positioned within the right ventricle for providing bundle branch pacing according to one example.

FIG. 3 is a conceptual diagram of a leadless intracardiac pacemaker 114 positioned within the RV for providing LBB pacing, RBB pacing or BBB pacing according to one example. The techniques disclosed herein for selecting pacing electrode configuration and pacing pulse output settings may be used in conjunction with implanting a leadless pacemaker, such as pacemaker 114, having a pacing electrode coupled to and extending from the pacemaker housing, without an intervening medical lead. Pacemaker 114 may include an elongated housing 115 having a longitudinal sidewall 116 extending from a housing proximal end 110 to a housing distal end 112. Pacemaker 114 is shown to include a pacing tip electrode 132 extending from the distal end 112 of pacemaker housing 115. Pacing electrode 132 may be referred to as a "distal tip electrode" and is shown as a "screw-in" helical electrode, extending away from distal end 112 of the pacemaker housing 115. Pacemaker 114 may include a distal housing-based electrode 134 along the distal end 112 of pacemaker housing 115 that may be selectable as the return anode electrode with tip electrode 132 for bipolar pacing of the LBB in the vicinity of the tip electrode 132. Bipolar BBB pacing may be achieved by cathodal capture of the LBB at tip electrode 132 and anodal capture of the RBB by anode electrode 134 on the distal end 112 of housing 115. The polarities of the tip electrode 132 and the distal housing electrode 134 may be reversed to achieve cathodal capture of the RBB and anodal capture of the LBB in some examples. Distal housing-based electrode 134 may be a ring electrode circumscribing a distal portion of the housing lateral sidewall 116 adjacent to distal end 112 or a button electrode, hemispherical electrode, segmented electrode or the like along the face of the distal end 112 of housing 115.

In the example shown, a proximal housing-based electrode 142, which may fully or partially circumscribe longitudinal sidewall 116 of the housing 115, may be provided as a return anode electrode. In other examples, a return anode electrode used in sensing and pacing may be positioned on housing proximal end 110 or on housing distal end 112 and may be a button, ring or other type of electrode. Pacing of the LBB may be achieved using the distal pacing tip electrode 132 as the cathode electrode and the proximal electrode 142 as the return anode. Pacing of the RBB may be achieved using the distal housing electrode 134 as a cathode electrode and the proximal ring electrode 142 as the return anode. In this way, BBB pacing may be achieved using two different pacing electrode vectors.

Intracardiac pacemaker 114 may be implanted in the RV of the patient's heart 8 with pacing tip electrode 132 advanced into interventricular septum 12 for delivery of pacing pulses to the LBB or along the distal His bundle, for example. A user may be guided by user feedback signals generated by system 10 of FIG. 1 to advance pacing tip electrode 132 to an appropriate septal entry site and to an LBB pacing site within the left portion of the ventricular septum 12. A proximal portion of the pacing tip electrode 132 may be electrically insulated, e.g., with a coating, in some examples such that only a distal portion of pacing tip electrode 132, furthest from pacemaker housing distal end 112, is exposed to provide targeted pacing at a tissue site that includes the LBB.

Tip electrode 132 may be an active fixation electrode, e.g., a helical electrode, providing fixation to anchor the pacemaker 114 at the implant position. In other examples, tip electrode 132 may be formed having a straight shaft with a distal active electrode portion or other type of electrode that is advanceable into the interventricular septum 12 to deliver pacing in a left portion of the septum 12 in the area of the LBB. In some examples, pacemaker 114 may include a fixation member that includes one or more tines, hooks, barbs, helices or other fixation member(s) that anchor the distal end of the pacemaker 114 at the implant site and may not function as an electrode. Examples of leadless intracardiac pacemakers that may be used in conjunction with the techniques described herein are generally disclosed in commonly-assigned U.S. Publication No. 2019/0111270 (Zhou) and U.S. Publication No. 2019/0083800 (Yang, et al.), both of which are incorporated herein by reference in their entirety.

Cardiac electrical signals produced by heart 8 may be sensed by pacemaker 114 using electrodes 132, 134 and/or 142. The raw cardiac electrical signal received via electrodes 132 and 142, electrodes 134 and 142 and/or electrodes 132 and 134, for example, may be processed by sensing and control circuitry included in pacemaker 114, e.g., as described below in conjunction with FIG. 4, for producing an EGM signal. The EGM signal may be transmitted wirelessly to external device 50 via communication link 48. The EGM signal may be processed and analyzed by the processor 52 of external device 50 for determining a location of tip electrode 132, e.g., within septum 12 relative to the LBB, using the techniques disclosed herein. In some examples, pacemaker 114 may be configured to perform a pacing capture test and/or an electrode impedance signal may be acquired using tip electrode 132 and/or distal housing electrode 134 for confirming a location of tip electrode 132 within septum 12 and distal housing electrode 142 in or along the right portion of the septum 12. Pacing capture test data and/or impedance data produced by pacemaker 114 may be transmitted to external device 50 for use in generating user feedback signals during advancement of pacing tip electrode 132 and/or for confirming a desired pacing site, pacing electrode configuration and pacing pulse output settings according to techniques disclosed here.

Pacemaker 114 may be advanced into the RV and to an implant site along the right border of septum 12 using a delivery tool, e.g., a catheter or other tool that facilitates pushing and/or rotation of pacemaker 114 for advancing pacing electrode 132 into the interventricular septum. Examples of leadless intracardiac pacemaker delivery tools that may be used in conjunction with the techniques described herein are disclosed in commonly-assigned U.S. Publication No. 2020/0101279 (Drake, et al.) and in U.S. Publication No. 2018/0280057 (Seifert et al.), both of which are incorporated herein by reference in their entirety. As described above in conjunction with FIG. 1, the catheter or delivery tool used to advance tip electrode 132 may include at least a return anode electrode in some examples for use in combination with the pacing electrode 132 for sensing cardiac signals, performing pacing capture tests, and/or acquiring an impedance signal when the proximal electrode 134 is enclosed within the delivery tool and unavailable for use as a return anode. In other examples, the delivery tool may include two or more electrodes used in sensing and/or delivering test pulses during advancement of the delivery tool toward a targeted implant site.

Figure 4:
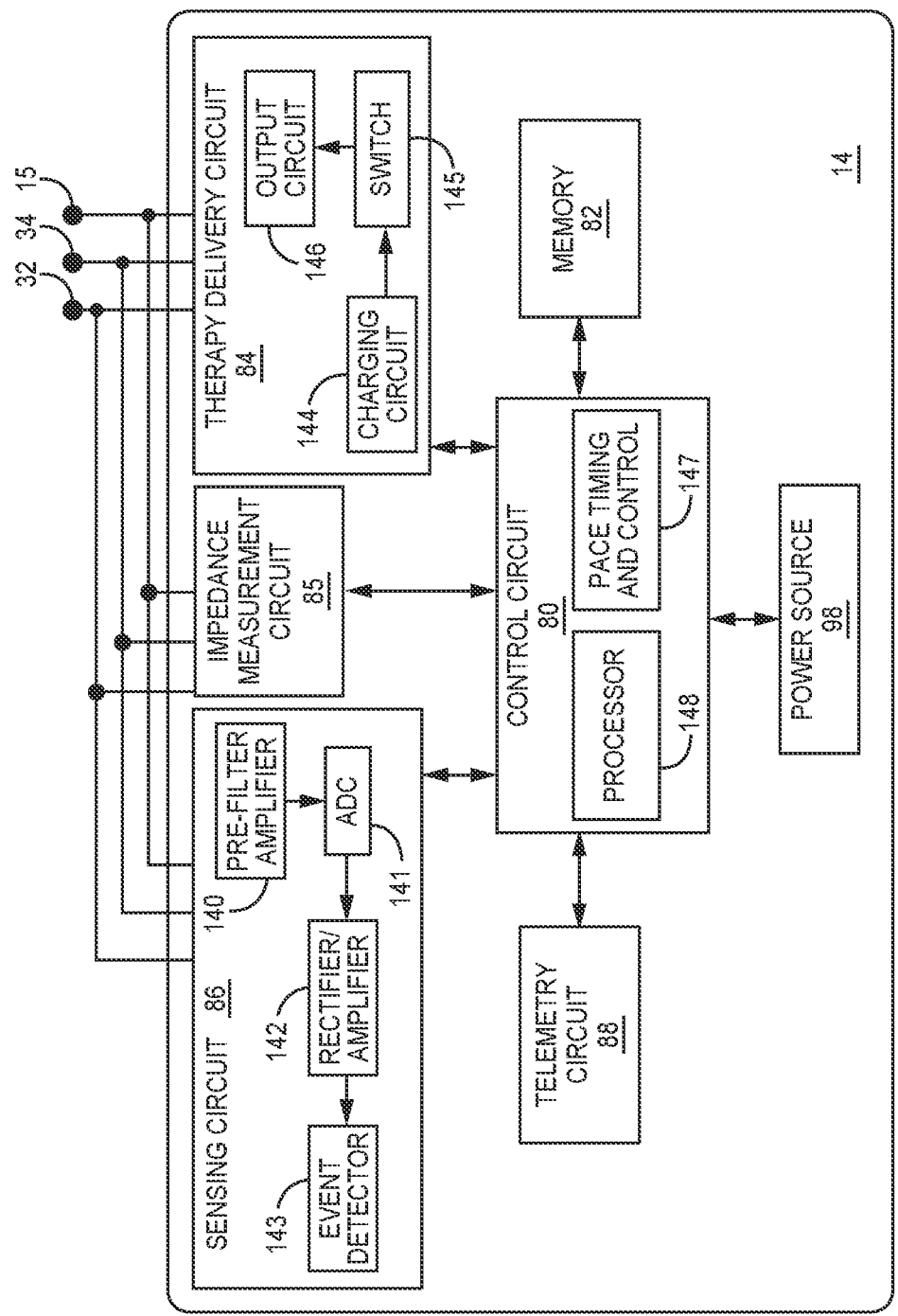
FIG. 4 is a schematic diagram of circuitry that may be enclosed within an implantable pacemaker configured to deliver pacing pulses and sense cardiac electrical signals according to techniques disclosed herein.

FIG. 4 is a schematic diagram of circuitry that may be enclosed within an implantable pacemaker configured to deliver pacing pulses and sense cardiac electrical signals according to one example. The block diagram of FIG. 4 is described with reference to pacemaker 14 coupled to lead 18 carrying electrodes 32 and 34 for the sake of convenience, but it is to be understood that the functionality attributed to the various circuits and components shown in FIG. 4 may correspond to circuitry enclosed in pacemaker 114 of FIG. 4, which may include housing based electrodes 132 and 134. Furthermore, while only two electrodes 32 and 34 are shown coupled to pacemaker 14 in the example of FIG. 4, it is to be understood that all available electrodes carried by a lead coupled to pacemaker 14, e.g., as shown and described in the various examples of FIGS. 2A-2D, and/or additional housing-based electrodes may be coupled to pacemaker 14 to enable selection of a variety of pacing electrode configurations, including selection of pacing electrode polarities.

The electronic circuitry enclosed within housing 15 includes software, firmware and hardware that cooperatively monitor cardiac electrical signals, determine when a pacing therapy is necessary, and deliver electrical pacing pulses to the patient's heart as needed according to a programmed pacing mode and pacing pulse output control parameters. The electronic circuitry includes a control circuit 80, memory 82, therapy delivery circuit 84, sensing circuit 86, telemetry circuit 88 and power source 98.

Power source 98 provides power to the circuitry of pacemaker 14 including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86, and 88 are to be understood from the general block diagram of FIG. 4 but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for delivering pacing pulses. Power source 98 is also coupled to components of sensing circuit 86, such as sense amplifiers, analog-to-digital converters, switching circuitry, etc., telemetry circuit 88 and memory 82 to provide power to the various components and circuits as needed.

The functional blocks shown in FIG. 4 represent functionality included in pacemaker 14 (or pacemaker 114) and may include any discrete and/or integrated electronic circuit components that implement analog and/or digital circuits capable of producing the functions attributed to pacemaker 14 (or pacemaker 114) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern medical device, given the disclosure herein, is within the abilities of one of skill in the art.

Control circuit 80 communicates, e.g., via a data bus, with therapy delivery circuit 84 and sensing circuit 86 for cooperatively sensing cardiac electrical signals and controlling delivery of cardiac electrical stimulation therapies in response to sensed cardiac events, e.g., R-waves attendant to ventricular depolarization, or the absence thereof. Electrodes 32 and 34 (or in the case of pacemaker 114, electrodes 132 and 134) may be electrically coupled to therapy delivery circuit 84 for delivering electrical stimulation pulses and to sensing circuit 86 for sensing cardiac electrical signals produced by the heart, including both intrinsic signals (such as intrinsic R-waves) produced by the heart in the absence of a pacing pulse that captures the heart and evoked response signals following a delivered pacing pulse of sufficient energy to cause cardiac capture. Pacemaker housing 15 is represented as an electrode coupled to therapy delivery circuit 84 and sensing circuit 86 for use as an electrode in combination with electrode 32 or electrode 34 in a unipolar sensing or pacing electrode vector.

Sensing circuit 86 may include an input pre-filter and amplifier 140 for receiving a cardiac electrical signal from a pair of sensing electrodes, e.g., electrodes 32 and 34, electrode 32 and housing 15, or electrode 34 and housing 15. The filtered and amplified signal may be passed to an analog-to-digital converter (ADC) 141 and a wide bandpass filter for producing a multi-bit digital cardiac electrical signal that may be passed to control circuit 80 and is referred to herein as a cardiac electrogram or "EGM" signal when the raw signal is sensed from within a heart chamber. Features of an EGM signal may be determined by processor 148 of control circuit 80 for use in determining the location of tip electrode 32 within the ventricular septum and for determining capture of the LBB and RBB as described below. The EGM signal(s) and/or data derived therefrom may be transmitted to external device 50 for processing and analysis for determining that the location of tip electrode 32 is at a desired LBB pacing site and for determining LBB and/or RBB pacing capture. While only electrodes 32 and 34 and housing 15 are shown coupled to sensing circuit 86, it is to be understood from the example pacing lead and electrode combinations shown in FIGS. 2A-2D that any available electrodes may be selected for sensing EGM signals in near-field and/or far-field sensing electrode vectors for passing one or more EGM signals to processor 148. As further described below, processor 148 may analyze EGM signals received from sensing circuit 86 to assess one or more pacing electrode configurations and/or one or more pacing pulse output settings selected for delivering bundle branch pacing. Processor 148 may be configured to determine bundle branch capture, including determining a pacing capture threshold, and an associated improvement in ventricular electrical synchrony based on the EGM signal analysis.

Sensing circuit 86 may further include a rectifier and narrowband filter and amplifier 142 for receiving the ADC signal and passing the rectified signal to cardiac event detector 143. Cardiac event detector 143 may produce a cardiac sensed event signal, e.g., a sensed ventricular event signal, in response to the rectified signal crossing a sensing threshold amplitude, e.g., an R-wave sensing threshold amplitude. The sensed event signal is passed to control circuit 80 for use in controlling pacing pulses. For example, in response to receiving a ventricular sensed event signal from event detector 143, a pace timing and control circuit 147 included in control circuit 80 sets a pacing escape interval timer for scheduling a ventricular pacing pulse. Pace timing and control circuit 147 may include various timers or counters for counting down a pacing interval. A sensed event signal may cause pace timing and control circuit 147 to trigger or inhibit a pacing pulse depending on the particular programmed pacing mode.

Furthermore, sensing circuit 86 may include multiple sensing channels, e.g., a ventricular event sensing channel and an atrial event sensing channel. For example, sensing circuit 86 may receive an atrial signal from atrial electrodes 36 and 38 shown in FIG. 2A. Cardiac event detector 143 may sense an atrial event in response to the atrial signal crossing a P-wave sensing threshold. Pace timing and control circuit 147 may receive the atrial sensed event signal and start an AV delay. Upon expiration of the AV delay the therapy delivery circuit 84 may generate a ventricular pacing pulse to be delivered by a selected pacing electrode configuration to provide atrial synchronized ventricular pacing via the LBB and/or RBB according to some examples. Pacemaker 14 may be configured for delivering ventricular bradycardia pacing therapy, atrial synchronized ventricular pacing, rate responsive pacing, dual chamber pacing, cardiac resynchronization therapy (CRT), anti-tachycardia pacing therapy or other pacing therapies, which may include pacing the ventricles via the LBB and/or RBB.

Therapy delivery circuit 84 is a pulse generator configured to generate pacing pulses according to one or more therapy protocols. Therapy delivery circuit 84 includes a charging circuit 144 including one or more charge storage devices such as one or more holding capacitors, an output circuit 146, and switching circuitry 145 that controls when the holding capacitor(s) are discharged through the output circuit 146 to deliver a pacing pulse via a selected pacing electrode vector, e.g., tip electrode 32 and ring electrode 34, coupled to the therapy delivery circuit 84. Output circuit 146 may include switching circuitry for selecting the pacing electrode vector and associated pacing electrode polarities coupled to a holding capacitor of charging circuit 144 via switch 145. For instance, output circuit 146 may include switching circuitry for selecting tip electrode 32 as a pacing cathode electrode with return anode electrode 34 for bipolar pacing or with housing 15 for unipolar pacing. Alternatively, ring electrode 34 may be selected as a cathode electrode with tip electrode 32 selected as the return anode in a bipolar pacing electrode vector or with housing 15 in a unipolar pacing electrode vector.

Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes, CRT, anti-tachycardia pacing sequences, etc. The microprocessor of control circuit 80 may also set the amplitude, pulse width, polarity, or other characteristics of the cardiac pacing pulses, which may be based on programmed values stored in memory 82.

Control circuit 80 may control therapy delivery circuit 84 to deliver pacing pulses to perform a pacing capture test during the implant procedure for use in determining a position of tip electrode 32 and/or ring electrode 34. For instance, a pacing capture test may be performed using ring electrode 34 as the cathode electrode to determine when the ring electrode 34 is in contact with or within septum 12. Additionally or alternatively, control circuit 80 may perform a pacing capture test or capture threshold search using one or more selected pacing electrode configurations. For example, in a bipolar BBB pacing configuration, therapy delivery circuit may select tip electrode 32 as the cathode electrode and ring electrode 34 as the anode and deliver pacing pulses at varying pacing pulse outputs (e.g., varying pulse amplitude and/or pulse width). Control circuit processor 148 may analyze one or more EGM signals received from sensing circuit 86 for determining cathodal and anodal capture thresholds of the LBB and RBB, respectively. Ring electrode 34 may be selected as the cathode electrode and tip electrode 32 as the anode electrode for bipolar BBB pacing in an alternative pacing electrode configuration, in which case the cathodal pacing capture threshold of the RBB and the anodal pacing capture threshold of the LBB may be determined by control circuit 80 based on an analysis of EGM signals received from sensing circuit 86, using the techniques described below. A bipolar pacing pair may be selected by switching circuitry of output circuit 146 for delivering bipolar BBB pacing by setting the pacing output (pacing pulse amplitude and pacing pulse width) above a BBB pacing capture threshold that results in anodal capture of one of the RBB or LBB and cathodal capture of the other of the LBB or RBB.

Therapy delivery circuit 84 may include multiple pacing channels for delivering separate pacing pulses to the LBB and the RBB or for selecting two or more pacing electrode vectors for providing BBB pacing. Each pacing channel may be coupled to selected electrodes via switching circuitry included in output circuit 146 for selecting various unipolar and/or bipolar pacing electrode combinations for delivering LBB, RBB pacing or BBB pacing. For example, when the two electrodes 32 and 34 are available, one pacing channel may be configured to deliver unipolar pacing of the LBB using pacing tip electrode 32, and a second pacing channel may be configured to deliver unipolar pacing of the RBB using pacing ring electrode 34. The pacemaker housing 15 may be used as an indifferent electrode for unipolar pacing of the RBB and LBB for providing unipolar pacing of each of the RBB and LBB separately, which may be referred to as "dual unipolar BBB pacing."

In some examples, additional electrodes may be available, e.g., along lead 18 which may be provided as a quadripolar lead (see FIG. 2C, for example), to enable bipolar pacing of the RBB and bipolar pacing of the LBB using one bipolar pair of electrodes positioned in the vicinity of the RBB and a second bipolar pair of electrodes position in the vicinity of the LBB. One pacing channel may be coupled to one bipolar pair for delivering bipolar pacing of the RBB, and a second pacing channel may be coupled to a second bipolar pair for delivering bipolar pacing of the LBB. In some examples, the return anode of the first bipolar pair and the second bipolar pair may be a shared anode to enable bipolar pacing of each of the RBB and LBB using three electrodes. As mentioned previously, when a single bipolar pacing vector is used to simultaneous pace both the RBB and the LBB by achieving anodal capture of one and cathodal capture of the other bundle branch, this bipolar pacing is referred to herein as "bipolar BBB pacing" to differentiate this pacing electrode configuration from the pacing electrode configuration that includes two separate bipolar pacing vectors used to separately pace the RBB and LBB, each using a distinct cathode electrode with a distinct or shared anode electrode to provide BBB pacing, which may be referred to herein as "dual bipolar BBB pacing."

As described above, when the CS lead 92 is coupled to pacemaker 14, one or more pacing electrode vectors may be selected for delivering RBB pacing and/or LBB pacing which may include any of the electrodes 94 carried by CS lead 92 paired with one or more electrodes implanted within the interventricular septum. Therapy delivery circuit 84 may include multiple pacing channels for delivering bundle branch pacing plus myocardial pacing, e.g., LV myocardial pacing using a pacing electrode vector that includes at least one of electrodes 94 and/or RV myocardial pacing using electrodes 66 and 68. Therapy delivery circuit 84 may further include an atrial pacing channel for delivering pacing pulses to the atria in dual chamber pacing modes, e.g., via atrial lead 19 shown in FIG. 2A.

Pacemaker 14 may include an impedance measurement circuit 85 for applying a drive signal to a selected electrode, e.g., pacing tip electrode 32 or proximal electrode 34, and recording a resultant signal indicative of the electrode impedance. When an electrode is within the blood pool of the RV or LV, the electrode impedance is very low compared to the electrode impedance when the electrode is within the interventricular septum. As such, relative changes in electrode impedance may be detected for determining when an electrode, e.g., tip electrode 32 and/or ring electrode 34, is within the RV blood pool, within the septum, or over-advanced into the LV blood pool.

Telemetry circuit 88 includes a transceiver and antenna for communicating with an external device 50 (shown in FIG. 1) using radio frequency communication or other communication protocols as described above. Control parameters utilized by control circuit 80 for sensing cardiac events and controlling pacing therapy delivery may be programmed into memory 82 via telemetry circuit 88. Under the control of control circuit 80, telemetry circuit 88 may receive downlink telemetry from and send uplink telemetry to the external device 50. Telemetry circuit 88 may be used to transmit one or more EGM signals acquired using tip electrode 32 and/or ring electrode 34 or data derived therefrom, a pacing electrode impedance signal or data derived therefrom, pacing capture test results and/or pacing capture threshold search results.

External device 50 may receive the data transmitted by telemetry circuit 88 for use in generating user feedback signals during the pacing electrode implant procedure. During an implant procedure, external device 50 may transmit a request to control circuit 80 via telemetry circuit 88 to acquire an EGM signal, an impedance signal, and/or perform a pacing capture test and transmit corresponding signals or data derived therefrom for use in generating visual and/or audible feedback representative of the location of pacing electrode 32 and/or proximal electrode 34. In some of the example techniques described below, external device processor 52 may receive EGM signals or data derived therefrom and/or pacing capture threshold test result from pacemaker 14 for use in identifying an optimal pacing electrode configuration and/or pacing pulse output settings for delivering bundle branch pacing for improving ventricular electrical synchrony while minimizing current drain from power source 98.

Figure 5:
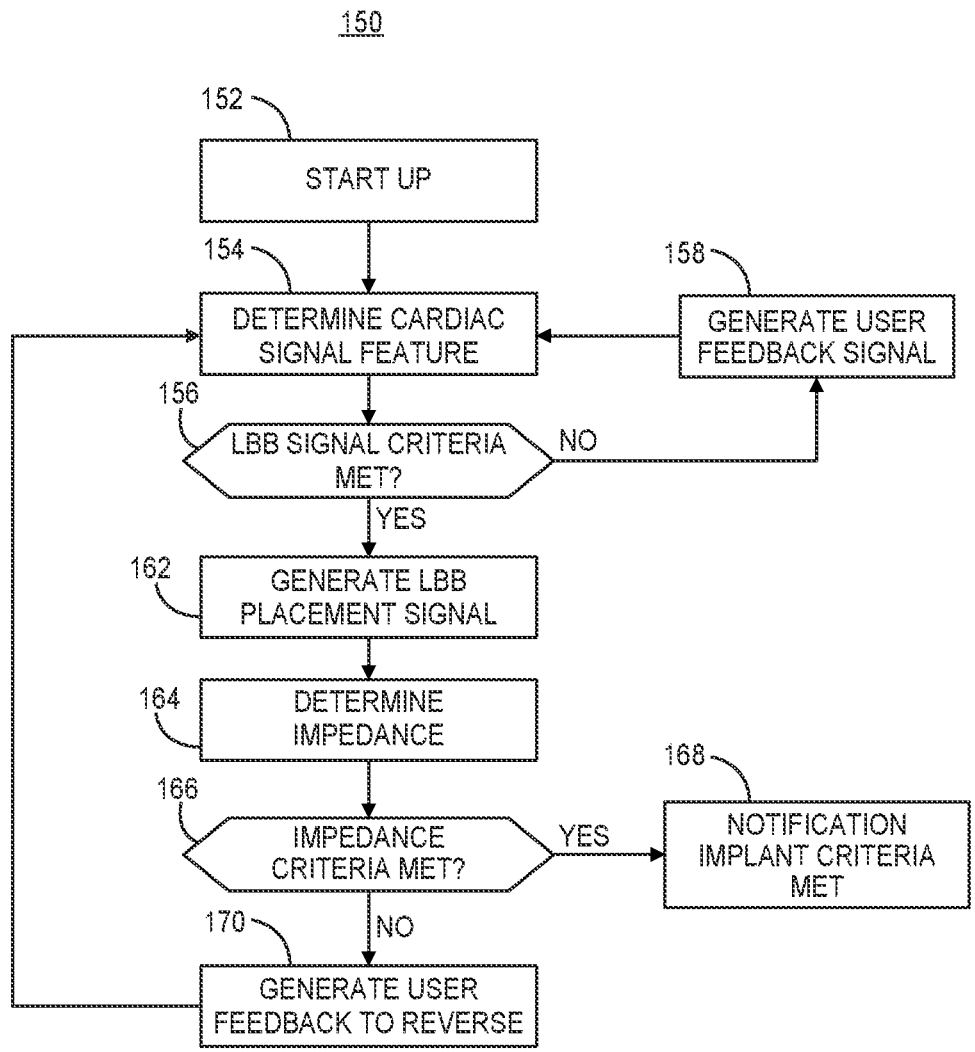
FIG. 5 is a flow chart of a method performed by the system of FIG. 1 for guiding implantation of a pacing electrode for delivering bundle branch pacing according to one example.

FIG. 5 is a flow chart 150 of a method performed by system 10 of FIG. 1 for guiding implantation of a pacing electrode for delivering bundle branch pacing according to one example. The process shown by flow chart 150 represents operations that external device 50 may perform to guide implantation of the pacing electrode once it is advanced to a location at or near the RV septal wall. The process of flow chart 150 may be initiated at block 152 once the pacing electrode, e.g., tip electrode 32 or 132 has been advanced transvenously toward or into the heart, e.g., within the RV near the septal border, but is not yet advanced into the septum 12.

At block 152, external device 50 may perform a start-up process in response to a user initiating the implant guidance procedure, e.g., via user interface 56. The start-up process may include generating ECG signals and/or EGM signals from electrical signals received via ECG electrodes 40 and/or electrodes 32 and 34 from lead 18 or electrodes 132 and 134 from pacemaker 114. In some examples, the EGM signals may be received by the external device telemetry unit 58 from an intracardiac pacemaker such as pacemaker 114 as described above via telemetry. In other examples, an implanted lead 18 not yet coupled to pacemaker 14 may be coupled to external device 50 for acquiring EGM signals. The ECG and/or EGM signals may be displayed on external device display unit 54.

During the start-up process at block 152, processor 52 may determine one or more ECG and/or EGM signal features to determine baseline cardiac electrical signal features prior to the pacing electrode (e.g., lead-based tip electrode 32 or housing-based tip electrode 132) being advanced into the septum 12. The start-up process at block 152 may additionally or alternatively include determining a baseline impedance using the pacing tip electrode 32/132 and a selected return electrode. Since a proximal ring electrode 34/134 may be within a delivery catheter or other tool, an alternative return electrode, e.g., a cutaneous or subcutaneous electrode, may be selected as the return anode in combination with pacing tip electrode 32/132 for acquiring an impedance signal. In some examples, an electrode carried by the delivery catheter or other tool, e.g., electrode 17 of catheter 16 (FIG. 1), may be used as the return anode for acquiring an impedance signal.

The start-up process at block 152 may include generating and displaying a notice or instructions to a user. A user notification instructing the user to advance the tip electrode 32/132 against the ventricular septum may be generated. In some examples, external device processor 52 may control external device pulse generator 60 to deliver a pacing pulse via the lead-based tip electrode 32 and a selected return anode electrode during the start-up process at block 152. The pacing pulse is delivered at a pulse energy that is expected to at least capture myocardial tissue. In the case of pacemaker 114, therapy delivery circuit 84 may deliver one or more pacing pulses in response to a pacing command transmitted from external device 50 to pacemaker 114. Processor 52 may determine that myocardial capture has occurred in response to a delivered pacing pulse, based on an analysis of an EGM or ECG signal. Determination of capture indicates that the pacing tip electrode 32/132 is against the ventricular septum. When capture does not occur, the pacing electrode may still be in the RV blood pool. The user notification instructing advancement of the electrode against the ventricular septum may continue to be generated when capture is not detected (and/or the ECG/EGM signature indicating a position at the RV septal border is not detected).

The ECG signal following a pacing pulse when the pacing electrode is in contact with the RV septum may be detected by processor 52 as a "W-wave" morphology in ECG lead V1, corresponding to an LBB block pattern (representing right bundle branch pacing). When the "W" shaped waveform is detected in response to a pacing pulse, processor 52 may determine that the pacing electrode is at a target septal entry site for advancing the electrode into the septum for LBB pacing. Accordingly, in some examples, capture detection by processor 52 may be followed by a user notification that the electrode 32/132 is in contact with the septal wall.

Once evidence of the pacing electrode being against the septum is detected by processor 52, which may be based on a change in impedance, a change in the ECG or EGM signal, or detection of pacing pulse capture or user input verification, the processor 52 may generate and display a user notification instructing the user to advance the pacing electrode, e.g., by rotating the proximal connector assembly 20 of lead 18 by a predetermined number of turns, for instance two to three or more clockwise turns. In the example of leadless pacemaker 114, tip electrode 132 may be rotated by rotating pacemaker 114 using a delivery tool to advance the pacing tip electrode 132 into the septum 12.

At block 154, processor 52 may determine one or more cardiac signal features from ECG and/or EGM signals as the pacing tip electrode 32/132 is advanced. In other examples, processor 52 may determine one or more cardiac signal features after receiving a user input indicating that the pacing tip electrode has been advanced the predetermined number of turns per the instructions displayed by the external device 50. The signal feature(s) is/are compared to LBB signal criteria at block 156. LBB signal criteria are discussed below, e.g., in conjunction with FIGS. 6-8.

The term "LBB signal" as used herein refers to a signal that is indicative of a pacing electrode location within a left portion of the interventricular septum. The LBB signal may be detected from a cardiac electrical signal, e.g., an ECG signal or an EGM signal, during an intrinsic ventricular rhythm or following a ventricular pacing pulse. The term "LLB signal criteria" refers to criteria applied by processor 52 to at least one ECG signal and/or the EGM signal for detecting an ECG and/or EGM signal waveform, pattern or feature that is expected to occur when the pacing electrode is in the left portion of the septum. For example, LBB signal criteria may include criteria for detecting an intrinsic LBB potential signal, an injury current based on elevated baseline amplitude after the LBB potential signal, the LV intrinsic activation time between the LBB potential signal and QRS maximum peak being within an LBB signal range, the LV paced activation time from a pacing pulse to the evoked response peak being within an LBB signal range, and/or any of the changes in the ECG signals described below that occur in the pacing-induced evoked response as the pacing tip electrode 32/132 is advanced from the right portion to the left portion of the septum 12.

In some examples, processor 52 may analyze the EGM signal generated from signals received via lead 18 (or from pacemaker 114) to detect an LBB signal as an LBB potential signal. The LBB potential signal is a signal spike occurring in the EGM signal immediately preceding a QRS signal attendant to the depolarization of the ventricular myocardium. The LBB potential signal represents the electrical potential conducted along the LBB during an intrinsically conducted ventricular beat that leads to ventricular myocardial depolarization. In one example, if the LBB potential signal is not detected, LBB signal criteria may be unmet at block 156. In a patient that does not have LBB block, an LBB potential signal may be detected from the EGM signal during an intrinsic (non-paced) ventricular rhythm. In other cases, if the patient has LBB block, the LBB potential signal may be detected during an escape beat.

However, when LBB block is present such that an intrinsic LBB potential signal is not present and/or the LBB potential signal accompanying intrinsic conduction along the LBB cannot be detected, pacing pulses may be delivered by the pacing electrode and the post-pace ECG and/or EGM signals may be analyzed to determine when LBB signal criteria are met. If the LBB signal criteria are unmet at block 156, processor 52 may generate a user feedback signal at block 158. The user feedback signal generated at block 158 may include adjusting a visual progress indicator 55, e.g., by advancing the progress indicator by a portion that indicates incomplete pacing electrode advancement, and/or adjusting an audible progress indicator, e.g., by increasing a rate or tone of audible signals. The user feedback signal may be a notification generated by display unit 54 to advance the pacing electrode by one or more turns or continue slow advancement of the pacing electrode. Processor 52 may be configured to analyze cardiac electrical signals as the pacing tip electrode 32/132 is advanced so that the clinician does not need to stop and wait for a feedback signal before advancing the pacing electrode further. In some examples, processor 52 may generate a user feedback signal to indicate that advancement should stop if the pacing tip electrode 32/132 is advanced into the left ventricular blood pool. Over advancement may be detected by processor 52 based on a sudden change in the ECG/EGM signal, loss of capture, or a sudden decrease in pacing impedance.

When processor 52 determines that LBB signal criteria are met at block 156, processor 52 may generate a user feedback signal that indicates that LBB pacing site placement of the pacing electrode is detected at block 162. The feedback signal may be advancement of the visual progress indicator 55 to a completed state, e.g., a green or other colored or shaded bar, circle or other visual representation of the advancement progress may be filled indicating 100% advancement. The feedback signal may include an adjustment of an audible signal, which may be a change in tone, a change in a rate of beeps, a voiced communication or other signal representative of successful positioning of the pacing tip electrode 32/132 at an LBB pacing site. The feedback signal may include a text notification displayed by display unit 54 indicating that an LBB signal has been detected.

In some examples, the pacing electrode guidance process may be complete upon determining that LBB signal criteria are met and the LBB placement signal is generated at block 162. In other examples, when processor 52 determines LBB signal criteria are met, processor 52 may perform additional analysis of cardiac signals for confirming the LBB pacing site placement of the pacing tip electrode 32/132. For instance, processor 52 may control impedance measurement unit 62 to determine an electrode impedance at block 164 using the pacing tip electrode 32 and a selected return anode electrode. Pacemaker impedance measurement circuit 85 may be used to determine an electrode impedance of pacing tip electrode 132 and a selected return anode electrode and the impedance may be transmitted to external device 50. The impedance may be compared to an impedance threshold at block 166. The impedance threshold may be set to a predetermined, default or nominal threshold value corresponding to a minimum expected impedance when the pacing electrode is within septal tissue and not in the blood pool. The threshold may be set based on a previously determined impedance in some examples. For instance, a baseline impedance determined during the start-up process at block 152, prior to advancement of the pacing tip electrode 32/132 into the ventricular septum, may be an impedance threshold for detecting over-advancement of the pacing tip electrode 32/132 into the LV blood pool. When the impedance is within a threshold range of the baseline impedance, over-advancement may be detected. In another example, a pacing electrode impedance may be determined during advancement in the septum before an LBB signal is detected, e.g., when the EGM and/or ECG signal analysis indicates a right or mid-septal location of the pacing electrode, as described below. This impedance is an indication of the pacing electrode impedance that is expected when the pacing tip electrode 32/132 remains within the septum. A threshold drop in impedance from this impedance determined during advancement may indicate over-advancement into the LV blood pool.

When the impedance is determined by processor 52 to be low, e.g., less than a predetermined impedance threshold, similar to a baseline RV blood pool impedance, or less than a previous impedance measurement determined during advancement within the septum, the pacing tip electrode 32/132 may be over-advanced and perforated into the LV chamber. When the pacing electrode impedance is determined to be low, therefore, processor 52 determines that impedance criteria are unmet at block 166 and may generate a user feedback signal at block 170 to indicate that the pacing tip electrode 32/132 may be over-advanced and should be reversed or retracted. For example, display unit 54 may generate a display at block 170 indicating that LV perforation may have occurred. The progress indicator 55, for example, may represent over-advancement by extending a bar beyond a 100% advancement limit with the portion extending beyond the 100% advancement displayed in red. External device processor 52 may generate other visual output representative of the impedance data and/or over-advancement determination which may include a representation of the pacing impedance being low or out of range. External device processor 52 may further generate a voiced or textual over-advancement warning on display unit 54. External device processor 52 may generate a user feedback instruction for display on display unit 54 to retract or rotate pacing tip electrode 32/132 counter-clockwise and may specify to retract by at least one or more turns, e.g., 3 to 4 turns, to withdraw the pacing tip electrode 32/132 back into the left portion of the septum 12.

When the pacing electrode impedance is too low, processor 52 may continue to determine cardiac signal features at block 154 in order to re-determine that LBB signal criteria are met at block 156 and verify that the pacing electrode impedance criteria are met at block 166. External device processor 52 may be configured to generate user feedback signals as needed throughout this process. Determination that the LBB signal criteria are met at block 156 and determination that the impedance criteria are met at block 166 are shown to be performed sequentially in FIG. 5. It is to be understood, however, that such determinations may be made concurrently, in parallel operations, or in a different order than shown here. When both the LBB signal criteria are met and the pacing electrode impedance criteria are met, processor 52 and display unit 54 may generate a user feedback signal at block 168 indicating that the LBB pacing site criteria are met. The user feedback signal may include an adjustment of a visual and/or audible progress indicator and/or a text or voice notification indicating that the pacing electrode is positioned for LBB pacing.

Figure 6:
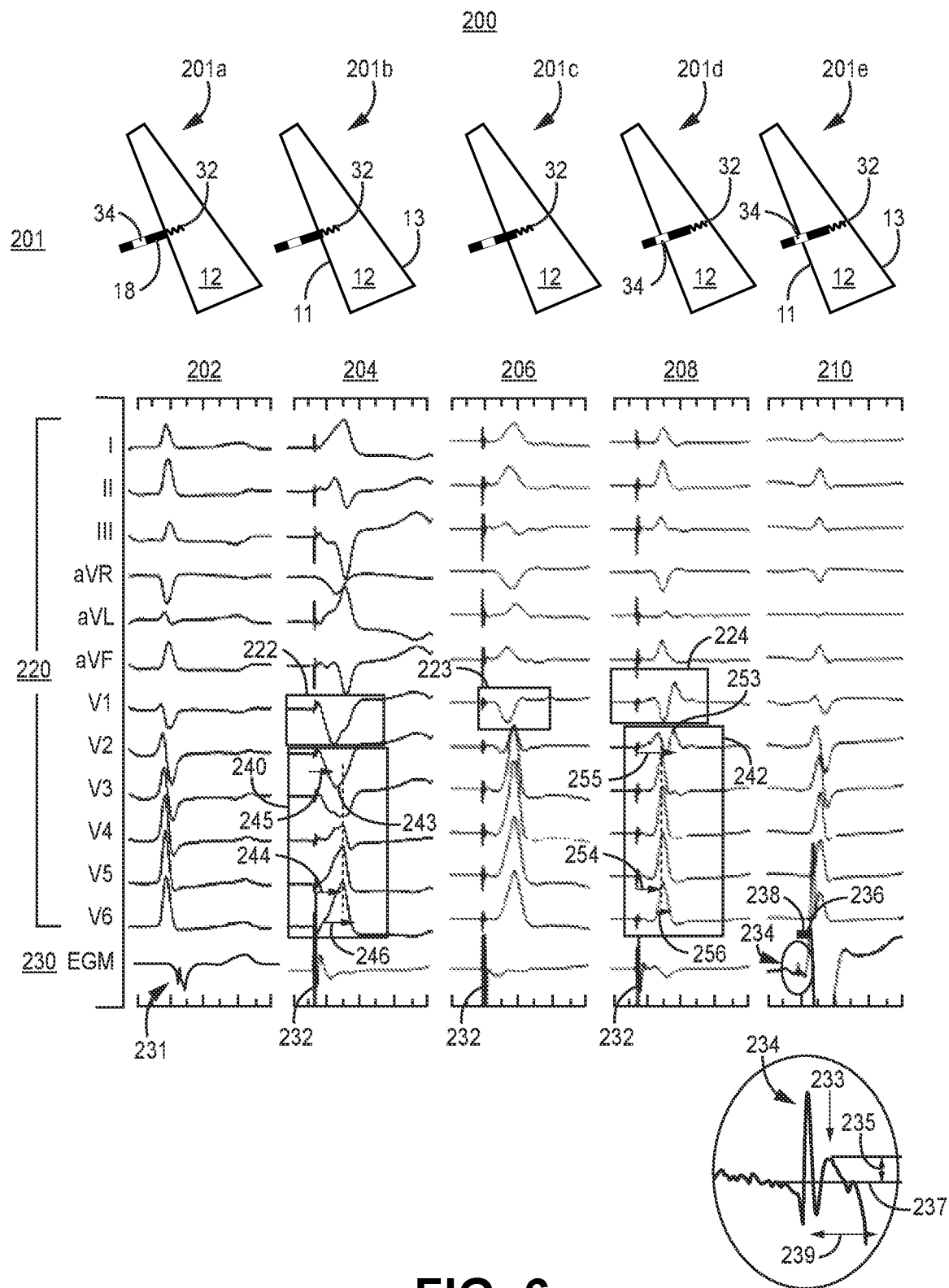
FIG. 6 is a diagram of sensed ECG and EGM signals that may be displayed and analyzed by the system of FIG. 1.

FIG. 6 is a diagram 200 of sensed ECG and EGM signals that may be generated as output by processor 52 for display to a user by external device 50 and analyzed by processor 52 to guide pacing electrode advancement. In FIG. 6, each column 202, 204, 206, 208, and 210 represents the ECG signal 220 and EGM signal 230 that may be sensed and displayed when the pacing tip electrode 32/132 is at a corresponding location within the ventricular septum as depicted in diagrams 201. Diagrams 201a through 201e (collectively diagrams 201) at the top of each column 202-210 illustrate the approximate depth of the pacing tip electrode 32 within the ventricular septum corresponding to the ECG or EGM signal waveforms shown in the column below.

For the sake of convenience, FIG. 6 is described with reference to lead-based pacing tip electrode 32 being advanced into septum 12. Moving left to right, the pacing tip electrode 32 is initially in the right portion of septum 12, near the right septal border 11 as shown by diagram 201a, and advances into the left portion of septum 12 without perforating left septal border 13, as shown by diagram 201e. The first column 202 depicts ECG signals 220 and EGM signal 230 sensed while pacing tip electrode 32 is in the right portion of septum 12 during an intrinsic ventricular rhythm (no pacing). An intrinsic QRS waveform 231 may be sensed by the pacing tip electrode 32 from the right septum. The second column 204 depicts ECG signals 220 and EGM signal 230 when a pacing pulse 232 is delivered using the pacing tip electrode 32 positioned in the right septum as shown in diagram 201b.

As shown by the diagram 201c above column 206, the ECG signals 220 and EGM signal 230 in column 206 correspond to a pacing tip electrode location that is approximately mid-way within the septum 12, between the right and left portions of the septum. The ECG signals 220 and the EGM signal 230 depicted in column 206 represent the signals that may be analyzed and displayed by external device 50 when the pacing tip electrode 32 is used to deliver a pacing pulse 232 in the inter-ventricular septum. Column 208 depicts ECG signals 220 and EGM signal 230 that are sensed when a pacing pulse 232 is delivered by the pacing tip electrode 32 in the left septum as indicated by the diagram 201d. Column 210 depicts ECG signals 220 and EGM signal 230 sensed during an intrinsic (non-paced) ventricular rhythm when the pacing tip electrode 32 is advanced into the left portion of septum 12 as shown in diagram 201e. The columns 208 and 210 represent ECG signals 220 and EGM signal 230 when pacing tip electrode 32 is in the vicinity of the LBB for delivering LBB pacing.

External device processor 52 (or pacemaker control circuit 80) may apply criteria for detecting an LBB signal that indicates a pacing electrode location in the left portion of the ventricular septum 12 to a cardiac electrical signal, e.g., an EGM signal 230 and/or one or more of ECG signals 220 obtained during a paced rhythm. Additionally or alternatively, external device processor 52 (or pacemaker control circuit 80) may apply criteria for detecting an LBB signal to the EGM signal 230 obtained during the intrinsic heart rhythm. In FIG. 6, the first column 202 and last column 210 of 12-lead ECG signals 220 and the EGM signal 230 are examples of signals that may be analyzed by processor 52 during an intrinsic ventricular rhythm. The EGM signal 230 may be generated from a raw cardiac electrical signal received via pacing tip electrode 32 and the return ring electrode 34 or another available return anode electrode. The EGM signal 230 in column 202 is an intrinsic signal received via the pacing tip electrode 32 in the right portion of the ventricular septum. Column 202 may represent the cardiac electrical signals that may be presented to a user on display unit 54 when pacing tip electrode 32 is first advanced into the septum 12.

The EGM signal 230 in column 210 represents a signal that may be presented to a user on display unit 54 and/or analyzed by external device processor 52 (or pacemaker control circuit 80) after advancement of the pacing tip electrode 32 into the left portion of the septum 12. When the pacing tip electrode 32 is positioned in the left portion of the septum 12, the EGM signal 230 presents an LBB potential signal 234 followed by a relatively large amplitude intrinsic QRS signal 236. The presence of the LBB potential signal 234 in the EGM signal 230 sensed using the pacing tip electrode 32 is evidence that the pacing tip electrode 32 is positioned in proximity to the LBB and well-positioned for LBB pacing. Accordingly, in some examples, processor 52 analyzes the EGM signal 230 as the user advances the pacing electrode into and across the ventricular septum 12. Processor 52 may analyze the EGM signal 230 until an LBB potential signal 234 is detected. One method for detecting the LBB potential signal 234 as an LBB signal is described below in conjunction with FIG. 10.

Additionally or alternatively, the time interval 238 from the LBB potential signal spike 234 to the maximum positive peak of the QRS signal 236 is determined by processor 52. When the LBB potential signal 234 is detected by processor 52 and an intrinsic QRS signal 236 is detected by processor 52 within a threshold time interval, e.g., within 10 to 40 ms, an LBB signal is detected by processor 52 as evidence of LBB pacing site placement of tip electrode 32.

In other examples, an injury current signal may be detected by processor 52 based on analysis of the EGM signal 230 sensed during an intrinsic ventricular rhythm using the pacing tip electrode 32. An elevated post-potential signal amplitude 233, immediately following LBB potential signal 234 (see the inset, enlarged diagram of LBB potential signal 234), is evidence of injury current. An elevated post-potential amplitude 233 is therefore an indication that the pacing tip electrode 32 has entered the left portion of the septum 12, causing local injury near the LBB.

Processor 52 may detect the injury current by determining and storing a baseline amplitude 237 (which may be an average baseline) determined prior to detecting the LBB potential signal 234 and determining the maximum amplitude 233 within an injury current detection window 239 following the LBB potential signal 234. The injury current detection window extends up to 10 ms, up to 20 ms, or up to 25 ms, as examples, after detection of the LBB potential signal 234. Processor 52 may determine the post-potential amplitude difference 235 as the difference between the maximum post-potential amplitude 233 (after LBB potential signal 234) and pre-potential amplitude 237 (prior to LBB potential signal 234). When this difference 235 between pre-potential amplitude 237 and the post-potential amplitude 233 is greater than a threshold amplitude difference or percentage change, e.g., at least 0.1 to 1 millivolt difference, an injury current and associated LBB potential signal 234 may be detected by processor 52 as an LBB signal meeting LBB signal criteria, indicating a left septal location of the pacing tip electrode 32/132.

In response to detecting the LBB potential signal 234 and/or the injury current based on the amplitude difference 235, processor 52 may generate or adjust a user feedback signal indicating placement of the pacing tip electrode 32 within a left portion of septum 12 in proximity to the LBB, with or without any further processing or analysis of cardiac electrical signals for verifying the LBB pacing site placement of the pacing tip electrode 32. While processor 52 is referred to as performing the detection of an injury current, LBB potential signal 234 and other EGM signal features determined in the disclosed techniques, it is to be understood that one or more processors included in the implantable pacemaker, e.g., processor 148 in control circuit 80 shown in FIG. 4, and/or the external processor 52 may individually or cooperatively perform the processing, analysis and detection steps disclosed herein.

In some examples, in addition or alternatively to analyzing the intrinsic EGM signal during pacing electrode advancement, processor 52 may control pulse generator 60 to deliver pacing pulses 232 via the pacing tip electrode 32 with a selected return anode (or send a pacing command to pacemaker 114 to deliver a pacing pulses via pacing electrode 132) and analyze one or more ECG signals 220 and/or EGM signal 230 for detecting an LBB signal.

When the pacing tip electrode 32 is within the right portion of the septal wall 12, relatively more proximate to the right septal border 11 than the left septal border 13 (e.g., as shown in diagram 201b), capture in the right portion of the ventricular septum 12 may occur resulting in a relatively wide, negative polarity V1 ECG signal 222. The wide negative polarity signal corresponding to capture in the right side of the septum 12 may have a characteristic "W" shape in the V1 ECG signal 222 and may correspond to an ECG signal that is observed when LBB block is present. The characteristic, wide, negative "W" shaped signal is a "LBB block-like signal" because the pacing evoked depolarization caused by delivering a pacing pulse in the right ventricular septum occurs rapidly in the right side of the septum 12 and is conducted later to the left ventricular myocardium, similar to the condition of LBB block. As the pacing tip electrode 32 is advanced further into the inter-ventricular septum, as shown by diagram 201c, the characteristic "W" shape of the V1 ECG signal corresponding to LBB block disappears and is replaced by a cardiac electrical event evoked response QRS signal 223 (in column 206) having a relatively narrower negative polarity waveform.

When the pacing tip electrode 32 is advanced further into the left ventricular septum, proximate to the left septal border 13 as shown by diagram 201d, the evoked response signal 224 in the V1 ECG signal due to capture of the LBB may characteristically include a relatively narrow negative peak followed by a relatively narrow positive peak. This morphology of a narrow negative peak followed by a narrow positive peak is similar to the ECG morphology expected in a patient having RBB block and is therefore a "RBB block-like signal" that occurs when LBB pacing capture occurs without RBB capture. Processor 52 may be configured to perform morphology waveform analysis of the ECG evoked response waveforms following a delivered pacing pulse 232 for detecting this transition from a "W" shaped negative polarity evoked response waveform 222 to a single-peaked negative polarity evoked response QRS waveform 223 to the narrow negative polarity followed by narrow positive polarity QRS waveform 224 (RBB block-like signal) during advancement of the pacing tip electrode 32 through the ventricular septum 12 while delivering pacing pulses 232 via the pacing tip electrode (cathode) 32 and a selected return anode electrode, which may be a catheter or delivery tool electrode or a surface (cutaneous) electrode.

The evoked response morphology in the V1 ECG signal following an LBB pacing pulse that captures the LBB may resemble an RBB block ECG signal morphology because the RBB is not captured by the pacing pulse. An RBB block-like signal, also referred to herein as an "RBB block pattern," may exhibit an rSR morphology or QR or S wave morphology. As such, an overall evoked response waveform morphology analysis may be performed by processor 52 to determine an LBB signal when an RBB block-like signal morphology in the V1 (or V2) ECG signal follows a pacing pulse delivered by the pacing tip electrode 32. Morphology analysis may include time domain amplitude analysis, wavelet transform analysis, or frequency domain analysis. Examples of various V1 ECG signal features that may be determined and tracked during advancement of the pacing tip electrode 32 across the ventricular septum 12 while delivering pacing pulses are described below in conjunction with FIG. 7.

Other ECG signals may be analyzed by processor 52 in addition to or instead of the V1 ECG signal. Processor 52 may analyze an ECG signal, e.g., the V5 and/or V6 ECG signals, to determine the LV activation time 244 from pacing pulse 232 to a maximum peak amplitude of the evoked response signal following the pacing pulse. LV activation time 244 may be determined as pacing tip electrode 32 is advanced across the septum 12. The LV activation time 244 when the pacing tip electrode 32 is in the right portion of septum 12 (column 204) is relatively long and undergoes a decrease to a relatively rapid LV activation time 254 as the pacing tip electrode 32 is advanced into the left portion of septum 12 (column 208). The LV activation time from pacing pulse 232 to a maximum peak amplitude of the evoked response QRS signal may decrease when the pacing tip electrode 32 is in the left portion of the septum 12 because the LBB is captured early after the pacing pulse. The myocardial depolarization resulting from the conducted LBB capture is conducted to the RV relatively later, after LBB capture, resulting in a longer RV activation time 255 observed in the V2 ECG signal compared to the LV activation time 254. The longer RV activation time due to later conduction to the RV myocardium is also observed as a later peak 253 in the V1 or V2 ECG signals compared to the maximum peak of the V5 or V6 ECG signals corresponding to earlier LV activation time 254. The LV activation time 254 from the pacing pulse 232 to the maximum peak of the post-pace evoked response signal is relatively short, e.g., 70 to 90 ms, in the V5 or V6 ECG signal (more proximate the LV), and the RV activation time 255 is relatively longer or delayed, e.g., greater than 90 ms, in the V1 or V2 ECG signals (more proximate the RV). In some examples, the RV activation time 255 from the pacing pulse 232 to the maximum peak of the evoked response signal in the V1 and/or V2 signal may be compared to the LV activation time 254 in the V5 and/or V6 signal. An ECG signal having a relatively short LV activation time in the V5 or V6 ECG signal caused by LBB capture compared to relatively longer RV activation time 255 in the V1 or V2 ECG signal caused by delayed activation of the RV following LBB capture may be determined by processor 52 as an LBB signal indicative of a left septal location of the pacing tip electrode 32.

In other examples, a relative shortening of the LV activation time in the V5 and/or V6 ECG signals, as represented by the change in LV activation time 244 when tip electrode 32 is in the right portion of septum 12 to LV activation time 254 as the tip electrode 32 is advanced from the right to the left portion of the septum 12, may be detected by processor 52 as an LBB signal. Additionally or alternatively, a relative increase in the RV activation time 245 (from the pacing pulse to the absolute maximum QRS peak 243) to RV activation time 255 (from the pacing pulse to the absolute maximum QRS peak 253) in the V1 or V2 ECG signals as the pacing tip electrode 32/132 is advanced may be detected by processor 52 as an LBB signal. A change from a shorter RV activation time 245 to a longer RV activation time 255 determined from the V1 or V2 ECG signals, a change from a longer LV activation time 244 to a shorter LV activation time 254 determined from the V5 or V6 ECG signals, and/or a change from a positive difference between the LV activation time 244 less the RV activation time 245 (column 204) to a negative difference between LV activation time 254 less RV activation time 255 (column 208) may be determined by processor 52 as a change to an LBB signal evidencing proximity of the pacing tip electrode 32 to the LBB.

As shown in FIG. 6, the evoked response waveforms 242 during pacing in the left portion of the septum 12 in each of the V2 through V6 ECG signals (column 208) undergo changes in polarity, signal width, maximum positive peak amplitude, activation time interval from the pacing pulse to the maximum positive peak, and/or other morphological changes compared to the respective evoked response QRS waveforms 240 during pacing in the right portion of the septum 12 (column 204). For example, the V2 ECG signal changes from a relatively wide, negative polarity signal, which may have the "W" shaped morphology, when the pacing tip electrode 32 is in the right portion of the septum 12 to a "notched" signal (resembling an "M" shaped morphology), having two positive peaks separated by a negative peak, when the pacing tip electrode 32 is in the left portion of the septum 12. Processor 52 may be configured to detect this "notched" morphology from the V2 ECG signal (in column 208) as a RBB block-like signal that is evidence of pacing and capturing the LBB, resulting in early capture and activation of the LBB followed by conduction to the RV. Morphological changes are also observed in ECG leads I, II, III, aVR, aVL and aVF between columns 204 and 208 corresponding to pacing in the right portion and left portion of the septum 12, respectively. As such, processor 52 may be configured to receive raw cardiac electrical signals from all or a selected combination of 12-lead surface electrodes for analyzing and determining features from one or more of the ECG signals to detect an LBB signal corresponding to pacing and capture at an LBB pacing site, which may resemble an RBB block-like ECG signal.

Detection of an LBB signal indicative of the pacing tip electrode 32 being in an LBB pacing position may be made by processor 52 based on detecting a change in a post-pace evoked response QRS signal in one selected ECG signal, e.g., either V1 or V6, that resembles an LBB block QRS signal (indicating pacing in the right portion of the septum) to a post-pace evoked response signal that resembles an RBB block QRS signal (indicating pacing in the left portion of the septum). For example, the wide evoked response QRS width 246 (characteristic of LBB block) in the ECG V5 or V6 signals during pacing in the right septum decreases to a relatively narrow evoked response QRS width 256 during pacing in the left septum indicating LBB block correction and LBB capture. Additionally or alternatively, processor 52 may perform a comparative analysis between two or more different ECG signals, e.g., comparing the V1 or V2 ECG signals to the V5 or V6 ECG signals to detect differences in the RV and LV activation times or other evoked response signal features that are indicative of a RBB block-like signal in the V1 or V2 ECG signals and/or correction of LBB block as evidenced by a narrow evoked response QRS width 256 and/or early LV activation time 254 in the V5 or V6 ECG signals. Example methods of LBB signal detection by processor 52 are further described below in conjunction with FIG. 10.

In still other examples, the EGM signal 230 may be analyzed during pacing pulse delivery using the pacing tip electrode 32 as a pacing cathode electrode for detecting an LBB signal during advancement in septum 12. Example techniques for detecting an LBB signal from EGM signal 230 during pacing pulse delivery are described below in conjunction with FIG. 8. When processor 52 determines that the LBB signal detection criteria based on one or any combination of ECG signal and/or the EGM signal analysis during pacing pulse delivery, processor 52 may generate a user feedback signal indicating that LBB pacing placement of the pacing tip electrode 32 is achieved.

Processor 52 may additionally analyze the EGM signal 230 during an intrinsic ventricular rhythm (non-paced) for detecting the LBB potential signal 234 and/or an injury current based on the amplitude difference 235 as described above for determining an LBB signal and confirming LBB pacing site placement of the pacing tip electrode 32. In other examples, processor 52 may determine an intrinsic LV activation time 238 from the EGM signal 230 by detecting the LBB potential signal 234 and the maximum peak of the intrinsic QRS signal. When the intrinsic LV activation time 238 is less than a threshold interval (or within a threshold activation time interval range), the processor 52 may detect an LBB signal indicative of left septal position of the pacing tip electrode 32. Techniques for determining an LBB pacing location of the pacing tip electrode 32 using the EGM signal 230 may be used in a patient that does not have LBB block.

The various differences in the pacing evoked QRS signals of the V1/V2 ECG signals when the RBB is captured and the LBB is not captured (e.g., as shown in column 204) compared to when the RBB is not captured and the LBB is captured (e.g., as shown in column 208) may be detected by processor 52 for distinguishing between RBB capture and non-capture and/or for confirming LBB capture. The various differences in the pacing evoked QRS signals of the V5/V6 ECG signals when only the LBB is captured (e.g., as shown in column 208) compared to when the LBB is not captured but the RBB is captured (e.g., as shown in column 204) may be detected by processor 52 for distinguishing between LBB capture and non-capture and/or for confirming RBB capture. LBB capture and/or RBB capture may be confirmed, e.g., during daily capture monitoring by pacemaker control circuit 80 based on analysis of the post-pace EGM signal by control circuit 80. A pacing capture threshold test may be performed on a scheduled basis, e.g., daily, hourly or other frequency, by varying the pacing pulse output to determine, by control circuit 80, the minimum pacing pulse output that results in evidence of LBB capture and/or RBB capture in the EGM signal 230 according to any of the examples described herein.

As described below, e.g., in conjunction with FIG. 16, external device processor 52 may be configured to analyze ECG signals sensed while bundle branch pacing is being delivered according to different pacing electrode configurations and/or pacing pulse output settings to detect capture of the RBB and/or LBB, determine pacing capture threshold(s), and determine an associated improvement in ventricular electrical synchrony, e.g., based on the QRS width, difference between LV and RV activation times (also referred to herein as the "interventricular activation time difference"). Determination of RBB-only capture, LBB-only capture, BBB capture (capture of both of the RBB and LBB) and an associated ECG signal metric indicative of ventricular electrical synchrony may be used for determining an optimal bundle branch pacing electrode configuration and/or pacing pulse output settings as described in conjunction with FIG. 16.

Figure 7:
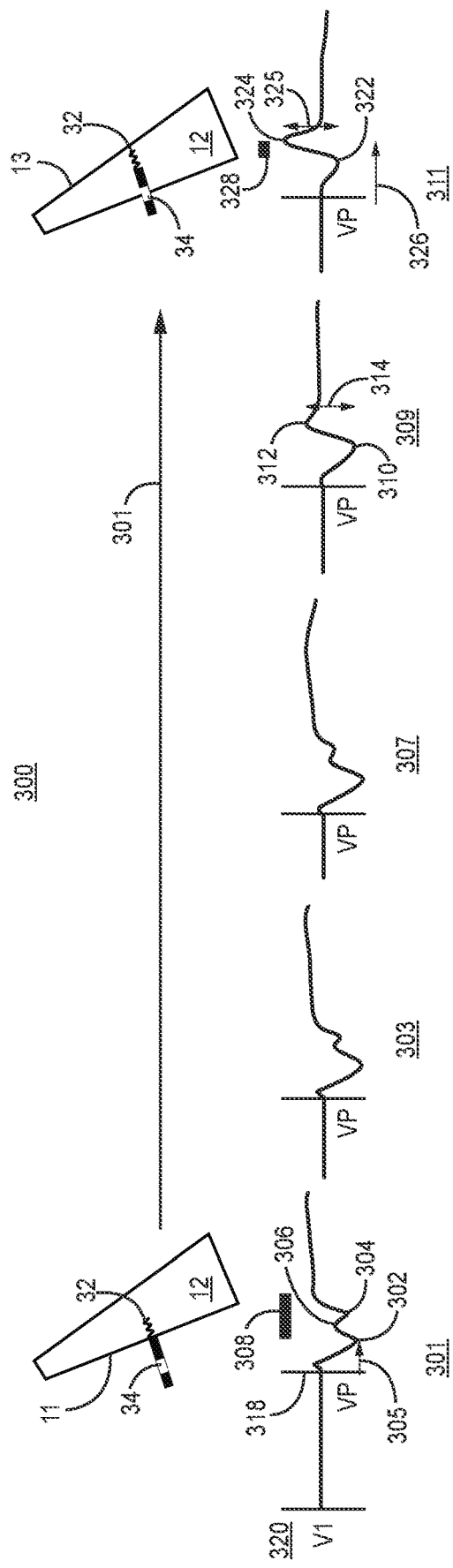
FIG. 7 is a diagram of a V1 ECG signal during advancement of a pacing tip electrode from a position proximate the right border of ventricular septum to a position proximate the left border of septum.

FIG. 7 is a diagram 300 of a V1 ECG signal 320 during advancement of the pacing tip electrode 32 from a position proximate the right border 11 of ventricular septum 12 to a position proximate the left border 13 of septum 12 (as indicated by arrow 301). Example evoked response QRS waveforms 301, 303, 307, 309 and 311 as they may appear in the V1 ECG signal 320 are shown as the pacing tip electrode 32 progresses from an initial position in the right portion of the septum 12 (waveform 301) to a final position in the left portion of the septum 12 (waveform 311) with intermediate septal positions corresponding to evoked response QRS waveforms 303, 307 and 309.

As observed in the example of FIG. 7, the evoked response QRS waveform 301 in the V1 signal 320 exhibits a characteristic "W" shape, with two negative peaks 302 and 304 and intervening inflection point 306, when the pacing tip electrode 32 is in the right portion of the septum 12. External device processor 52 may be configured to determine evoked response QRS waveform features as the pacing tip electrode 32 is advanced through the septum 12 for detecting the transition from the characteristic W-shaped, relatively wide, negative polarity waveform 301 to a loss of the "W" shape in the single, relatively wide negative peak of intermediate evoked response QRS waveform 309, and subsequently to the narrow negative peak followed by the narrow positive peak evoked response QRS waveform 311 when the pacing tip electrode 32 is positioned in the left portion of the septum 12 for LBB pacing. For instance, the absolute value of the minimum amplitude of negative peak 302 in waveform 301 is seen to progressively decrease in evoked response QRS waveforms 303, 307 and 309 to minimum peak amplitude 310 and to the lowest absolute value of the minimum peak amplitude 322 in QRS waveform 311, corresponding to an LBB pacing location of the pacing tip electrode 32. External device processor 52 may track the decrease in the absolute value of the negative peak amplitude of the post-pace QRS signal as the pacing tip electrode 32 is advanced and adjust a user feedback signal generated as a visual or audible representation of the pacing electrode advancement as the negative peak amplitude 302 decreases toward a minimum negative peak amplitude 322.

For example, the progression of a progress bar or wheel and/or the frequency of a flashing LED and/or audible beep may be adjusted as the negative peak amplitude of the evoked QRS signal decreases to indicate that the pacing tip electrode 32 is approaching the LBB pacing site. In some examples, the frequency of a user feedback flashing LED or audible beep is increased to indicate that the pacing tip electrode 32 is getting closer and closer to the LBB pacing site. In other examples, the frequency may be decreased to indicate to a user to advance the pacing tip electrode 32 more slowly, e.g., by slower rotation of a helical pacing tip electrode, as the LBB pacing site is approached to avoid perforation of the left border 13 of the septum 12.

Other features that may be determined by external device processor 52 from the V1 ECG signal 320 during pacing tip electrode advancement include the time interval from a delivered pacing pulse 318 to the maximum absolute peak amplitude, e.g., time intervals 305 and 326; the positive peak amplitude, e.g., amplitude 312 and 324; the peak-to-peak width between the negative minimum and positive maximum peaks, e.g., time intervals 308 and 328; the peak-to-peak amplitude difference, e.g., differences 314 and 325 shown as the positive peak amplitude minus negative peak amplitude; and the ratio of the positive peak amplitude to the negative peak amplitude of the pacing-evoked QRS signal.

As observed in diagram 300, the RV activation time 326 from the pacing pulse 318 to the absolute maximum peak 324 (a positive peak) in evoked response QRS waveform 311 is increased compared to the RV activation time 305 from the pacing pulse 318 to the absolute maximum peak (a negative peak) 302 in evoked response QRS waveform 301. The evoked response positive peak amplitude 324, peak-to-peak amplitude difference 325 and positive peak amplitude to negative peak amplitude ratio all increase as the pacing tip electrode 32 delivering the pacing pulses is advanced from right to left through the septum 12. The peak-to-peak width 328 decreases compared to peak-to-peak width 308 as the pacing tip electrode 32 is advanced from right to left through the septum 12. One or more of these features or changes in the general morphology waveform from a negative polarity, "W" shaped waveform 301 to the positive, narrow peak waveform 311 may be determined by processor 52 during pacing tip electrode advancement. External device processor 52 may generate an output of these QRS waveforms for display to a user on display unit 54 for observation during the implant procedure.

A user feedback signal may be adjusted by processor 52 as one or more of these determined features change during pacing electrode advancement. In some examples, processor 52 controls the user feedback signal to be adjusted in proportion to the change detected in one or more of the determined evoked response signal features. For example, a rapid change in the positive peak amplitude to negative peak amplitude ratio (or other determined feature) is indicated to the user by a rapidly blinking LED, moving progress bar or wheel and/or beeping tone. As the user slows advancement of the tip electrode 32, the user feedback signal may be adjusted more slowly in proportion to a slower change in the positive peak amplitude to negative peak amplitude ratio or other determined ECG V1 QRS signal feature.

The pacing evoked QRS signal waveform 301 during pacing in the area of the RBB is representative of capture of the RBB without capture of the LBB. The pacing evoked QRS signal waveform 311 is representative of capture of the LBB without capture of the RBB. External device processor 52 may be configured to determine one or more features of the QRS signal in the post-pace ECG signal for determining RBB-only capture, LBB-only capture and BBB capture for verifying capture during pacing or during a capture threshold search, e.g., as described below in conjunction with FIG. 16. The features of QRS signal 301 and QRS signal 311 described above may be determined for detecting capture of the RBB and the LBB, respectively.

The changes in the post-pace ECG signal 320 (or any of the ECG signals shown in FIG. 6) corresponding to a change from RBB capture to LBB capture may be used for confirming capture of the respective bundle branch and for establishing morphology features in a simultaneously sensed EGM signal during the known capture (or loss of capture) conditions. Pacemaker control circuit 80 may use the post-pace EGM morphology features established during advancement of pacing electrode 32 when, based on ECG signal analysis, RBB capture is verified and subsequent RBB loss of capture is verified for subsequent EGM-based capture monitoring and capture threshold tests, e.g., during bundle branch pacing therapy delivery. Pacemaker control circuit 80 may use EGM morphology features established when LBB loss of capture and LBB capture is verified based on ECG signal analysis during advancement of pacing electrode 32 for use in subsequent capture monitoring and capture threshold testing performed by pacemaker control circuit 80 during bundle branch pacing therapy.

Figure 8:
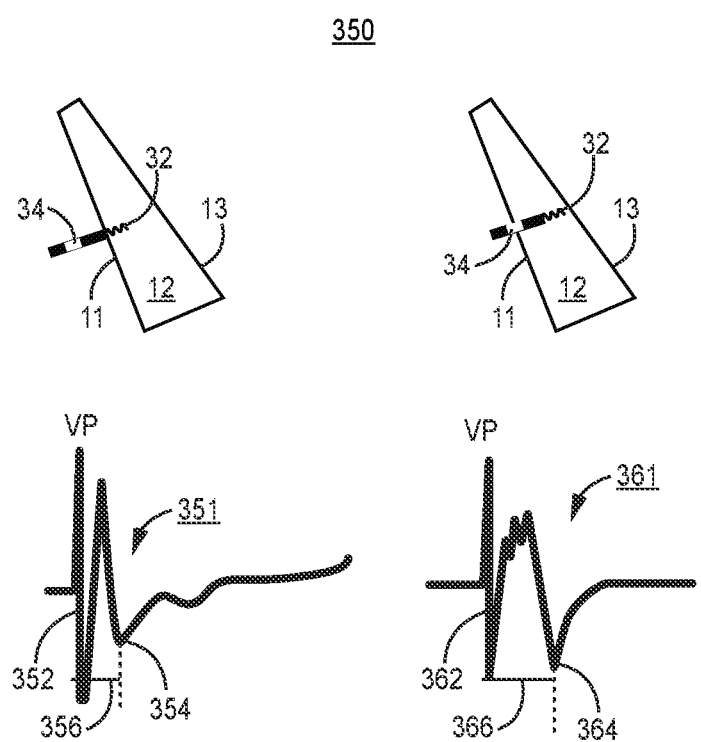
FIG. 8 is a diagram of evoked response QRS signals of an EGM signal acquired using a pacing tip electrode and a selected return anode electrode during pacing pulse delivery via the pacing tip electrode.

FIG. 8 is a diagram 350 of evoked response QRS signals 351 and 361 of an EGM signal acquired using the pacing tip electrode 32 and a selected return anode electrode during pacing pulse delivery via the pacing tip electrode 32. It is to be understood that techniques described with reference to the lead-based pacing tip electrode 32 for determining an LBB signal following a pacing pulse (or during an intrinsic ventricular rhythm) may be used in conjunction with a housing-based electrode, e.g., electrode 132 of pacemaker 114, instead of a lead-based electrode 32. The evoked response QRS signals 351 and 361 may be received via electrodes 32 and 34 of lead 18, for example, following delivery of a pacing pulse 352 and 362, respectively, using pacing tip electrode 32 as the cathode and ring electrode 34 as the anode. The EGM signal may be obtained by coupling electrical connectors to the proximal lead connector. Alternatively, a delivery tool or catheter-based return anode or a cutaneous, surface electrode may be used in conjunction with the cathode pacing tip electrode 32. External device processor 52 may be configured to determine one or more features of the evoked response QRS signal 351, 361 as the pacing tip electrode 32 is advanced from right to left through the ventricular septum 12. The overall morphology of the evoked response QRS signals 351, 361 may be determined and compared to morphology criteria for detecting an LBB signal indicative of an LBB pacing location of tip electrode 32. The overall morphology may be determined using a wavelet transform or other morphology waveform analysis technique. Additionally or alternatively, one or more features of the evoked response QRS signals 351, 361 may be determined, such as a maximum peak amplitude, minimum peak amplitude, peak-to-peak amplitude, peak-to-peak width (as a time interval), pacing pulse to peak time interval, maximum positive-going slope, maximum negative-going slope, number of peaks, number of inflection points, polarity of peaks, etc. Changes in selected features of the EGM signal may be monitored by external device processor 52 (or pacemaker control circuit 80) to detect a change from evoked response signal 351 to evoked response signal 361 as the pacing tip electrode 32 is advanced.

To illustrate, processor 52 may be configured to detect the minimum peaks 354 and 364 of respective evoked response waveforms 351 and 361. Processor 52 may determine a time interval 356 from pacing pulse 352 to minimum negative peak 354 when the pacing tip electrode 32 is first advanced within a right portion of septum 12. The time interval 356 may be determined as pacing pulses are delivered while the pacing tip electrode 32 is advanced through septum 12. As observed in FIG. 8, the time interval 366 to minimum negative peak 364 when the pacing tip electrode 32 is positioned in the left portion of septum 12 is increased compared to time interval 356 when the pacing tip electrode 32 is in the right portion of the septum 12. When the time interval 366 is determined to be greater than a threshold time interval, processor 52 may detect the evoked response waveform 361 as an LBB signal indicative of placement of the pacing tip electrode 32 at an LBB pacing site and evidence of capture of the LBB. Processor 52 may adjust a user feedback signal as increases in the time interval from the pacing pulse delivery to the minimum negative peak 364 are detected and/or changes in another fiducial point or morphology metric of the evoked response signals 351, 361 are detected. In response to detecting the LBB signal based on morphology analysis of the EGM signal during pacing, processor 52 may generate a user feedback signal indicating LBB pacing site placement of the pacing tip electrode 32. Morphology features of evoked response signal 351 corresponding to RBB capture and morphology features of evoked response signal 361 corresponding to LBB capture may be determined by external device processor 52 or pacemaker control circuit 80 and used to establish RBB capture criteria and LBB capture criteria, respectively, for use by control circuit 80 during subsequent capture monitoring and/or pacing capture threshold searches performed during bundle branch pacing therapy.

Figure 9:
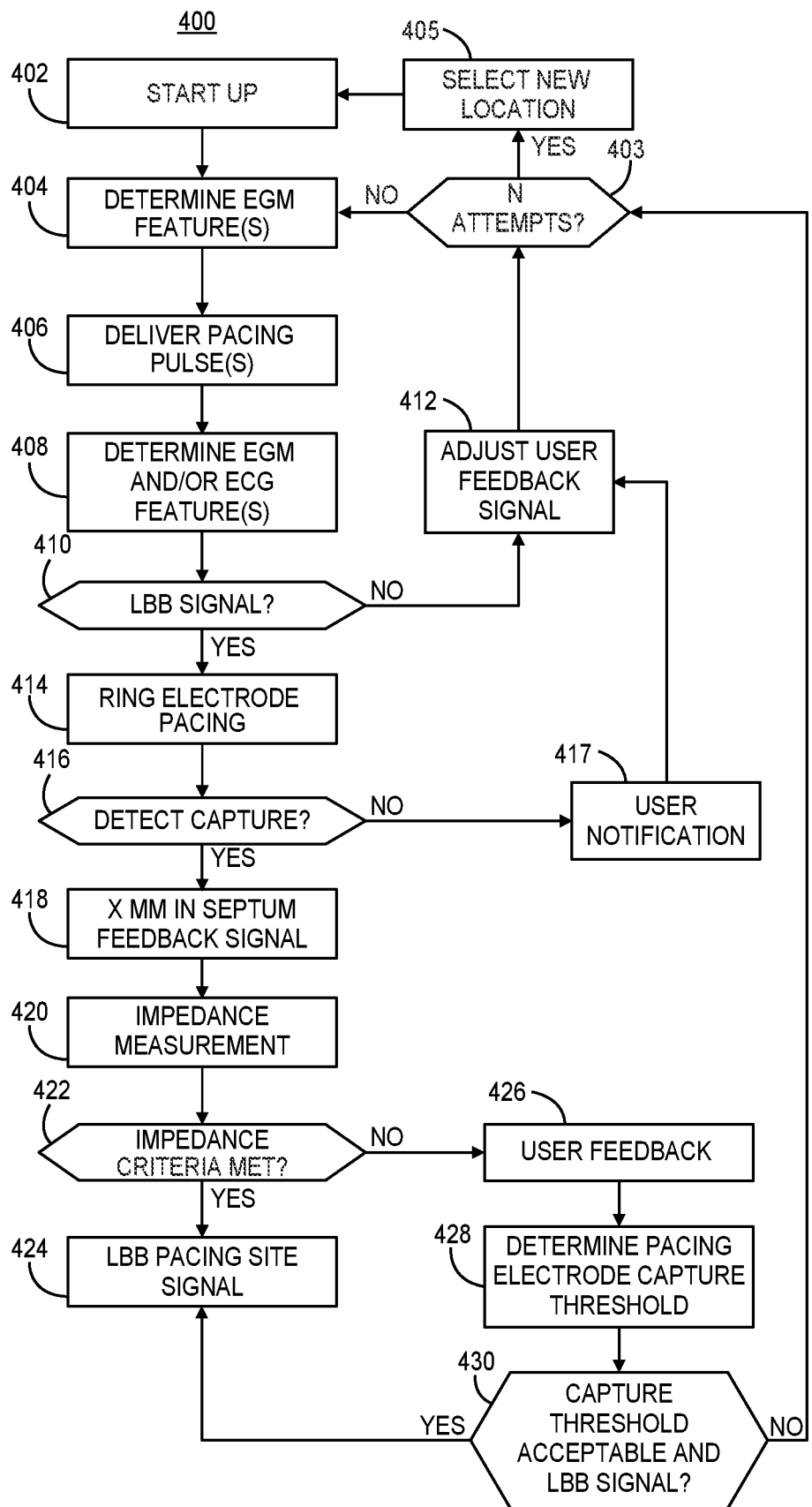
FIG. 9 is a flow chart of a method for detecting placement of a pacing electrode at a left bundle branch (LBB) pacing site according to one example.

FIG. 9 is a flow chart 400 of a method for detecting placement of a pacing electrode at an LBB pacing site according to another example. Upon starting up, at block 402, external device processor 52 may generate a user prompt displayed on display unit 54 instructing the user to begin advancing the pacing tip electrode 32. The impedance measurement unit 62 may determine the electrical impedance between the pacing tip electrode 32 and a selected anode electrode and detect an increase in impedance due to the pacing tip electrode 32 coming into contact with and/or entry into the right septal wall from within the RV blood pool. In other examples, processor 52 may detect an injury current in the EGM signal received via the pacing tip electrode 32 indicating that the pacing tip electrode 32 has entered the septum. A user notification may be generated by processor 52 that indicates that the pacing tip electrode 32 is positioned for advancement into the septum. The user notification may instruct the user to advance the tip electrode 32 by a predetermined number of rotations, e.g., 2 or more clockwise rotations of the proximal lead connector 20 of lead 18 (FIG. 1) or rotations of the leadless pacemaker housing 115 (FIG. 3).

At block 404, processor 52 may determine EGM signal features during the intrinsic heart rhythm. Processor 52 may determine EGM signal features during the intrinsic rhythm after a predetermined number of clockwise rotations have been performed and confirmed by a user input received via user interface 56. In other examples, processor 52 may be sensing the EGM signal and determining EGM signal features on a beat-by-beat basis, e.g., as the user is advancing the pacing tip electrode 32. At block 406, processor 52 may control pulse generator 60 to generate one or more pacing pulses that are delivered via the pacing tip electrode 32 and a return anode electrode, e.g., a cutaneous or subcutaneous return anode electrode used during testing, a return anode that may be included on the delivery catheter or tool, or a proximal ring electrode carried by a pacing lead or intracardiac pacemaker, e.g., proximal ring electrode 34 or 134 of FIGS. 2A and 3, respectively. One or more features of the evoked response waveform are determined at block 408 from at least one ECG signal and/or the EGM signal. Any of the example features described above in conjunction with FIGS. 6-8 may be determined at block 408.

At block 410, processor 52 determines whether the determined features during the intrinsic and/or paced rhythm meet LBB signal criteria indicative of an LBB pacing position of tip electrode 32. Example criteria may include detection of the intrinsic LBB potential signal, an injury current based on elevated baseline amplitude after the LBB potential signal, the LV intrinsic activation time between the LBB potential signal and QRS maximum peak being within an LBB signal range, LV paced activation time from a pacing pulse to the evoked response QRS peak being within an LBB signal range, and/or any of the changes described above in the ECG signals and/or EGM signals that occur in the pacing-induced evoked response as the pacing tip electrode 32 is advanced from the right portion to the left portion of the septum 12.

In one example, processor 52 determines that LBB signal criteria are met at block 410 when at least two out of the following five criteria are satisfied: 1) detect a post-pace V1 or V2 ECG signal that resembles RBB block, e.g., by detecting a delayed evoked response peak in V1 ECG signal (RV activation time) compared to the V5 or V6 LV activation time as described above or detect a notched evoked response in the V2 ECG signal as described above; 2) detect a short post-pace LV activation time, e.g., less than 100 milliseconds or between 70 and 90 milliseconds in the V5 or V6 ECG signal; 3) detect the LBB potential signal from the EGM signal during an intrinsic ventricular rhythm; 4) detect correction of an LBB block signal waveform in a patient that has LBB block, e.g., by detecting a narrow QRS width 256 (see column 208, FIG. 6) of the post-pace evoked response in the V5 or V6 ECG signal, which may be detected as a decrease from the evoked response QRS width 246 after initially entering the septum (column 204, FIG. 6) and 5) detect a premature ventricular contraction (PVC) that results in a QRS waveform that is a RBB block-like signal.

During pacing electrode insertion, mechanical stretching of the cardiac cells can induce PVCs at the site of the pacing tip electrode 32. When this occurs in the left portion of the septum near the LBB, activation in the left septum due to mechanical stretching may cause a QRS waveform that appears similar to a RBB block signal since the RV is electrically activated later than the LV. Processor 52 may monitor RR intervals (time interval between two consecutively detected R-wave threshold crossings). When a short RR interval is detected that is less than a PVC interval threshold (e.g., less than 500 ms), the V1/V2 ECG signals and/or the V5/V6 ECG signals may be analyzed to determine if an RBB block-like signal or an LBB block-like signal is detected. Detection of an RBB block-like signal following a PVC may be used toward satisfying LBB signal detection criteria for confirming an LBB pacing site location of the pacing tip electrode 32. When at least two out of five of the above-listed criteria are satisfied at block 410, an LBB signal is detected by processor 52 in some examples.

If the LBB signal criteria are not met at block 410, as determined by processor 52 based on analysis of the intrinsic EGM signal and/or pacing-induced evoked response signals of one or more ECG signals and/or the EGM signal, processor 52 may generate or adjust a user feedback signal at block 412. The user feedback signal may be an implant progress indicator generated according to the number of turns prompted to the user since start up at block 402 in some examples. For instance, the total number of turns prompted to the user in user feedback signals generated by processor 52 may be counted by processor 52 (with or without user confirmation via user interface 56), and the user feedback signal may prompt the user to apply up to a maximum number of turns based on an expected ventricular septum thickness and length of tip electrode 32. In other examples, the user feedback signal is an implant progress indicator based on the EGM and/or ECG signal features determined at blocks 404 and/or 408. For example, the user feedback signal may be adjusted to indicate a progression that is within the right portion of the septum 12, e.g., based on detection of a characteristic "W" shaped waveform in the V1 ECG signal or an LBB block-like signal in the ECG signal following a pacing pulse. The user feedback signal may be adjusted to indicate a progression that is within a mid-portion of the septum 12 based on the morphology or characteristic features of the evoked response QRS waveforms being an intermediate form of the ECG and/or EGM signals when the pacing tip electrode 32 is between the right and left portions of the septum as described in conjunction with FIGS. 6 and 7.

Based on the user feedback signal generated by processor 52, the user may be prompted to advance the pacing tip electrode 32 further, and processor 52 may repeat the EGM and/or ECG signal analysis of blocks 404 through 410. When processor 52 determines that LBB signal criteria are met at block 410, external device 50 may execute additional tests for verifying an acceptable position of the pacing tip electrode 32 for LBB pacing.

In one example, processor 52 may control pulse generator 54 to perform a pacing capture test by generating and delivering one or more pacing pulses at block 414 via a proximal electrode, e.g., ring electrode 34 of lead 18, selected as the cathode electrode and the pacing tip electrode 32 or a cutaneous or subcutaneous electrode selected as the return anode. If RBB capture is detected at block 416 following a pacing pulse delivered by the proximal electrode 34, e.g., based on an evoked response QRS signal detected within a capture window following the pacing pulse corresponding to RBB capture, a user feedback notification may be generated at block 418. Capture during pacing from the proximal ring electrode 34 indicates that the proximal ring electrode 34 is in contact with the septum such that at least the length of the distal portion of lead 18 extending from pacing tip electrode 32 to ring electrode 34 is within the septum 12. If the proximal ring electrode 34 and pacing tip electrode 32 are known to be 10 millimeters (mm) apart, as an example, processor 52 may generate a user notification that the pacing tip electrode 32 has been advanced at least 10 mm into the septum at block 418.

In other examples, the pacing tip electrode 32 may be selected as the cathode and the ring electrode 34 may be selected as the anode during a RBB capture test at blocks 414 and 416. The pacing pulse output may be increased to a relatively high or maximum output, for example, at block 414 to achieve anodal capture at the ring electrode 34 of lead 18. In this case, anodal capture of the RBB, as evidenced by cardiac signal morphology features corresponding to RBB capture (and in this case BBB capture), is an indication that the ring electrode 34 is against or within the right portion of the septum.

If capture is not detected following a pacing pulse delivered by using the proximal ring electrode 34, processor 52 may generate a user notification (at block 417) for display on display unit 54 that the pacing tip electrode 32 is less than 10 mm (as an example) within the septum. Processor 52 may adjust the user feedback signal indicating pacing electrode progression within the septum at block 412. Processor 52 may prompt the user to advance the pacing tip electrode 32 with caution, e.g., by slowly advancing at least one more turn. This process of EGM and/or ECG signal analysis during the intrinsic and/or paced rhythm may be repeated at blocks 404-410 to detect an LBB signal and confirm adequate advancement based on pacing capture achieved at the proximal ring electrode 34 (blocks 414 and 416).

In other examples, instead of or in addition to a pacing capture test using proximal ring electrode 34, impedance measurement unit 62 may acquire an impedance signal at block 420 by applying a drive signal to the proximal ring electrode 34 and recording the resulting signal using a recording pair of electrodes, which may be any available pair of electrodes and may include cutaneous or subcutaneous return electrode(s). A decrease in impedance indicating that the proximal ring electrode 34 has moved from the RV blood pool to being in contact with or into the septum 12 may be used to confirm that the pacing tip electrode 32 has been inserted into the septum 12 a distance that is at least equal to the interelectrode spacing.

In some examples, processor 52 may control impedance measurement unit 62 to determine pacing electrode impedance at block 420 to verify that the pacing tip electrode 32 is not over-advanced into the LV chamber. The pacing electrode impedance may be determined by delivering a drive signal using pacing tip electrode 32 and proximal ring electrode 34 (or another return electrode) and determining the resulting impedance, which may be determined as the resulting voltage signal across the recording electrode pair when a known drive current signal is delivered or the ending voltage of a holding capacitor being discharged during a delivered pacing pulse by pulse generator 60. The pacing electrode impedance may be verified to be within an acceptable range at block 422. The acceptable range may be based on an impedance determined while the pacing tip electrode 32 is within the septum 12, e.g., before an LBB signal is detected but after verifying entry into the septum 12, e.g., based on injury current signal. The acceptable range may be greater than an impedance determined when the pacing tip electrode 32 remains in the RV blood pool during the start-up procedure. When the pacing electrode impedance is low at block 422, e.g., less than a threshold impedance or within a threshold range of an RV blood pool baseline impedance, the pacing tip electrode 32 may be over-advanced, perforating into the LV blood pool.

In response to detecting a low impedance corresponding to impedance in a blood pool due to over-advancement, processor 52 may generate a user feedback on display unit 54 at block 426 instructing the user to retract or reverse the rotation of the pacing tip electrode 32. Processor 52 may re-determine the impedance and prompt the user and/or adjust the user feedback signal accordingly until the impedance increases, indicating that the pacing tip electrode 32 is within the septal tissue again.

In some examples, processor 52 may determine the pacing capture threshold at block 428. A capture threshold search may be performed by delivering pacing pulses at multiple pacing pulse amplitudes and/or pacing pulse widths until capture is lost or the minimum pacing pulse output at which at least LBB capture is detected. The pacing pulses may be delivered at a premature pacing interval, e.g., faster than an intrinsic heart rate or at a shortened AV delay, to avoid fusion with the pacing evoked and intrinsic depolarizations (or failure to capture due to the intrinsic depolarization occurring earlier than the pacing pulse). In some examples, capture may be verified by delivering a unipolar pacing pulse via the pacing tip electrode 32 (as the cathode) and a cutaneous or subcutaneous anode electrode or a catheter based anode electrode using a relatively high pacing pulse amplitude and pulse width at block 428 to verify that capture is achieved. In some examples, the proximal ring electrode 34 (or proximal electrode 134 in the case of intracardiac pacemaker 114) may be used as the return anode in a bipolar pacing pair. For example, a unipolar or bipolar pacing pulse of 1 volt amplitude and 0.5 milliseconds (ms) may be delivered. If capture is detected, based on an evoked response QRS signal detection following the pacing pulse, and the LBB signal criteria are still being met at block 430, processor 52 may generate a user feedback signal indicating placement of the tip electrode 32 at an LBB pacing site (block 424). While block 428 is shown to be performed when impedance criteria are not met in the flow of FIG. 9, is to be understood that the LBB pacing capture threshold (or at least LBB capture verification) may be determined at block 428 when impedance criteria are determined to be met at block 422, as well as in examples that do not include an impedance measurement for verifying an LBB pacing site of pacing electrode 32 at blocks 420 and 422.

In some instances, criteria for detecting LBB pacing location of the pacing tip electrode 32 may not be satisfied after several attempts of advancing (and in some cases retracting) the pacing tip electrode 32. When LBB signal and/or capture testing criteria remain unmet after a maximum number of attempts, e.g., three attempts, of adjusting the pacing electrode position after entering the septum (block 403), a user feedback signal may be generated at block 405 to select a new location for the pacing tip electrode 32. The user may retract the pacing tip electrode 32 out of the septum 12 and enter the septum 12 at a new location or angle. Processor 52 may repeat determining the baseline signals and measurements made during the start-up procedure at block 402 as needed.

While analysis of ECG and/or EGM signals during intrinsic and/or pacing pulse delivery, pacing capture testing, and electrode impedance testing are shown in a particular order in FIG. 9, it is contemplated that such testing may be performed in a different order or combination than the particular order and combination shown. Furthermore, one or more of the tests or criteria shown in FIG. 9 may be omitted altogether. Although the LBB signal criteria at block 410, ring electrode capture criteria (and/or ring electrode impedance criteria) at block 414, pacing electrode impedance criteria applied at block 422, and pacing electrode capture threshold determination at block 428 are shown as ordered, sequential operations, it is recognized that these operations may be performed in an alternating or parallel manner. In some cases, over-advancement may occur resulting in a drop in pacing electrode impedance before the LBB signal is detected. As such, it is to be understood that the operations shown in the flow chart 400 and other flow charts presented herein may occur in a different order, repeated in an alternating manner, and/or performed in parallel or concurrently until the criteria for detecting LBB pacing site location of the pacing tip electrode 32 are met, which may include detecting an LBB signal during pacing and/or during an intrinsic rhythm, detecting capture by the proximal ring electrode 34, meeting an impedance requirement, and/or meeting an LBB pacing capture threshold requirement.

Figure 10:
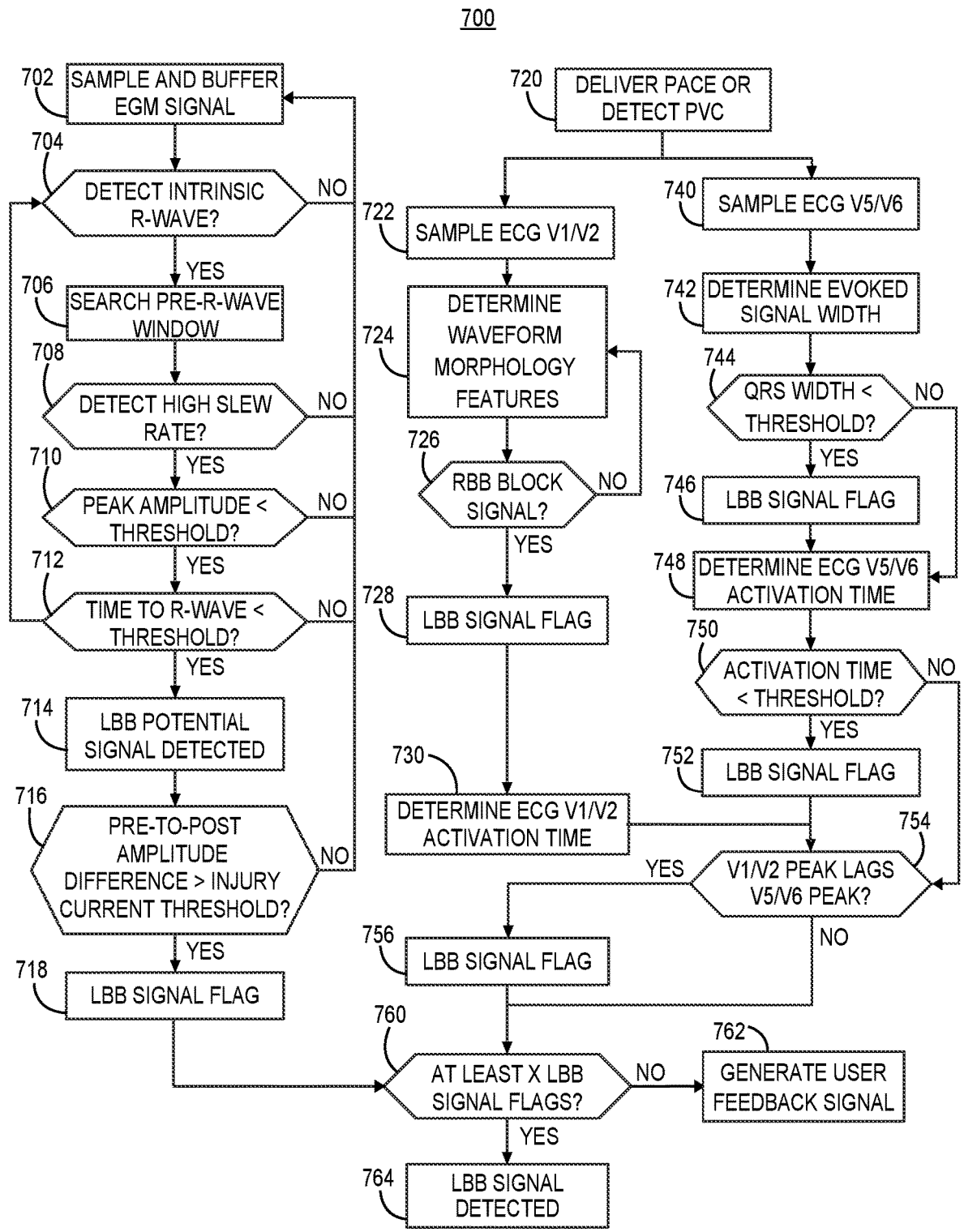
FIG. 10 is a flow chart of a method performed by the external device processor of FIG. 1 for detecting an LBB signal indicative of an LBB pacing location of a pacing electrode according to one example.

FIG. 10 is a flow chart 700 of a method that may be performed by external device processor 52 for detecting an LBB signal according to one example. As described above, an LBB signal may be detected based on one or any combination of the detection of an intrinsic LBB potential signal in the pacing electrode EGM signal, injury current detection, detection of a RBB block signal in a V1 or V2 ECG signal following a pacing pulse or a detected PVC, a wide evoked response signal in the V5 or V6 ECG signal, an early LV activation time in the V5 or V6 ECG signal, and/or detection of a correction of LBB block signal as the pacing electrode is advanced. The process of flow chart 700 is described with reference to external device processor 52 and the lead-based pacing tip electrode 32 for the sake of convenience. It is to be understood that the process of flow chart 700 may be performed in conjunction with the advancement of pacemaker 114 and housing-based pacing electrode 132. Furthermore, it is to be understood that the process of flow chart 700, and other flow charts presented herein, may be performed all or in part by pacemaker control circuit 80 or a combination of external device processor 52 and control circuit 80.

At block 702, the external device processor 52 may sample and buffer the EGM signal sensed using the pacing tip electrode 32 (and any selected anode electrode) as it is advanced through the septum using any available return anode electrode. The EGM signal may be sampled at a relatively high sampling rate, e.g., 1000 Hz to enable detection of the high frequency LBB potential signal. The sampled EGM signal is buffered in external device memory 53 over a sampling window that may be up to 50 ms, as an example. At block 704, external device processor 52 detects an intrinsic R-wave from the EGM signal, e.g., in response to detecting an R-wave sensing threshold crossing by the EGM signal during a ventricular non-paced rhythm.

Upon R-wave detection, processor 52 may analyze the buffered signal over an LBB potential window at block 706, e.g., extending 10 to 40 ms earlier than the sensed R-wave, or encompassing an entirety of the sampling window. In some examples, the sampled signal may be filtered by a high pass filter to reduce or remove low frequency content from the sampled EGM signal to facilitate detection of the high frequency LBB potential signal. Processor 52 may determine a maximum slew rate, slope or peak derivative of the EGM signal during the LBB potential window prior to the R-wave detection and compare the maximum to an LBB potential signal threshold at block 708 for detecting a slew rate or slope that corresponds to an LBB potential signal. If a high slew rate or slope is not detected, an LBB potential signal is not detected, and processor 52 continues to sample and buffer the EGM signal.

When a high slew rate is detected at block 708, processor 52 may determine the maximum peak amplitude during the LBB potential window (set to exclude the QRS signal) and compare the maximum peak amplitude to a maximum LBB potential signal amplitude threshold. The LBB potential signal is a high frequency, low amplitude signal as observed in FIG. 6. If the maximum peak amplitude detected during the LBB potential signal window preceding an intrinsic R-wave is greater than the LBB potential signal threshold amplitude, processor 52 does not detect the LBB potential signal and returns to block 702.

In response to detecting a high slew rate signal with a peak amplitude less than the LBB potential signal, processor 52 may detect the LBB potential signal at block 714. In some examples, processor 52 may verify that the time from the maximum slew rate or the LBB potential signal peak amplitude to the sensed intrinsic R-wave is within an LBB potential threshold interval at block 712. When any one, two or all three of these criteria at block 708, 710 and/or 712 are satisfied, processor 52 may detect the LBB potential signal at block 714 as evidence that the pacing tip electrode 32 is in the left portion of the septum, proximate the LBB. In response to detecting the LBB potential signal, processor 52 may generate an LBB signal flag at block 718 indicating that at least one condition in the EGM signal during an intrinsic ventricular rhythm supports LBB signal detection.

In some examples, processor 52 may additionally verify that an injury current is detected at block 716. When the difference between the EGM signal amplitude post-potential signal and pre-potential signal is greater than a threshold, as determined at block 716, processor 52 may set the LBB signal flag at block 718. As described above in conjunction with FIG. 6, an injury current may be detected in conjunction with the LBB potential signal when the pacing tip electrode 32 is advanced into the left septum.

At block 720, processor 52 may control pulse generator 60 to deliver a pacing pulse using the pacing tip electrode 32, or processor 52 may detect a PVC as the pacing tip electrode 32 is pushed into the left septum. A PVC may be detected by processor 52 by determining a time interval from a pacing pulse or intrinsic R-wave to a consecutively sensed intrinsic R-wave and determining the time interval to be less than a PVC threshold interval. When a pacing pulse is delivered or a PVC is detected, processor 52 may sample the V1 and/or V2 ECG signal at block 722 to determine QRS features at block 724. Features may include an overall waveform morphology, maximum and minimum peak amplitudes and/or slopes and patterns thereof, or other features that enable processor 52 to detect a notched V1 or V2 ECG signal waveform that resembles an RBB block-like signal as the QRS morphology at block 726 according to any of the examples given herein. When a notched waveform, e.g., as shown by the V2 signal in column 208 of FIG. 6 is detected, processor 52 may generate an LBB signal flag at block 728 as evidence that the pacing tip electrode 32 is within the left portion of the septum. In some examples, the morphology feature determination and analysis performed at blocks 724 and 726 may be performed to detect a "W" shaped waveform in the V1 ECG signal following a pacing pulse or PVC. When a "W" shaped morphology is detected as evidence of the pacing tip electrode 32 remaining within the right portion of the septum (e.g., see ECG V1 signal in column 204, FIG. 6), processor 52 does not generate an LBB signal flag. When a "W" shaped morphology is not detected, processor 52 may generate the LBB signal flag at block 728. Any feature or combination of features of the V1 and/or V2 ECG signals that are characteristic of RBB block-like signal morphology may be determined and compared to LBB signal criteria at block 726 for detecting evidence of placement of the pacing tip electrode 32 in the left septum in proximity to the LBB.

At block 740, processor 52 samples the V5 and/or V6 ECG signal following a pacing pulse or detected PVC. At block 742, processor 52 may determine the signal width of an evoked response signal (QRS width) following a pacing pulse delivered by pacing tip electrode 32. When the evoked response QRS signal width is less than an LBB signal threshold width, as determined at block 744, processor 52 may generate an LBB signal flag at block 746. The LBB signal threshold width may be defined based on the evoked response signal width determined when the pacing tip electrode 32 is first advanced into the right portion of the septum. In this way, a relative decrease in the evoked response QRS signal width may be detected. Similarly, other LBB signal criteria referred to herein as being used by processor 52 in detecting an LBB signal may be based on an initial evoked response QRS signal feature that is determined when the pacing tip electrode 32 is first advanced into the right portion of the septum 12 such that a relative change in the evoked response QRS signal corresponding to a change in position from the right portion of the septum to the left portion in the septum is detected by processor 52.

Processor 52 may additionally or alternatively determine an LV activation time at block 748 as the time interval from a delivered pacing pulse to the maximum peak of the evoked response QRS signal (or another fiducial point of the QRS signal) in the V5 and/or V6 signal (e.g., see activation time 254 in the V6 ECG signal of column 208, FIG. 6). The LV activation time may be compared to an LV activation time threshold at block 750. When a short LV activation time is detected, e.g., 70 to 90 ms, in the V5 or V6 ECG signal following a pacing pulse, processor 52 may generate an LBB signal flag at block 752.

Processor 52 may determine the RV activation time in the V1 and/or V2 ECG signal at block 730 and compare the V1/V2 (RV) activation time to the V5/V6 (LV) activation time at block 754. As discussed in conjunction with FIG. 6 above, a relatively longer activation time in the V1/V2 signal compared to the V5/V6 signal is evidence of LBB capture since LV activation occurs quickly and the RV activation is delayed. In the example shown, processor 52 may determine that the V1/V2 signal peak lags the V5/V6 signal peak at block 754, indicating a longer RV activation time than the LV activation time. In response to determining the longer RV activation time than the LV activation time, external processor 52 may set an LBB signal flag at block 756.

At block 760, processor 52 determines when at least a threshold number, e.g., at least two or at least three, LBB signal flags have been generated. The processes for determining whether to set an LBB signal flag at blocks 718, 728, 746, 752, and/or 756 may be performed in any desired sequential and/or parallel processing combinations. When less than a threshold number, X, of LBB signal flags have been generated, processor 52 may generate a user feedback signal 762 to proceed with advancing the pacing tip electrode 32. All or portions of the process of flow chart 700 may be repeated as the pacing tip electrode 32 is advanced or after each predetermined number of turns of pacing tip electrode 32. When the threshold number of LBB signal flags are generated, processor 52 detects an LBB signal at block 764, indicating placement of the pacing tip electrode 32 for LBB pacing. A user feedback signal may be generated at block 170 (of FIG. 5) indicating that LBB pacing placement of tip electrode 32 is achieved, or processor 52 may perform additional confirmation analysis, e.g., by checking the pacing electrode impedance and/or a performing a pacing capture threshold test, e.g., as described in conjunction with FIG. 5 and FIG. 9 above.

When the pacing tip electrode 32 is positioned for LBB pacing, the ring electrode 34 may be positioned for RBB pacing. RBB pacing may be achieved using the ring electrode 34 as a cathode electrode, e.g., in a unipolar pacing electrode vector with pacemaker housing 15 or with the tip electrode 32 selected as the anode. In other examples, RBB pacing may be achieved by anodal capture when the ring electrode 34 is selected as the anode with tip electrode 32 being the cathode in a bipolar pacing electrode vector. In another example, both of the tip electrode 32 and ring electrode 34 may be selected as cathode electrodes with the pacemaker housing 15 used as the return electrode (or another available electrode such as an electrode 94 carried by CS lead 92). The cathode tip electrode 32 and the cathode ring electrode 34 may be selected for dual unipolar BBB pacing with simultaneous LBB and RBB capture. As such, after confirming placement of tip electrode 32 for LBB pacing, external device processor 52 and/or pacemaker processor 148 may analyze cardiac electrical signals (ECG and/or EGM signals) for determining RBB capture, LBB capture, BBB capture and may determine the capture thresholds for use in selecting a pacing electrode configuration and pacing pulse output settings.

Figure 11:
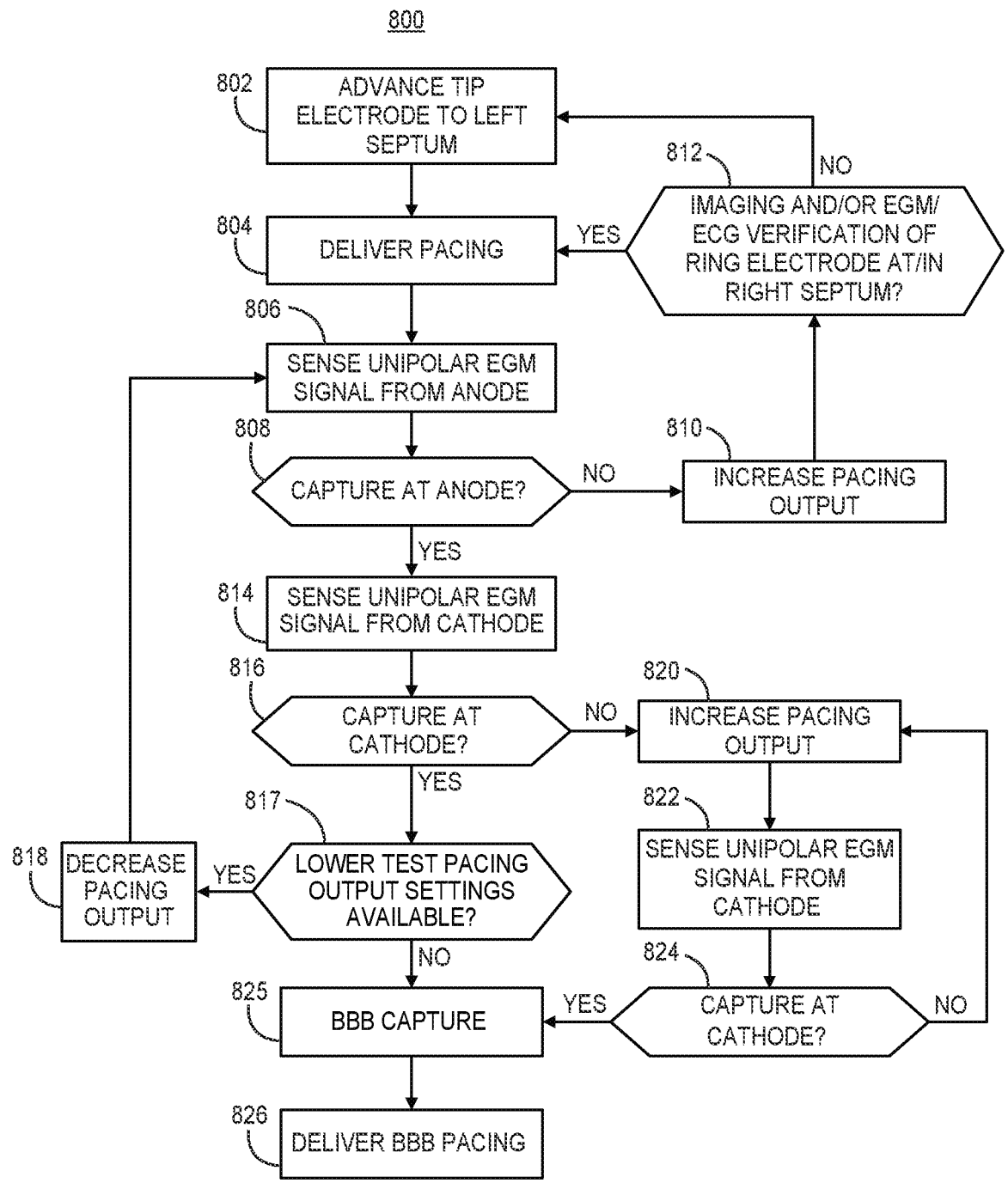
FIG. 11 is a flow chart of a method performed by a medical device for determining a capture threshold for achieving BBB pacing according to one example.

FIG. 11 is a flow chart 800 of a method performed by a medical device for determining a capture threshold for achieving BBB pacing according to one example. LBB pacing is a near-physiological pacing modality, leading to fast left ventricular activation and relatively narrow QRS duration. Accordingly, in some patients LBB-only pacing may improve the ventricular electrical synchrony in a patient experiencing conduction abnormalities without requiring RBB pacing. However, because the LBB pacing pulse excites only the LBB, LBB pacing may result in an ECG signal exhibiting a RBB block-like signal morphology as described above, e.g., in conjunction with FIG. 6, due to the delayed RV activation compared to LV activation. In some instances, LBB capture may cause an interventricular activation delay. To correct or avoid this interventricular activation delay and RBB block-like signal morphology, e.g., as seen in the V1 or V2 ECG signal, BBB pacing may be desired.

Bipolar BBB pacing may be delivered using the pacing tip electrode 32 as the cathode and the ring electrode 34 as the anode at a pacing pulse amplitude and width that results in both cathodal capture of the LBB and anodal capture of the RBB when the ring electrode 34 is against or within the right ventricular septum, in the area or vicinity of the RBB. Alternatively, the tip electrode 32 may be selected as a pacing anode for anodal capture of the LBB and the ring electrode 34 may be selected as the pacing cathode for cathodal capture of the RBB in bipolar BBB pacing. In still other examples, each of the tip electrode 32 and the ring electrode 34 may be selected as cathode electrodes paired with pacemaker housing 15, for example, in a unipolar pacing configuration for BBB pacing using the two unipolar pacing vectors.

In this way, pacing to activate both left and right ventricles is achieved by capturing both the left and right bundle branches in unison, referred to herein a bilateral bundle branch (BBB) pacing and sometimes referred to as dual bundle branch pacing. Because the capture thresholds of the RBB and the LBB can be different due to different relative locations of the tip electrode 32 to the LBB and the ring electrode 34 to the RBB, differences in anodal capture and cathodal capture thresholds, and different pacing electrode characteristics, techniques are disclosed herein for providing a device and method for determining the capture threshold for achieving BBB pacing. In some examples, the optimal polarity of the electrodes needed for achieving effective and energy efficient BBB pacing may be determined. Thus, the techniques disclosed herein provide a device and method to determine BBB pacing capture threshold and control pacing output control parameters for delivering and maintaining effective BBB pacing, e.g., through capture monitoring and adjustments to pacing output control parameters as needed according to capture threshold tests. The pacing output control parameters may include but are not limited to pulse amplitude, pulse width, pulse polarity (selection of anode and cathode in a bipolar pair) and/or selection of unipolar or bipolar electrode combinations.

Signal processing and analysis operations of flow chart 800 for determining BBB pacing capture and adjusting the pacing output accordingly may be performed by control circuit 80 of pacemaker 14. In other examples, however, the signal processing and analysis operations of flow chart 800 may be performed by the processor 52 of external device 50. External device processor 52 may receive raw cardiac electrical signals by being coupled to lead 18 for sensing EGM signals, or external device processor 52 may receive sensed EGM signals from pacemaker 14 via telemetry communication. External device processor 52 may additionally or alternatively receive ECG signals using ECG electrodes 40 as shown in FIG. 1 for determining BBB pacing capture.

At block 802 of FIG. 11, the pacing tip electrode 32 may be advanced into the left ventricular septum to an LBB pacing location according to any of the techniques described above for positioning the tip electrode 32 in the vicinity of the LBB. For example, analysis of the paced or intrinsic EGM signal, analysis of the paced ECG signal obtained from one or more ECG sensing electrode vectors, and/or imaging guidance may be used for detecting a position of the pacing tip electrode 32 in the left ventricular septum, in an area for achieving LBB pacing.

At block 804, pacing pulses may be generated by the pulse generator of pacemaker therapy delivery circuit 84 (or by pulse generator 60 of external device 50) for delivery via the pacing tip electrode 32 and ring electrode 34. Control circuit 80 may control therapy delivery circuit 84 to deliver pacing pulses at a rate that is faster than the intrinsic heart rate or shortened AV delay in order to avoid fusion with an intrinsic ventricular depolarization or an inability to capture the heart due to the intrinsic rate being greater than the paced rate. For the sake of convenience, flow chart 800 is described according to the example of the pacing tip electrode 32 being configured as the cathode electrode with the ring electrode 34 configured as the return anode. In this case, cathodal capture of the LBB and anodal capture of the RBB may be achieved for providing bipolar BBB pacing. However, it is recognized that in other examples, the pacing tip electrode 32 may be configured as the return anode, e.g., via switching circuitry included in therapy delivery circuit 84, with the ring electrode 34 selected as the cathode electrode. In this case, bipolar BBB pacing is achieved when cathodal capture at the ring electrode 34 positioned in the vicinity of the RBB occurs simultaneously with anodal capture at the tip electrode 32 positioned in the vicinity of the LBB.

The pacing pulse output used to generate pacing pulses at block 804 may be set according to a default starting pulse amplitude and pulse width for bipolar pacing between tip electrode 32 and ring electrode 34 or programmed to desired starting values. When a most recent pacing pulse amplitude and width that resulted in BBB capture is known, the starting pulse amplitude and pulse width may be set to settings previously known to result in BBB capture. In other examples, the starting pacing pulse output may be set to a low or minimum output (e.g., minimum pulse amplitude for a given pulse width) and be progressively increased. In other instances, the starting pacing pulse output may be set to a high or maximum output (e.g., maximum pulse amplitude for a given pulse width) and be progressively decreased.

At block 806, a unipolar EGM signal may be sensed by the sensing circuit 86 of pacemaker 14 (or received by external device 50). The unipolar EGM signal is sensed using the selected anode electrode, ring electrode 34 in this example, in a unipolar sensing configuration. The EGM signal may be sensed at block 806 between the anode ring electrode 34 and pacemaker housing 15, a defibrillation coil electrode 35 if available on the pacing lead 18, or another available cutaneous or subcutaneous electrode. The unipolar EGM signal sensed using the ring electrode 34 may be analyzed by control circuit 80 or external device processor 52 for determining if pacing capture at the anode electrode is detected at block 808.

When ring electrode 34 is selected as the anode electrode and is positioned in the vicinity of the RBB, evidence of anodal capture of the RBB may be determined at block 808 by determining that at least one feature of the EGM signal meets RBB capture criteria. The anodal capture of the RBB may be determined by determining on one or more features of the unipolar EGM signal sensed from the ring electrode 34 (and pacemaker housing 15 or defibrillation electrode 35) and comparing the one or more features or the overall QRS waveform morphology to RBB capture criteria. The RBB capture criteria may include detecting a disappearance of a RBB block-like signal, a narrow QRS width, short RV activation time or other features and/or overall morphology shape of the unipolar EGM signal that corresponds to RBB capture. For example, the QRS width (or QRS duration) may be shortened during anodal pacing capture compared to cathodal pacing capture only, the RV activation time may be shortened, and the overall waveform morphology may change compared to a baseline unipolar EGM signal sensed using the ring electrode 34. Accordingly the determination at block 808 may include acquiring a unipolar EGM signal using the ring electrode 34 when the pacing output is low (below an expected anodal capture threshold), when pacing is not being delivered at all, or when unipolar pacing is delivered only via tip electrode 32 and another available return electrode (e.g., pacemaker housing 15) so that a baseline unipolar EGM signal may be obtained when RBB capture is known not to occur or not expected to occur. The baseline unipolar EGM signal sensed from the ring electrode 34 during no RBB capture may then be compared to the unipolar EGM signal feature(s) when RBB capture is unknown during pacing using the bipolar pacing electrode vector between tip electrode 32 and ring electrode 34. In some examples, control circuit 80 may control therapy delivery circuit 84 to start delivering pacing pulses at block 804 at a relatively low or minimum pacing pulse amplitude (or width) and progressively increase the pulse amplitude (or width) until a change in the unipolar anode EGM signal is detected at block 808. Examples of EGM signal features that may be determined for detecting capture of the RBB are described below in conjunction with FIG. 12.

When anodal capture of the RBB is not detected at block 808 e.g., based on an analysis of the unipolar EGM signal sensed using the ring electrode 34 and/or ECG signal analysis, the control circuit 80 may increase the pacing output at block 810, e.g., by either increasing the pulse amplitude and/or increasing the pulse width. In some examples, e.g., when the process of flow chart 800 is being performed at the time of lead 18 implantation, the external device 50 or imaging unit 70 may be used to verify a position of the ring electrode 34 in or at the right septum at block 812. Any of the techniques described above may be used for verifying the ring electrode 34 location, including using contrast imaging techniques for verifying that the ring electrode 34 is against the septum, delivering cathodal stimulation using the ring electrode 34 and verifying an LBB block pattern in the ECG signal, detecting a shortening of the RV activation time from a pacing pulse to a QRS peak in an ECG signal or the EGM signal sensed using the tip and/or ring electrodes 32 and 34, detecting a RBB potential signal, detecting an injury current, or other techniques as described herein. Block 812 is optional and may be performed at block 802 in the process of advancing the tip electrode 32 into the left ventricular septum but may be performed at any time during the process of flow chart 800 for verifying the position of tip electrode 32 and/or ring electrode 34. At other times, the process of flow chart 800 may be performed by control circuit 80 for capture monitoring, e.g. during a daily capture threshold test, during a bundle branch pacing therapy such that verification of the electrode position is not performed.

When performed in conjunction with an implantation procedure, any of the ECG signal features described previously herein and below in conjunction with FIG. 12 that indicate capture of the RBB, such as a disappearance of the RBB block pattern in the V1 or V2 ECG signals, shorter RV activation time determined as the time interval from the pacing pulse to a QRS peak, narrower QRS width and/or a shortened interventricular activation time delay determined as the difference between the RV activation time and the LV activation time, may be detected by external device processor 52 for detecting RBB capture. Additionally or alternatively, determination of EGM signal features, such as a QS or QSr evoked response morphology of the unipolar EGM signal sensed from ring electrode 32 or other overall waveform morphology analysis may be used in determining when the capture criteria are met at block 808 corresponding to RBB capture due to anodal stimulation at the ring electrode 34.

After increasing the pacing output at block 810 as needed, which may be one or more times, the control circuit 80 may detect anodal capture at block 808 according to RBB capture criteria. In other examples, control circuit 80 may decrease the pacing output at block 810 until capture is no longer detected to determine the anodal capture threshold. After determining anodal capture of the RBB, control circuit 80 may verify that cathodal capture is occurring at the tip electrode 32 by sensing the unipolar EGM signal at block 814 using the tip electrode 32 and an indifferent electrode (e.g., the pacemaker housing 15, a defibrillation coil electrode 35, or a cutaneous or subcutaneous electrode).

At block 816, control circuit 80 may compare one or more features of the QRS waveform and/or the overall QRS waveform morphology of the EGM signal to LBB capture criteria. Evidence of LBB capture that may be detected by control circuit 80 and/or external device processor 52 (for determining that LBB capture criteria are met) may include, but is not limited to, a QS or QSr evoked response morphology of the unipolar EGM signal sensed from the tip electrode 32, a shortened LV activation time from a pacing pulse to a peak of the EGM QRS signal, a shortened LV activation time from a pacing pulse to a peak (or other fiducial point) of an V5/V6 ECG QRS signal, a narrowed QRS width or duration in the unipolar EGM signal sensed using the tip electrode 32, a decreased interventricular activation time delay determined as the difference between an RV activation time and the LV activation time, disappearance of an LBB block pattern in an ECG signal, or another feature or overall morphology of the QRS waveform of the unipolar EGM signal sensed using the pacing tip electrode 32 that corresponds to LBB capture. Any examples described herein of cardiac signal features that are representative of delivery of a pacing pulse in the vicinity or area of the LBB may be used in determining if LBB capture criteria (indicating cathodal capture in this example) are met at block 816.

If the cathodal (LBB) capture criteria are met at block 816, control circuit 80 (or external device processor 52) may determine whether a lower pacing pulse output has been tested for achieving RBB capture at block 817. If RBB capture was determined at the starting pacing pulse amplitude and pulse width, the current pacing output may be greater than the RBB pacing capture threshold. In some instances, both RBB anodal capture and the LBB cathodal capture may be detected by control circuit 80 or processor 52 when pacing pulses are delivered using the starting pacing pulse output. The BBB pacing capture threshold may actually be lower than the starting pacing output. As such, at block 818, control circuit 80 or external device processor 52 may decrease the pacing output, e.g., by decreasing the pulse amplitude and/or pulse width. The process returns to block 806 to verify that RBB capture by anodal stimulation and LBB capture by cathodal stimulation are achieved at the lower pacing output.

When cathodal capture of the LBB is determined at block 816, control circuit 80 may determine that lower test pacing output settings are not available at block 817 for achieving RBB capture (e.g., when an increase in pacing pulse output was previously required at block 810 in order to detect anodal capture of the RBB at block 808). Reducing the pacing output may result in RBB loss of capture. Control circuit 80 (or external device processor 52) may determine that the current pacing pulse output that resulted in both RBB capture and LBB capture corresponds to the BBB capture threshold at block 825.

In general, anodal capture may require a higher pacing pulse output than cathodal capture. As such, anodal capture of the RBB when ring electrode 34 is selected as the anode may be verified first, with any necessary adjustments of the pacing output required to achieve RBB capture. Once anodal capture is achieved, cathodal capture of the LBB when tip electrode 32 is selected as the cathode is expected. The anodal capture threshold may represent the BBB pacing capture threshold. In some instances, however, depending on the relative location of the tip electrode 32 to the LBB and other factors, the cathodal capture threshold of the LBB may be higher than the anodal capture threshold of the RBB when bipolar pacing pulses are delivered between the tip electrode 32 and ring electrode 34. When LBB capture is not detected at block 816 after anodal capture of the RBB is determined, the pacing output may be increased at block 820 until capture of the LBB is detected at block 824 based on the unipolar EGM signal sensed at block 822 using the tip electrode 32 and an indifferent electrode and/or ECG signal analysis. When control circuit 80 or external device processor 52 determines that the unipolar EGM signal sensed from the tip electrode 32 meets the LBB capture criteria at block 824, BBB capture is detected at block 825. Control circuit 80 may determine the BBB capture threshold for bipolar pacing at block 825 as the current pacing output (e.g., current pulse amplitude and pulse width) when the pacing output is at the lowest setting tested that results in both RBB and LBB capture criteria being met.

In response to determining the BBB capture at block 825, therapy delivery circuit 84 may deliver BBB pacing at block 826 using a pacing pulse output that is equal to or greater than the BBB capture threshold, e.g., the lowest pacing output at which both RBB capture and LBB capture are verified plus a safety margin, using a pacing electrode configuration including the pacing tip electrode 32 as the cathode and the ring electrode 34 as the anode. The safety margin may be between 0.25 and 1.0 V, as examples. The bipolar BBB pacing delivered at block 826 may include setting the pacing output, e.g., the pacing pulse amplitude and/or the pacing pulse width, at a safety margin greater than the BBB capture threshold to promote effective BBB pacing and reducing the likelihood of loss of BBB capture. Other pacing pulse control parameters that may be set by control circuit 80 and used by therapy delivery circuit 84 may include monophasic, biphasic or other multiphasic waveform shape.

The process of flow chart 800 may be performed at the time of implantation of the pacing electrodes 32 and 34 such that processing and analysis of received ECG and EGM signals may be performed by external device processor 52 or processing and analysis of EGM signals may be performed by control circuit 80 of pacemaker 14. The process of flow chart 800 or portions thereof for detecting BBB capture and determining a BBB pacing capture threshold may be performed at any time during pacing therapy delivery by a pacemaker, e.g., pacemaker 14, for detecting BBB loss of capture (e.g., loss of one or both of RBB capture and/or LBB capture) and redetermining the BBB pacing capture threshold. The pacing pulse output may be adjusted to regain BBB capture and maintain effective BBB pacing and/or the pacing electrode configuration may be changed, e.g., by switching the anode and cathode electrode polarities.

The examples described herein generally refer to cathodal pacing capture of the LBB in the vicinity of tip electrode 32 and anodal pacing capture of the RBB in the vicinity of the ring electrode 34. It is contemplated, however, that the polarity of the electrodes 32 and 34 may be reversed to provide cathodal stimulation at the ring electrode 34 and anodal stimulation at the tip electrode 32. When the tip electrode 32 is selected as the anode and the ring electrode 34 is selected as the cathode, it is to be understood that control circuit 80 verifies capture at the anode at block 808 by determining that LBB capture criteria are met. At block 816, control circuit 80 verifies capture at the cathode by determining that RBB capture criteria are met. Depending on the relative locations of the electrodes 32 and 34 to the LBB and the RBB respectively, a lower BBB capture threshold may be achieved when the ring electrode 34 is the cathode electrode and the tip electrode 32 is the anode electrode. Furthermore, depending on the selectable polarity of each electrode coupled to the pacemaker 14 or 114, both electrodes 32 and 34 (or housing based electrodes 132 and 134) may be used as cathode electrodes paired with an anode electrode carried by the lead 18, housing 15 (or housing 114) to provide cathodal stimulation in the area of the RBB and the LBB to achieve BBB pacing using dual unipolar or bipolar electrode vectors.

Figure 12:
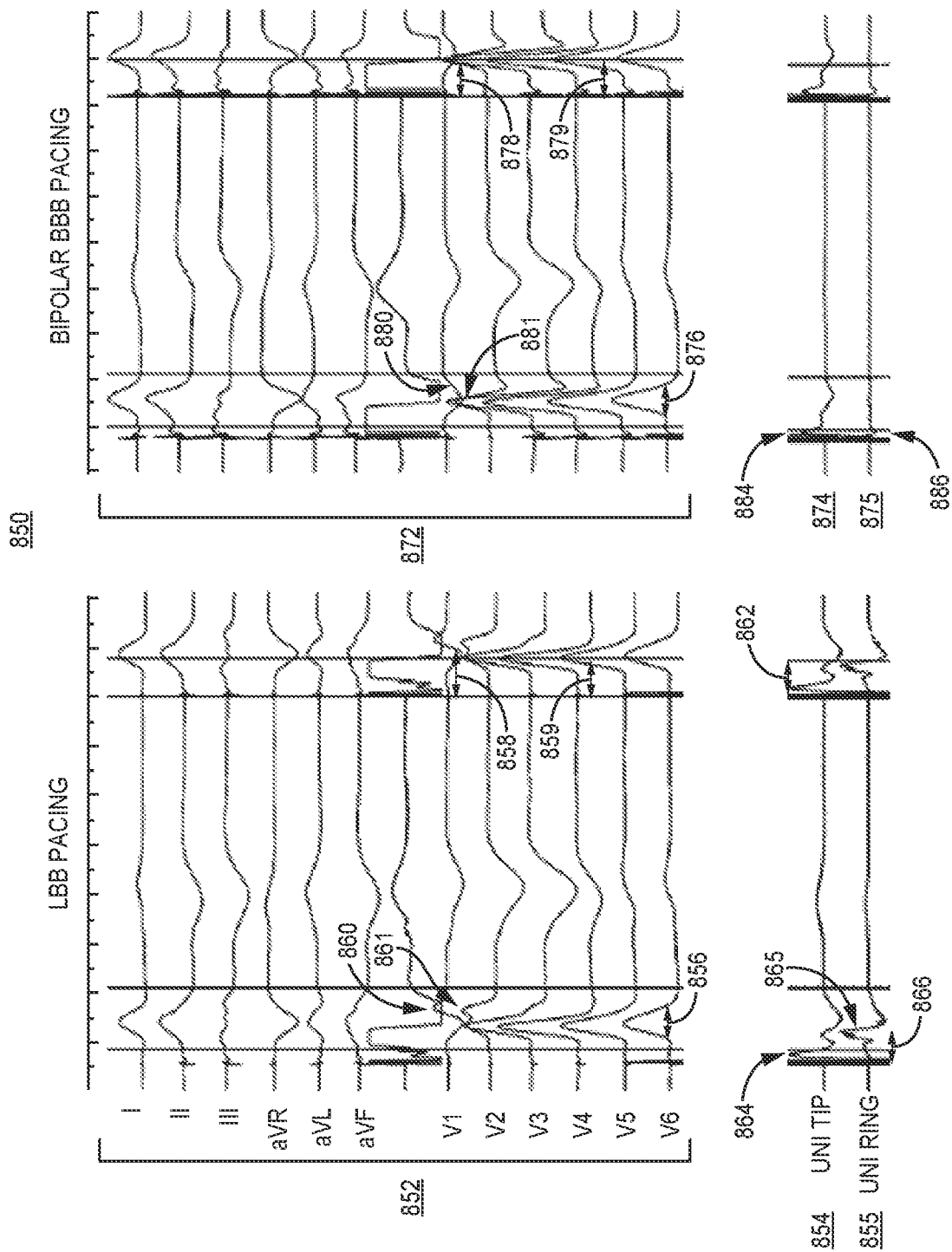
FIG. 12 is a diagram of cardiac electrical signals that may be sensed and analyzed by a medical device for determining BBB capture.

FIG. 12 is a diagram 850 of cardiac electrical signals 850 that may be sensed and analyzed by a medical device for determining BBB capture, e.g., during a BBB capture test, capture threshold search or during BBB pacing for capture management monitoring. The ECG signals 852 and EGM signals 854 and 855 shown in the left panel are representative of signals sensed during unipolar, LBB pacing using the tip electrode 32 paired with the pacemaker housing 15, for example. During a BBB pacing capture test, control circuit 80 may control therapy delivery circuit 84 to deliver unipolar LBB pacing in order to obtain one or more ECG signals 852 (by external device 50) and/or EGM signals 854 when the RBB is known not to be captured. In some instances, lead 18 may be coupled to external device 50 such that external device pulse generator 60 is generating the pacing pulses delivered for unipolar LBB pacing. The morphology and/or specific signal features of one or more of the ECG signals 852 and/or EGM signals 854 and 855 may be determined by external device processor 52. Control circuit 80 may determine EGM signal features when therapy delivery circuit 84 is delivering unipolar LBB pacing for characterizing the signal features(s) during no RBB capture. In the example shown, a unipolar EGM signal sensed using the tip electrode (UNI TIP EGM 854) and a unipolar EGM signal sensed using the ring electrode (UNI RING EGM 855) are shown. The unipolar sensed EGM signals 854 and 855 may be sensed using any available anode electrode, e.g., the pacemaker housing 15, defibrillation electrode 35 (shown in FIG. 2D) or a cutaneous (skin) or subcutaneous electrode.

The right panel including ECG signals 872 and EGM signals 874 and 875 are representative of signals sensed during bipolar BBB pacing when the tip electrode 32 is in the LBB area (e.g., in the left ventricular septum) and the ring electrode 34 is in the RBB area (e.g., in the right ventricular septum). During a capture threshold test or capture verification for capture management, control circuit 80 or external device processor 52 may adjust the pacing pulse output, e.g., increase the pacing pulse amplitude and/or pulse width starting from a relatively low pulse output, until a feature of one or more of the ECG signals 872 and/or EGM signals 874 is determined by processor 52 and/or control circuit 80 to meet BBB capture criteria. The BBB capture criteria may be met based on a comparison to ECG and/or EGM signal features determined during the unipolar LBB pacing as shown in the left panel. A change in a signal sensed during LBB unipolar pacing (with verified LBB capture and no RBB capture) as represented in the left panel of diagram 850 to a signal meeting RBB capture criteria, as shown in the right panel, may be determined as bipolar BBB pacing capture.

During unipolar LBB pacing, external device processor 52 may determine the QRS signal width 856 for comparison to the QRS signal width 876 determined during bipolar pacing. The QRS signal widths 856 and 876 are shown relative to V6 ECG signals for the sake of convenience, however, the QRS signal width may be determined from any of the ECG signals 852 and 872 for analysis for determining BBB capture. As described above, during LBB pacing, the QRS signal width 856 of the V5/V6 ECG signal may be relatively narrower than when the LBB is not paced and may be detected as an indication of LBB pacing capture and the position of the tip electrode 32 being in the area of the LBB. However, when the RBB is also captured by ring electrode 34, a further narrowing of the QRS signal width 876 is detected. External device processor 52 may determine a relative decrease in the QRS signal width, e.g., as shown by the shorter signal width 876 compared to signal width 856, as evidence of BBB pacing capture. In other examples, the QRS signal width 876 during bipolar BBB pacing may be compared to a threshold signal width for determining BBB capture. Processor 52 or control circuit 80 may set a QRS signal width threshold applied to a given ECG signal based on the QRS signal width determined during unipolar LBB pacing.

The RV activation time 858 and LV activation time 859 may be determined from V1 or V2 ECG signals and V5 or V6 ECG signals, respectively, by external device processor 52 during unipolar LBB pacing in some examples. Likewise, the RV activation time 878 and the LV activation time 879 may be determined during bipolar BBB pacing. When the RV activation time 878 during bipolar BBB pacing is less than a threshold value, which may be based on the RV activation time 858 during unipolar LBB pacing, bipolar BBB pacing capture may be determined. In other examples, the difference between the RV activation time 858 and the LV activation time 859 during unipolar LBB pacing may be determined as the interventricular activation time difference and compared to the difference between the RV activation time 878 and the LV activation time 879 during bipolar BBB pacing. When this interventricular activation time difference between RV and LV activation times decreases, bipolar BBB pacing capture may be detected by external device processor 52. As observed in FIG. 12, both the RV activation time 878 and the LV activation time 879 may decrease during bipolar BBB pacing due to BBB pacing capture. The difference between the RV activation time and the LV activation time decreases compared to unipolar LBB pacing due to substantially simultaneous activation of the RBB and LBB during bipolar BBB pacing. The external device processor 52 may determine shortened activation time differences between the V1/V2 ECG signals (corresponding to RV activation time) and the V5/V6 ECG signals (corresponding to LV activation time) that occurs during BBB pacing capture compared to LBB only capture.

Additionally or alternatively, external device processor 52 may analyze the morphology of the V1 and/or V2 ECG signals during unipolar LBB pacing and during bipolar BBB pacing. The V1 ECG signal exhibits a QSR' morphology 860 during unipolar LBB pacing. The R' signal disappears during bipolar pacing with BBB capture as represented by the QS morphology 880. The V2 ECG signal exhibits a notched morphology 861 during unipolar LBB pacing. The notched morphology disappears during BBB capture as represented by the narrow QRS morphology 881. Accordingly, the external device processor 52 may receive the ECG signals 852 and 872 and when the V1 ECG signal is determined to include a QS morphology (disappearance of R') and/or the V2 ECG signal includes a narrow QRS morphology with a single peak (no notched waveform), BBB pacing capture may be determined by external device processor 52. These changes in the V1 and V2 ECG signals represent an RBB block pattern correction when BBB capture occurs. The external device processor 50 may determine and/or generate output for display on display unit 54 representing the disappearance of the RBB block pattern in the V1/V2 signals during BBB pacing capture (right panel) with the disappearance of the V1 R' signal and the notched waveform of the V2 signal that appear during LBB only capture. These changes in V1 and/or V2 ECG signal morphology may be detected by external device processor 52 as the pacing pulse output is varied in order to verify bipolar BBB capture and to determine the lowest pacing pulse output at which bipolar BBB capture occurs.

The unipolar tip EGM signals 854 and 874 sensed using pacing tip electrode 32 and an indifferent electrode (e.g., a cutaneous or subcutaneous electrode or the pacemaker housing 15) and the unipolar ring EGM signal 855 and 875 (sensed using the ring electrode 34 and an indifferent electrode) are also shown in FIG. 12. These EGM signals 854, 855, 874 and 875 may be sensed by pacemaker sensing circuit 86 during unipolar LBB pacing and during bipolar BBB pacing and passed to control circuit 80 of pacemaker 14 for analysis by processor 148 for detecting BBB pacing capture. In other examples, pacemaker 14 may transmit the sensed EGM signals to external device 50 for processing and analysis by external device processor 52, which may be in addition to or in combination with analysis of ECG signals 852 and/or 872 as described above.

The unipolar tip EGM signal 854 exhibits a fast LV activation and narrow QRS width 864 during unipolar LBB pacing with no RBB capture. The unipolar ring EGM signal 855 exhibits a relatively wider QRS signal 865 at a delayed RV activation time 866 due to non-capture of the RBB during unipolar LBB pacing. The interventricular activation time difference 862, e.g., between a maximum peak (or other fiducial point) of the unipolar tip EGM signal 854 and a maximum peak (or other fiducial point) of the unipolar ring EGM signal 855, may be determined by control circuit 80 (or external device processor 52).

During bipolar pacing with BBB capture, the early, narrow signals 884 and 886 in both the unipolar tip EGM signal 874 and the unipolar ring EGM signal 875 indicate simultaneous capture of both the LBB and RBB. The LV activation and the RV activation are fast and simultaneous (or near simultaneous) such that a minimal or near zero interventricular activation time difference exists between the QRS signal 884 and QRS signal 886 of the unipolar tip EGM signal 874 and the unipolar ring EGM signal 875, respectively. The delayed, wide QRS signal 865 in the unipolar ring EGM signal 855 disappears in the unipolar ring EGM signal 875.

Pacemaker control circuit 80 may determine BBB pacing capture in response to determining a shortening of the EGM R-wave duration (or QRS width) in the unipolar ring EGM signal, a shortening of the RV activation time determined from the unipolar ring EGM signal, and/or a near zero interventricular activation time difference between the maximum peak (or other fiducial point) of the unipolar tip EGM signal and the maximum peak (or other fiducial point) of unipolar ring EGM signal during bipolar pacing compared to unipolar LBB pacing. In some examples, control circuit 80 or external device 52 may detect the disappearance of the delayed, wide QRS signal 865, which may be considered an RBB-block like signal as observed during unipolar LBB pacing, as evidence of bipolar BBB capture occurs.

While not shown in FIG. 12, the bipolar EGM signal may be sensed between the tip and the ring electrodes 32 and 34 during bipolar BBB pacing. In the bipolar EGM signal, no potential difference may exist between the simultaneously captured tissues at the cathode tip electrode 32 and anode ring electrode 34 (or vice versa) resulting in no QRS signal or a very small amplitude QRS signal. Accordingly, a disappearance of the QRS waveform or a very small QRS peak amplitude in the post-pace bipolar EGM signal during bipolar BBB pacing may be detected by control circuit 80 or external device processor 52 as evidence of bipolar BBB anode capture, toward meeting BBB capture criteria.

Changes in the EGM signals shown in FIG. 12 which may include any of a change in peak (positive or negative) amplitude, change in polarity, change in peak timing, change in number of peaks, change in peak-to-peak amplitude difference, change in maximum (positive or negative) slope, change in area of the waveform (QRS area), change in QRS width, and/or change in overall QRS waveform shape may be detected by control circuit 80 or external device processor 52, alone or in any combination, as evidence of BBB capture compared to LBB capture only with no RBB capture (or compared to no bundle branch pacing).

It is recognized that when the pacemaker control circuit 80 is performing the signal processing and analysis, control circuit 80 may receive and analyze at least the unipolar ring EGM signal in some examples. In other examples, control circuit 80 may receive and analyze one or more of the unipolar tip EGM signal, the unipolar ring EGM signal and/or the bipolar EGM signal sensed between the tip and ring electrodes 32 and 34 for detecting BBB pacing capture.

Pacemaker 14 or 114 may operate to detect BBB capture on a beat-by-beat basis or a less frequent basis, e.g., at scheduled times of day (e.g., once per minute, once per hour, once per day) or at selected sampling rate (e.g., every 10 beats, every 30 beats, or other frequency) to detect loss of BBB capture. Control circuit 80 may detect loss of BBB capture based on only RBB capture criteria being met or only left LBB capture criteria being met or neither RBB or LBB capture criteria being met as applied to the unipolar ring EGM signal and/or the unipolar tip EGM signal and/or a bipolar EGM signal as described above. In other examples, other electrodes available for sensing a near-field or far-field EGM signal may be used for detecting changes in the EGM signal indicative of bundle branch capture. For example, when a defibrillation coil electrode is available (e.g., as shown in FIG. 2D), a far-field EGM signal may be sensed using the defibrillation coil electrode and the pacemaker housing. Determination of a feature of the far-field EGM signal, such as QRS width, may be indicative of capture or loss of capture of one or both bundle branches because the far-field EGM signal is more representative of the global ventricular electrical activity of both the right and left ventricles than a near-field EGM signal. For example, the far-field EGM signal may represent the summation of depolarization signals occurring over a greater volume or mass of the right and left ventricles than a near-field EGM signal. Features of the far-field EGM signal may be used to detect improvement in ventricular electrical synchrony due to BBB pacing above the capture threshold for both the RBB and LBB. For instance, progressive narrowing of the far-field EGM QRS signal width from the QRS width when no pacing is delivered, when only LBB pacing is being delivered, to when bipolar BBB pacing is being delivered may be evidence of BBB pacing capture.

In some examples, control circuit 80 may detect loss of BBB capture during a capture monitoring check based on BBB capture criteria not being met, e.g., a return of the delayed, wide QRS signal 865 in the unipolar, ring EGM signal 855 or a relatively wide QRS signal in either of the unipolar EGM signals 854 and/or 855. In response to determining loss of BBB capture, control circuit 80 may perform the process of flow chart 800 in FIG. 11 to redetermine the BBB capture threshold or increase the pacing output until BBB capture is re-established based on an analysis of sensed EGM signals. Furthermore, it is to be understood that the signal features determined during LBB only capture and/or during BBB capture may be generated as output by external device processor 52 for display by display unit 54 in some examples, e.g., in a GUI, to provide a visual representation of the changes in the ECG and/or EGM signals. The ECG and/or EGM signals may be displayed and/or data derived therefrom to guide a user in selecting a pacing pulse output and/or pacing electrode configuration based on changes in the ECG and/or EGM signals indicative of improved ventricular synchrony (e.g., decreased QRS width, decreased interventricular conduction time, disappearance of a RBB block-like signal and/or disappearance of an LBB block-like signal).

The ECG and EGM signal features shown and described in conjunction with FIG. 12 are described in conjunction with a bipolar BBB pacing electrode configuration for simultaneous capture of the RBB and LBB using a single bipolar pacing electrode vector (anodal plus cathodal capture). It is to be understood, however that the same or analogous features of the ECG signals and/or EGM signals may be determined when the pacing electrode configuration is selected for delivering BBB pacing using two different unipolar pacing electrode vectors, two different bipolar pacing electrode vectors, or one unipolar and one bipolar pacing electrode vector for separately pacing the RBB and LBB in unison. For instance, when BBB capture is achieved, regardless of the pacing electrode configuration, the ECG and EGM signal features described in conjunction with the right panel of FIG. 12 associated with bipolar BBB capture may be detected for determining BBB capture during pacing according to other pacing electrode configurations selected for pacing both of the RBB and LBB.

Figure 13:
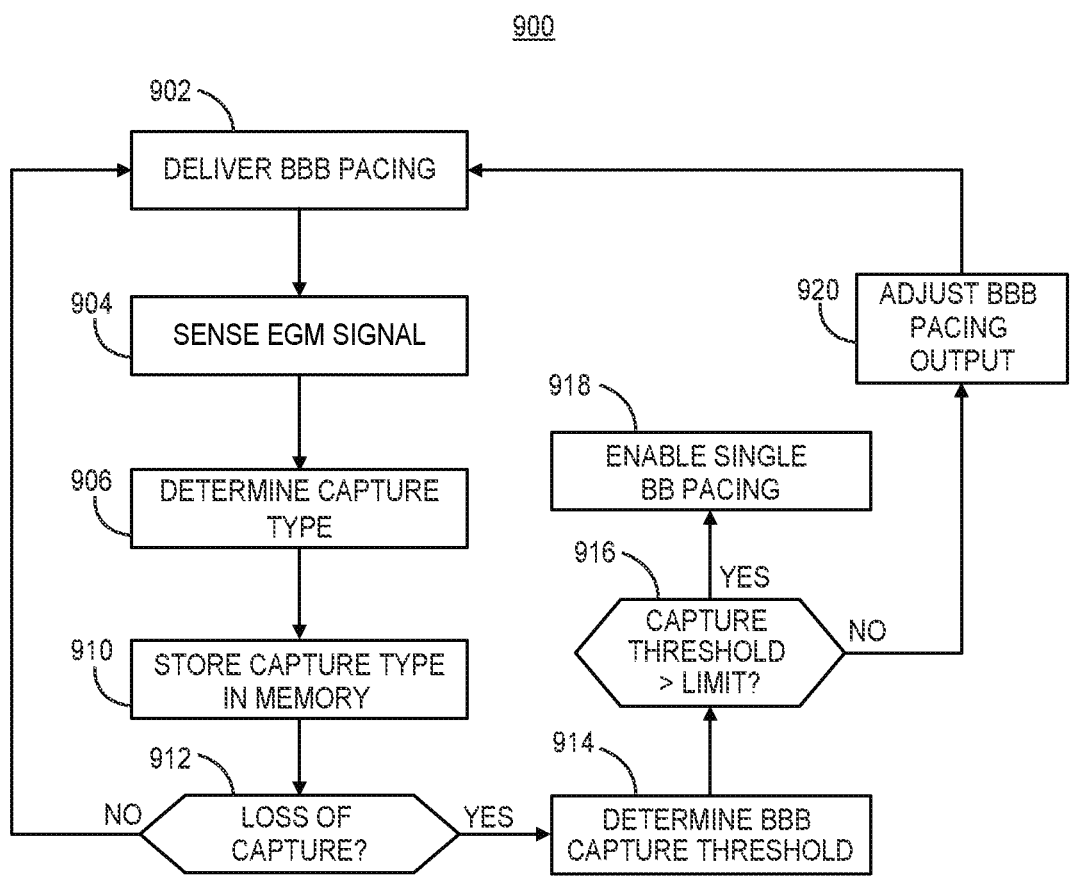
FIG. 13 is a flow chart of a method that the pacemaker of FIG. 2A may perform for monitoring pacing capture during BBB pacing according to one example.

FIG. 13 is a flow chart 900 of a method that control circuit 80 may perform according to one example for monitoring for capture during BBB pacing. In some examples, pacemaker control circuit 80 may perform beat-by-beat, sampled or scheduled capture monitoring to determine when only RBB capture occurs, only LBB capture occurs, when BBB capture occurs or when total LOC occurs during capture monitoring or during a capture threshold test. During capture monitoring when BBB pacing is being delivered, control circuit 80 may store counts of these different types of capture in memory 82 in some examples in order to output the frequency or percentage of time that effective BBB capture is achieved, as well as the relative percentages of time of RBB capture only, LBB capture only and/or loss of capture.

At block 902, therapy delivery circuit 84 delivers BBB pacing according to selected BBB pacing parameters. The BBB pacing pulse may be delivered at a premature pacing interval. The BBB pacing pulse may be delivered at a shortened AV delay or at a ventricular rate that is faster than the intrinsic heart rate to promote pacing pulse delivery earlier than the intrinsic depolarization of the myocardium. The BBB pacing parameters may include selecting bipolar or unipolar BBB pacing. When bipolar BBB pacing is selected, the tip and ring electrodes 32 and 34 may be selected as a cathode and anode pair such that one of the LBB or RBB is paced by a selected cathode electrode (tip electrode 32 or ring electrode 34) and the other of the RBB or LBB is paced by a selected anode electrode (ring electrode 34 or tip electrode 32) of the bipolar pacing pair. When unipolar BBB pacing is selected, the LBB may be paced unipolar using the tip electrode 32 and the pacemaker housing 15 or a defibrillation coil electrode 35 if available. Similarly, the RBB may be paced unipolar using the ring electrode 34 and the pacemaker housing 15 or a defibrillation coil electrode 35 if available. In some cases, BBB pacing may be achieved by a single unipolar pacing electrode vector when one bundle branch is captured directly and the second, opposite bundle branch is captured by virtual current or break excitation.

In still other examples, when two different bipolar electrode pairs are available e.g., as shown in FIGS. 2B and 2C, which may or may not share a common anode, the BBB pacing at block 902 may be delivered by delivering RBB pacing using a first bipolar electrode pair and delivering bipolar LBB pacing using a second bipolar electrode pair. The selected BBB pacing parameters may further include a pacing pulse amplitude and pacing pulse width, which may be based on a BBB capture threshold (or individual RBB and LBB capture thresholds) determined as the lowest pacing output(s) at which BBB capture is detected according to any of the examples described above.

At block 904, sensing circuit 86 may sense an EGM signal that is passed to control circuit 80 for analysis for determining capture during the BBB pacing. Sensing circuit 86 may pass a unipolar EGM signal sensed using the ring electrode 32 and/or a unipolar EGM signal sensed using the tip electrode 34. In some instances, the bipolar EGM signal between tip electrode 32 and ring electrode 34 may be sensed. In examples that include bipolar electrode pairs for pacing the RBB and the LBB separately, e.g., as shown in FIGS. 2B and 2C, a bipolar EGM signal may be sensed from the right ventricular septum and a bipolar EGM signal may be sensed from the left ventricular septum at block 904. Depending on the electrodes available and the configuration of sensing circuit 86, one or more unipolar signals and/or one or more bipolar signals may be sensed at block 904.

At block 906, control circuit 80 analyzes the EGM signal(s) received from sensing circuit 86 for determining the capture type following a bipolar BBB pacing pulse or following the separate unipolar or bipolar LBB and RBB pacing pulses delivered to capture both of the RBB and the LBB. Separate but simultaneous pacing pulses may be delivered to the RBB and the LBB, or the separate pacing pulses may be delivered according to an interventricular delay to improve ventricular electrical synchrony.

The capture type may be determined by control circuit 80 at block 906 by analyzing the received EGM signal(s) according to any of the examples described above in conjunction with FIG. 12. For example, BBB capture may be determined based on the QRS signal width of the unipolar EGM signal sensed using an electrode positioned in the left ventricular septum, the QRS signal width of the unipolar EGM signal sensed using an electrode positioned in the right ventricular septum, the LV activation time, the RV activation time, the interventricular activation time difference, a bipolar QRS signal amplitude or polarity, a disappearance of a RBB block-like signal, a disappearance of an LBB block-like signal, or any combination thereof.

LBB only capture may be detected when the LV activation time is less than the RV activation time and/or less than a predetermined threshold and/or the LV QRS signal width is less than the RV QRS signal width or a predetermined threshold. LBB only capture may be detected when a delayed, relatively wide QRS signal is sensed in the unipolar EGM signal sensed from the right portion of the septum, representing a RBB block-like signal.

RBB only capture may be detected when the RV activation time is less than the LV activation time and/or less than a predetermined threshold and/or the RV QRS signal width is less than the LV QRS signal width or a predetermined threshold. RBB only capture may be detected when a delayed, relatively wide QRS signal is sensed in the unipolar EGM signal sensed from the left portion of the septum, representing an LBB block-like signal.

In general, LBB only capture determination may be based on LBB capture criteria being met when RBB capture criteria are not met, and RBB only capture determination may be based on RBB capture criteria being met when LBB capture criteria are not met. In some instances, control circuit 80 may determine loss of capture at block 906 when neither the LBB capture criteria nor the RBB capture criteria are met.

In response to determining the capture type, control circuit 80 may store the capture type in memory 82 at block 910. In some examples, control circuit 80 may determine the capture type on a beat-by-beat basis continuously, continuously over scheduled time intervals including multiple BBB paced beats, or on a sampled basis, e.g., every nth beat, as examples. Memory 82 may store a histogram count of the number of BBB capture beats, LBB only capture beats, RBB only capture beats, and/or loss of capture beats. The counts of determined capture types may be stored in memory 82 at block 910 for transmission to external device 50 for reporting the type of capture as a percentage of time or percentage of paced ventricular beats. External device processor 52 may generate output for display on display unit 52 representative of the capture type data received from pacemaker 14. For example, effective BBB pacing may be determined as the percentage of BBB capture determinations out of all capture determinations made during capture monitoring.

When no loss of capture of either the RBB or the LBB is determined at block 912, i.e., when BBB pacing capture is determined at block 906, control circuit 80 returns to block 902 to continue delivering BBB pacing ("no" branch of block 912). The current pacing electrode configuration and pacing pulse output settings are effective in capturing both bundle branches. However when loss of capture of one or both of the LBB and/or RBB is determined at block 912 (based on the determination at block 906 of RBB only capture, LBB only, or BBB loss of capture), control circuit

80 may advance to block 914 ("yes" branch of block 912). Control circuit 80 may perform a BBB capture threshold search at block 914 in order to adjust the BBB pacing pulse output at block 920 for restoring BBB capture.

When bipolar BBB pacing is being delivered and is determined to result in loss of capture of the LBB, the RBB or both, control circuit 80 may perform a BBB capture threshold search using techniques described above in conjunction with FIG. 11. For example, control circuit 80 may increase the pacing pulse output (amplitude or width) until anodal capture of one of the RBB or LBB is verified and then verify cathodal capture of the other of the LBB or RBB. Control circuit 80 may determine the bipolar BBB pacing capture threshold as the lowest pacing pulse output that results in capture of both the RBB and the LBB, which may be determined based on an analysis of the unipolar tip EGM signal and/or unipolar ring EGM signal (and/or the bipolar EGM signal) received from sensing circuit 86 as described above.

When two different pacing electrodes are being used to pace the LBB and the RBB in unison, such as dual unipolar or dual bipolar pacing electrode vectors, control circuit 80 may determine the RBB capture threshold as the lowest pacing pulse output delivered to the RBB pacing electrode vector when RBB capture criteria are met. The LBB capture threshold may be determined as the lowest pacing pulse output delivered to the LBB pacing electrode vector when LBB capture criteria are met. The higher of the two RBB and LBB pacing capture thresholds may be determined as the BBB pacing capture threshold in some examples.

At block 916, control circuit 80 may compare the BBB capture threshold to a pacing output limit. In some examples, pacing of only one of the LBB or the RBB may be preferred over bipolar BBB pacing when the bipolar BBB pacing capture threshold exceeds a pacing output limit. When the pacing pulse amplitude and/or pulse width required to achieve bipolar BBB pacing capture at both the cathode and anode exceeds a threshold limit, the high current drain from power supply 98 may result in an unacceptable shortening of the usable life of the pacemaker 14. A tradeoff between the clinical benefits of bipolar BBB pacing capture and the useful life of the pacemaker 14 may exist such that when the bipolar BBB pacing capture threshold exceeds a predetermined limit, control circuit 80 may select single RBB or single LBB pacing at block 918. Control circuit 80 may select LBB pacing using the pacing tip electrode 32 as the cathode electrode, for example, and set the pacing pulse output to an amplitude and pulse width that results in cathodal capture of the LBB without anodal capture of the RBB.

When the bipolar BBB pacing capture threshold is within a pacing output limit at block 916, control circuit 80 may adjust the pacing pulse output parameters at block 920 based on the capture threshold determined at block 914. For example, the pacing pulse amplitude or the pacing pulse width may be set at a safety margin greater than the bipolar BBB capture threshold pulse amplitude or pulse width, respectively. Control circuit 80 returns to block 902 to continue delivering bipolar BBB pacing according to the adjusted pacing output parameters and may continue to monitor for capture.

When BBB pacing is being delivered by dual unipolar or dual bipolar (or one unipolar and one bipolar) pacing electrode vector, the BBB capture threshold (determined as the greatest one of the LBB capture threshold or RBB capture threshold) and/or the individual RBB capture threshold and LBB capture threshold may be compared to capture threshold limit(s) at block 916. In some cases, the pacing pulse energy required to capture both of the LBB and the RBB using two different pacing electrode vectors may exceed an acceptable pacing pulse energy. Accordingly, a combination of the RBB capture threshold and LBB capture threshold may be compared to a capture threshold limit and/or each may be compared individually to capture threshold limits. In some examples, a logical operation may be performed to assess the pacing capture thresholds. For example, when one of the LBB or RBB capture threshold is falls into a relatively high pulse output range but the other of the RBB or LBB capture threshold falls into a relatively low pulse output range, the combined RBB and LBB capture thresholds may be determined to be within a capture threshold limit at block 916. When the combination of the RBB and LBB capture thresholds in a dual pacing electrode vector configuration is within a specified capture threshold limit at block 916, control circuit 80 may adjust the pacing pulse output for RBB pacing and/or LBB pacing as needed at block 920 to restore BBB capture during pacing at block 902. If, however, the combination of the RBB and LBB capture thresholds are not less than or equal to the capture threshold limit at block 916, control circuit 80 may select a different pacing electrode configuration at block 918. For example, a single RBB pacing electrode configuration or a single LBB pacing electrode configuration may be selected at block 918, with the pacing pulse output set according to the respective RBB or LBB pacing capture threshold.

BBB pacing capture may be determined by pacemaker control circuit 80 using the techniques disclosed herein without necessarily altering the timing of pacing pulses or delivering separate pacing pulses to the LBB and RBB. The techniques may however include delivering bipolar BBB pacing with the cathode electrode in the left ventricular septum in the area of the LBB, bipolar BBB pacing with the cathode electrode in the right ventricular septum in the area of the RBB, and/or dual unipolar or dual bipolar pacing using a cathode electrode in the area of the RBB and a cathode electrode in the area of the LBB. Control circuit 80 may analyze and detect changes in the features and/or overall morphology of one or more EGM signals (and/or ECG signals when external processor 52 is performing signal analysis) during pacing pulse delivery to detect RBB only capture, LBB only capture, BBB capture and/or loss of capture. Control circuit 80 may distinguish different types of capture and determine capture threshold(s). By determining the capture threshold(s) based on the EGM (and/or ECG signals), control circuit 80 or external device processor 52 may determine an optimal pacing electrode configuration (pacing electrode polarities and unipolar or bipolar configurations) for delivering ventricular pacing. The optimal pacing electrode configuration may be one pacing electrode vector or a combination of pacing electrode vectors that result in the lowest pacing capture threshold or total pacing pulse energy output that also results in an improvement in ventricular electrical synchrony, e.g., based on shortening of the QRS width and/or interventricular activation time difference, as examples.

Figure 14:
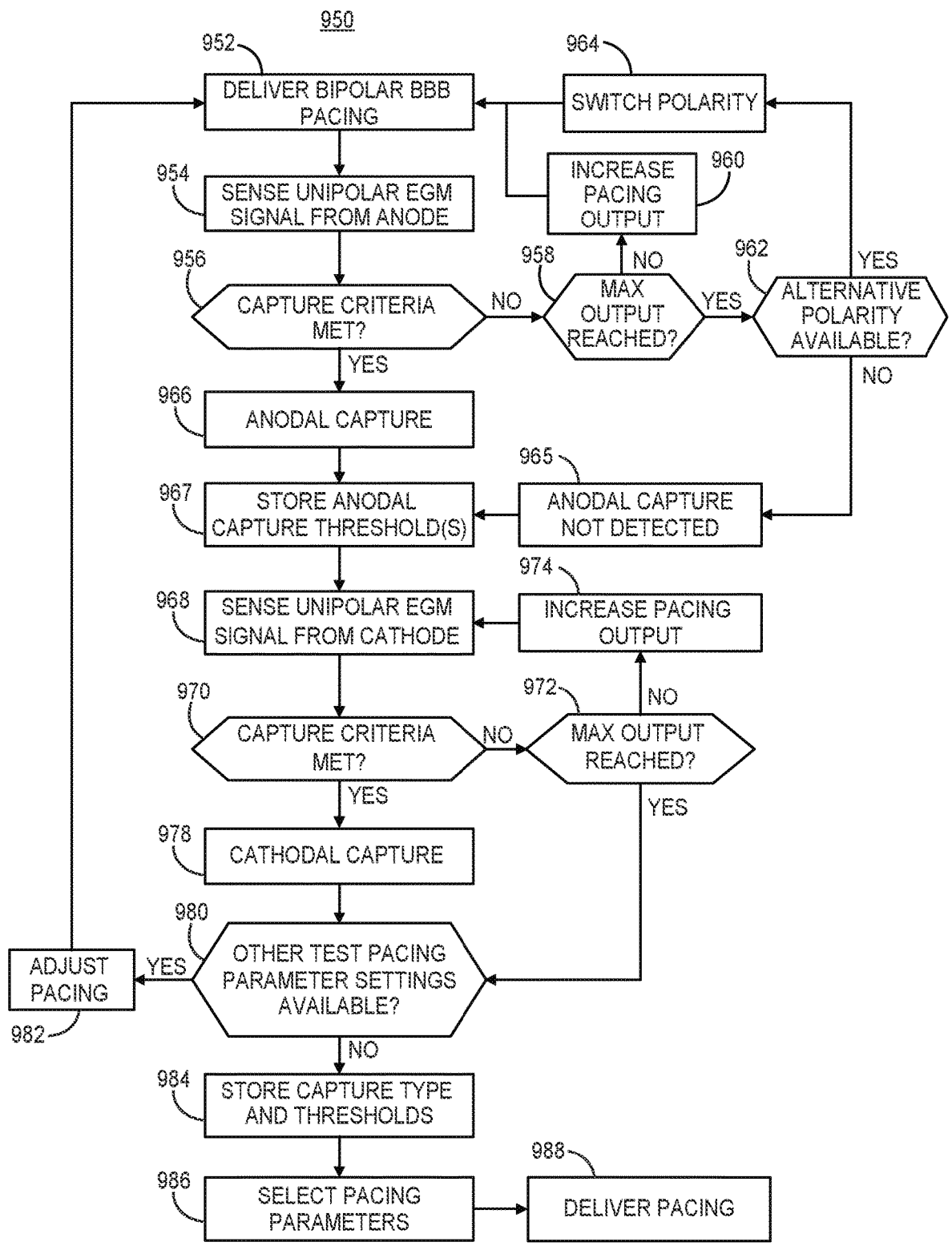
FIG. 14 is a flow chart of a method for determining right bundle branch (RBB) capture and LBB capture for determining a bipolar BBB capture threshold according to one example.

FIG. 14 is a flow chart 950 of a method for determining RBB capture and LBB capture for determining bipolar BBB capture threshold according to one example. The bipolar BBB capture threshold, as well as the individual RBB capture threshold (anodal or cathodal) and/or LBB capture threshold (cathodal or anodal), may be stored in pacemaker memory 82 for comparisons to changes in capture thresholds over time and controlling adjustment to pacing pulse output control parameters and selection of pacing electrode configuration. In some instances, the RBB capture threshold, which may be anodal capture or cathodal capture depending on the electrode polarities, may be the bipolar BBB capture threshold (when LBB only capture occurs at a lower pacing pulse output). In other instances, the LBB capture threshold, which may be cathodal capture or anodal capture depending on the electrode polarities, may be the bipolar BBB capture threshold (when RBB only capture occurs at a lower pacing pulse output).

At block 952, bipolar BBB pacing is delivered by therapy delivery circuit 84 using the bipolar electrode pair having one electrode positioned in the left ventricular septum, in the area of the LBB and one electrode positioned in the right ventricular septum, in the area of the RBB. Therapy delivery circuit 84 may select the pacing tip electrode 32 to be the cathode electrode for LBB capture and the ring electrode 34 to be the anode electrode for RBB capture or vice versa. The tip electrode 32 may be the cathode electrode by default in some examples. The bipolar BBB pacing is delivered at block 952 using a starting pulse amplitude and pulse width.

At block 954, an EGM signal is sensed for analysis and determination of bundle branch capture. In this example, sensing and analysis of unipolar EGM signals is described. However, in other examples sensing and analysis of a bipolar EGM signal may be performed for determining when bundle branch capture criteria are met, as described below in conjunction with FIG. 15. One unipolar EGM signal may be sensed at block 954 using the pacing anode electrode and the pacemaker housing (or another available reference electrode other than the pacing cathode electrode). At block 956, control circuit 80 applies bundle branch capture criteria to the unipolar EGM signal. For example, a QS complex (or in some instances a QS-r pattern) in the unipolar EGM signal may be evidence of anodal bundle branch capture at the anode electrode as the depolarization wavefront travels away from the anode electrode when capture occurs resulting in a negative deflection of the EGM signal. The QS complex detection by control circuit 80 may be based on morphological analysis, determination of the polarity of the maximum peak or other analysis of the EGM signal for detecting a QS complex. While the QS complex detection is given as one illustrative example of bundle branch capture criteria at block 956 based on a unipolar EGM signal, it is to be understood that other bundle branch capture criteria may be applied at block 956, in addition to or instead of the QS complex detection, according to any of the example capture criteria described above, such as but not limited to activation time and/or QRS signal width determined from the unipolar EGM signal sensed from the pacing anode electrode.

When control circuit 80 determines that the unipolar EGM signal sensed using the pacing anode electrode does not meet capture criteria applied at block 956, control circuit 80 may determine whether the maximum pacing output has been reached at block 958. The maximum pacing output may be the maximum programmable pulse amplitude at a selected or default pulse width, the maximum programmable pulse width at a selected or default pulse amplitude, the combination of the maximum programmable pulse amplitude available and the maximum programmable pulse width, or a predetermined or user programmed maximum pulse amplitude and maximum pulse width combination, as examples. If a maximum pulse output has not been reached, control circuit 80 may increase the pulse output at block 960, by increasing the pulse amplitude, the pulse width or both. Control circuit 80 returns to block 952 to deliver bipolar BBB pacing at the increased pacing output and sense the unipolar EGM signal from the anode electrode at block 954.

If the maximum pacing output is reached at block 958, without the capture criteria being met at block 956, control circuit 80 may switch the electrode polarity at block 964 when an alternative electrode polarity selection is available (as determined at block 962). For example, if bipolar BBB pacing is delivered by selecting the pacing tip electrode 32 as the cathode and the ring electrode 34 as the anode, control circuit 80 may pass a control signal to therapy delivery circuit 84 to switch the polarity so that the tip electrode 32 is the anode and the ring electrode 34 is the cathode.

The therapy delivery circuit 84 delivers the bipolar BBB pacing at block 952 using the switched electrode polarity assignments, and control circuit 80 applies the bundle branch capture criteria at block 956 to the unipolar EGM signal sensed using the newly selected pacing anode electrode (block 954). Control circuit 80 may control therapy delivery circuit 84 to increase the pacing pulse output as needed (block 960) until a maximum pacing output is reached or until the bundle branch capture criteria applied to the unipolar EGM signal sensed via the pacing anode electrode are reached at block 956.

If the capture criteria are unmet at block 956 and the maximum available pacing output is reached and no alternative pacing electrode polarity selection is available ("no" branch of block 962), anodal bundle branch capture is not detected at block 965. The anodal capture threshold for the corresponding bundle branch(es) is greater than the maximum available output. For example, the RBB anodal capture threshold may be greater than the maximum available pulse output when the starting bipolar BBB pacing corresponds to an anode ring electrode 34 in the right ventricular septum. If polarity switching is performed at block 964, the LBB anodal capture threshold may also be determined to be greater than the maximum pulse output. If anodal capture was not detected after switching the electrode polarities, control circuit 80 may store no anodal capture detected for the LBB and RBB or an indication that the RBB and LBB anodal capture thresholds are greater than the maximum available pacing pulse output.

When anodal capture is not achieved using a first polarity selection but is determined after switching the polarity at block 964, the anodal capture threshold for the second pacing polarity selection tested may also be stored in memory 82 at block 967. For example, control circuit 80 may generate an output stored in memory 82 at block 967 indicating that RBB anodal capture is not achieved and indicating determination of LBB anodal capture or vice versa.

Anodal bundle branch capture may be detected at block 966 in response to at least one feature of the unipolar EGM signal sensed using the anode electrode meeting bundle branch capture criteria at block 956. When anodal bundle branch capture is detected at block 966 for the first or second bipolar BBB pacing electrode polarity configuration, the anodal capture threshold may be stored at block 967 when the pacing pulse output has been increased at block 960 until the lowest pacing pulse amplitude was reached at which bundle branch capture criteria were determined to be met. If anodal capture was determined for the first test pacing pulse output setting, however, without testing lower pacing pulse output settings, the anodal capture threshold may be less than the starting pacing pulse output settings and may be unknown when anodal capture is first determined at block 966.

In other instances, the anodal capture determination at block 966 may correspond to the anodal capture threshold at the corresponding bundle branch (right or left) when the pacing output has been increased from a sub-threshold starting pacing pulse output to the lowest output at which capture criteria were met. In this case, the anodal capture threshold and the capture type, e.g., RBB or LBB, may be stored in memory 82 at block 967. Once anodal capture is determined at block 966, or when all pacing pulse output settings and available polarity selections have been exhausted without detecting anodal capture, control circuit 80 may advance to block 968 to sense the unipolar EGM signal via the pacing cathode electrode. Control circuit 80 ma determine if capture criteria are met at block 970 based on an analysis of the post-pace unipolar EGM signal sensed using the pacing cathode electrode.

Therapy delivery circuit 84 may continue delivering bipolar BBB pacing according to the most recent pacing pulse output and electrode polarity settings at which anodal capture was confirmed. If anodal capture is not detected at block 965, therapy delivery circuit 84 may decrease the pacing output parameters to starting values or continue delivering bipolar BBB pacing pulses at the current output settings. If the criteria for detecting capture of the bundle branch in the vicinity of the cathode electrode are unmet at block 970 based on an analysis of the post-pace unipolar EGM signal sensed at block 968, control circuit 80 may increase the pacing output settings at block 974 until the capture criteria are met at block 970 or until a maximum specified or maximum available pacing pulse output is reached (as determined at block 972).

When cathodal capture is not detected and the maximum pacing pulse output has been reached at block 972, control circuit 80 may determine whether an alternative electrode polarity is available at block 980. If the electrode polarity has not been switched already at block 964 to test the alternative polarity assignments of tip electrode 32 and ring electrode 34, control circuit 80 may switch the pacing electrode polarities at block 982 and return to block 952 to first verify anodal capture and then determine whether cathodal capture can be achieved within the maximum pulse output limits when the electrode polarity is reversed. In some cases, depending on electrode positioning and other factors, capture of a bundle branch in the vicinity of a given electrode may be achieved at a lower pacing pulse output for a given polarity assignment.

When capture criteria are met at block 970, control circuit 80 detects cathodal bundle branch capture of the corresponding bundle branch at block 978. In some examples, control circuit 80 may determine if other test pacing parameter settings are available at bock 980. For example, if both anodal capture and cathodal capture were detected at the starting pacing pulse output, control circuit 80 may determine that a lower pacing pulse output may be available for testing in order to determine the capture threshold. The pacing output may be adjusted at block 982 by reducing the pacing pulse output (e.g., the pacing pulse amplitude and/or pulse width) to redetermine whether anodal capture is still detected and subsequently whether cathodal capture is still detected.

In other examples, control circuit 80 may determine whether an alternative electrode polarity is available at block 980 after determining cathodal capture at block 978. For example, if the alternative electrode polarity has not been already tested by switching polarity at block 964, the polarity may be switched at block 982. The process may return to block 952 to repeat analysis of the two unipolar EGM signals for detecting anodal capture and cathodal capture according to the alternative polarity selection as described above. In this way, control circuit 80 may be configured to determine the lowest pacing output for achieving bipolar BBB pacing capture according to two different electrode polarity selections using the same electrode pair by determining the lowest pacing output at which both anodal capture and cathodal capture occur at each of tip electrode 32 and ring electrode 34.

If anodal and cathodal capture have been detected and/or no other test parameters are available for determining capture threshold for both electrodes, control circuit 80 may advance to block 984 to store the capture thresholds and associated capture type. In some examples, the bipolar BBB pacing capture threshold is determined and stored for a given electrode polarity selection, e.g., tip electrode 32 as the cathode and ring electrode 34 as the anode. The cathodal capture threshold and the anodal capture threshold may each be stored, with the higher of the two being the bipolar BBB pacing capture threshold for the given electrode polarity selection. When more than one electrode polarity selection is tested, the bipolar BBB pacing capture threshold for the second electrode polarity selection, e.g., tip electrode 32 as the anode and ring electrode 34 as the cathode, may be stored in memory 82 at block 984. The capture threshold corresponding to both cathodal capture and anodal capture for each electrode of a bipolar pair may be stored at block 984.

When multiple electrodes are available for selecting a bipolar electrode vector, for example when lead 18 is a quadripolar leads including four electrodes as shown in FIG. 2C, control circuit 80 may select a different pair of electrodes as a bipolar BBB pacing electrode vector at block 982. A different pair of electrodes, e.g., electrode 32 and electrode 42, electrode 32 and electrode 44, or electrode 34 and 44, etc., may be selected at block 982. In the example of FIG. 2C, for example, six different pairs of electrodes may be selected from the four available electrodes 32, 34, 42 and 44. Furthermore, the anode and cathode polarities may be switched for each pair for testing two different anode and cathode electrode assignments for each possible pair, for a total of twelve different pacing electrode configurations for bipolar BBB pacing. In some examples, the number of pacing electrode configurations tested may be limited and or selection of new pacing electrode configurations may be stopped when cathodal and anodal pacing capture is determined within an acceptable maximum pacing pulse output.

The capture threshold information stored at blocks 966 and 984 may be used by control circuit 80 in selecting pacing control parameters at block 986. Control circuit 80 may select the electrode vector and electrode polarity that results in the lowest bipolar BBB pacing capture threshold and set the pacing pulse output to a safety margin greater than the capture threshold. When anodal capture is not achieved, control circuit 86 may select single bundle branch pacing, either LBB or RBB pacing, and assign the electrode in the area of the LBB or RBB location to be the cathode electrode. The pacing output may be set by control circuit 80 to be a safety margin greater than the cathodal capture threshold in this case. At block 988, therapy delivery circuit 84 generates and delivers bundle branch pacing pulses according to the selected electrode polarity and pacing pulse output parameters.

In some examples the QRS signals of the ECG and/or EGM signals may present greater improvement (e.g., most closely resembling normal conduction along the native conduction system) during LBB only capture compared to RBB only capture or vice versa when the bipolar BBB pacing capture threshold is unacceptably high. In other instances, BBB capture may not present greater ventricular electrical synchrony improvement than LBB only capture. For example, when the LBB pacing pulse is delivered at an appropriate or optimized AV delay and scheduled to cause fusion with any intrinsic bundle branch depolarization, e.g., fusion with RBB activation when RBB block is not present, LBB pacing only may provide optimal improvement in ventricular synchrony. A trade-off may exist in conserving pacemaker power source 98 and achieving BBB capture. When bipolar BBB pacing cannot be achieved, or the bipolar BBB capture threshold is relatively high, resulting in an unacceptable decrease in predicted pacemaker longevity (until the end of the useful life of power source 98), LBB only pacing or RBB only pacing may be selected by control circuit 80 based on determining EGM signal features that result in the most normal physiological QRS signal, e.g., narrowest QRS width, shortest interventricular activation delay, or other criteria. Techniques for selecting an optimal pacing electrode configuration and pacing output control parameters are described below in conjunction with FIG. 16.

While the process of FIG. 14 shows analyzing the unipolar EGM signal for first detecting anodal bundle branch capture in a first side of the septum and analyzing the unipolar EGM signal for detecting cathodal bundle branch capture in a second side of the ventricular septum after determining anodal capture, it is to be understood that sensing and analysis of the EGM signals for detecting cathodal capture and anodal capture, corresponding to LBB capture and RBB capture or vice versa, may be performed in any order or in an interwoven or simultaneous, parallel manner and is not required to be performed in any given specific sequence as described for the sake of convenience herein. For example, at a given pacing pulse output, control circuit 80 may analyze each of the unipolar EGM signals to determine whether capture is occurring at the anode and cathode then increase the pacing pulse output as needed until capture is detected at both electrodes. If a maximum pulse output is reached, the polarity may be switched and the pulse amplitude and/or pulse width may be adjusted until the lowest pacing output at which both anodal and cathodal capture is determined. The pacing pulse output may be started at a relatively low or minimum output and increased until both anodal and cathodal capture are detected from the unipolar EGM signals. Alternatively, the pacing pulse output may be started at a relatively high or maximum output and decreased until anodal loss of capture and/or cathodal loss of capture is/are detected from the unipolar EGM signals. The lowest output at which both anodal and cathodal capture occurs may be stored as the BBB capture threshold.

Figure 15:
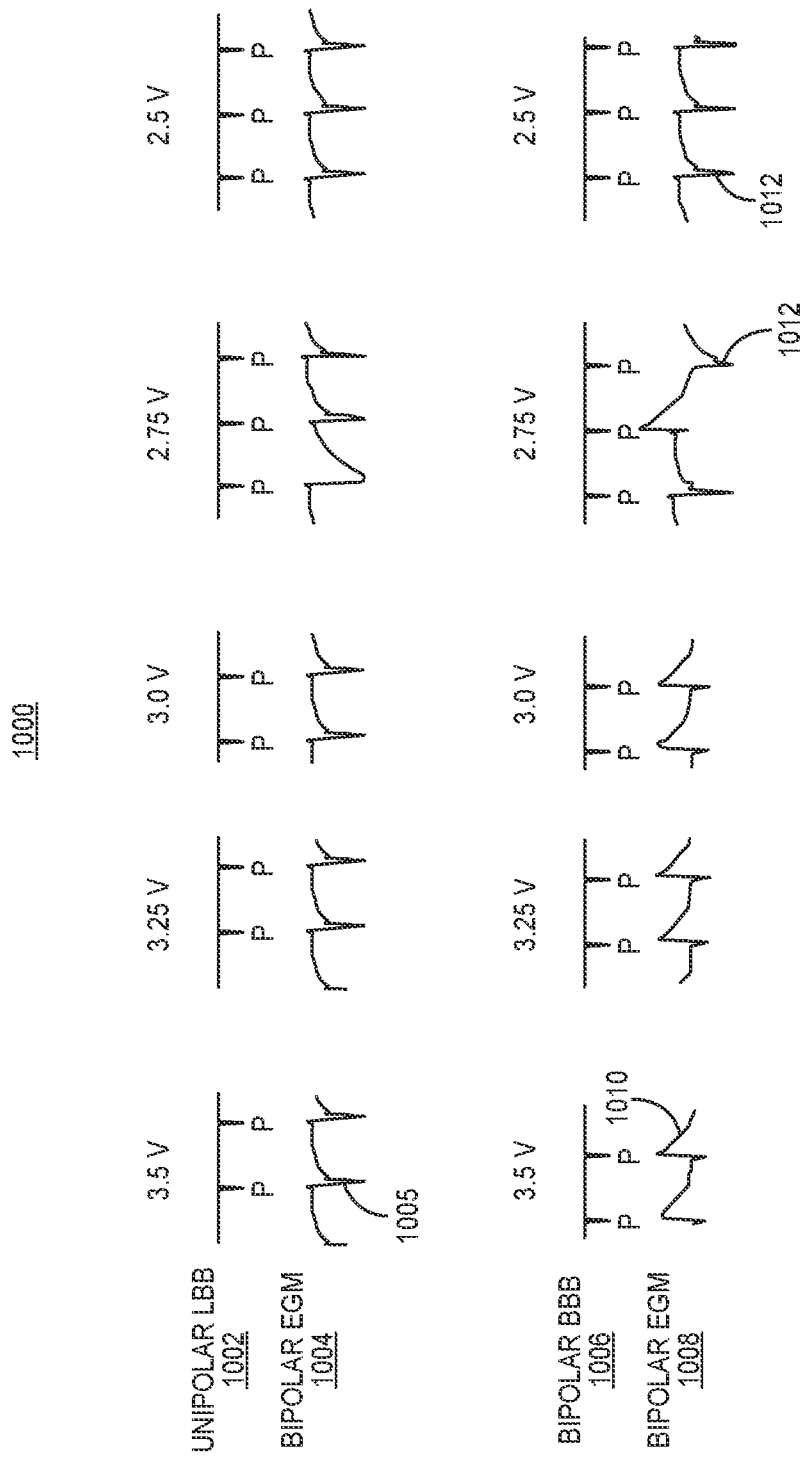
FIG. 15 is a diagram of pacing signals and bipolar EGM signals illustrating a method for detecting capture during bipolar BBB pacing according to another example.

FIG. 15 is a diagram 1000 of delivered pacing pulses 1002 and 1006 and bipolar EGM signals 1004 and 1008 illustrating a method for detecting bipolar BBB capture, including anodal and cathodal capture, according to another example. The BBB capture detection methods described in conjunction with FIG. 15 may be used, for example, at block 906 of FIG. 13 and may be used in addition to or instead of the unipolar EGM signal analysis described above in conjunction with FIGS. 11 and 12. For the sake of convenience, a method is described in conjunction with FIG. 15 as being performed by control circuit 80 using bipolar EGM signals sensed by sensing circuit 86 during pacing delivered by therapy delivery circuit 84. It is to be understood however, that the bipolar EGM signals 1004 and 1008 shown in FIG. 15 may be received by external device processor 52, e.g., from pacemaker 14 via telemetry unit 58 or from lead 18 via interface 51 during delivery of pacing pulses 1002 and 1006 by therapy delivery circuit 84 or by external pulse generator 60.

Control circuit 80 may control therapy delivery circuit 84 to select a unipolar LBB pacing electrode configuration, e.g., including tip electrode 32 as the cathode electrode with pacemaker housing 15 as the return anode. Therapy delivery circuit 84 may generate and deliver the unipolar LBB only pacing pulses 1002 at multiple pacing pulse output settings. In the example shown, therapy delivery circuit 84 generates the unipolar LBB pacing pulses 1002 at a starting pulse amplitude of 3.5 volts and decreases the pacing pulse amplitude to 2.6 volts in 0.25 volt decrements under the control of control circuit 80. In other examples, therapy delivery circuit 84 may progressively increase the pacing pulse amplitude, randomly vary the pacing pulse amplitude, progressively increase or decrease the pacing pulse width or randomly vary the pacing pulse width. The bipolar EGM signal 1004 is sensed by sensing circuit 86 during pacing pulse delivery. The bipolar EGM signal may be sensed between tip electrode 32 and ring electrode 34. As observed in FIG. 15, QRS signal 1005 in the bipolar EGM signal during unipolar LBB pacing is observed as a narrow, negative going signal at all pacing pulse outputs tested in the example shown.

Control circuit 80 may store one or more determined features from the bipolar EGM signal 1004 during unipolar LBB only pacing that is/are representative of LBB capture (without RBB capture). Control circuit 80 may determine and store the polarity (positive or negative) of the evoked QRS signal 1005, the QRS width, the QRS area, or an overall morphology (e.g., based on a time frequency transform such as a wavelet transform or other morphology analysis), as examples.

Under the control of control circuit 80, therapy delivery circuit 84 may generate and deliver bipolar BBB pacing pulses 1006 using the tip electrode 32 (as the cathode in this example) and the ring electrode 34 (as the anode in this example) at different pacing pulse outputs. Control circuit 80 may determine one or more characteristic features of the bipolar EGM signal 1008 received from sensing circuit 86 and sensed between the tip electrode 32 and the ring electrode 34 during the bipolar pacing. In the example shown, therapy delivery circuit 84 delivers bipolar pacing pulses starting at 3.5 volts and decreases the pulse amplitude by 0.25 volts decrements down to 2.5 volts.

As observed, control circuit 80 may determine a positive polarity, relative wide QRS width, or large QRS area of the evoked QRS signal 1010 at relatively high pacing pulse outputs (3.0 to 3.5 volts). The overall QRS waveform morphology may be determined in some examples, e.g., by generating a waveform template based on amplitudes or performing a wavelet transform or other time-frequency analysis or other morphology analysis techniques.

Beginning at the pulse amplitude of 2.75 volts, and more consistently at the pulse amplitude of 2.5 volts, the QRS waveform changes from the positive, wide QRS signal 1010 to the negative narrow QRS signal 1012. This change to the negative, narrow QRS signal 1012 is consistent with LBB only capture (shown above) and evidence of loss of anodal capture of the RBB at the lower pacing pulse amplitudes (e.g., 2.5 volts). Control circuit 80 may be configured to detect the change in QRS polarity, change in QRS width, change in QRS area, or overall change in QRS morphology, as examples, for detecting loss of anodal capture when the starting pacing pulse output is high and is progressively decreased.

Determination of the evoked QRS waveform feature(s) during unipolar LBB pacing may be optional. In some examples, control circuit 80 may compare the determined QRS features during bipolar pacing to the reference QRS signal feature(s) determined during unipolar LBB pacing to verify RBB anodal capture at relatively higher pacing pulse output based on a QRS signal difference (in polarity, width, area, etc.) and verify RBB loss of capture (at lower pacing pulse output) based on no difference in the bipolar EGM QRS signal during BBB pacing compared to evoked response QRS signal during the unipolar LBB pacing.

In other examples, however, therapy delivery circuit 84 may be controlled by control circuit 80 to deliver bipolar BBB pacing pulses 1006 at progressively increasing (or decreasing) pacing pulse amplitude and detect a change in one or more QRS signal features as evidence of a change from anodal bundle branch loss of capture to anodal bundle branch capture (or from capture to loss of capture). Anodal bundle branch capture may be determined in response to the bipolar EGM signal morphology changing from a first morphology, e.g., the morphology of the bipolar EGM signal 1012 in FIG. 15, to a second morphology, e.g., the QRS signal morphology 1010 to the RBB capture criteria. Control circuit 80 may determine the anodal capture threshold of the RBB (or LBB when the polarity of tip electrode 32 and ring electrode 34 is reversed) when the morphology change is detected and thus determine the bipolar BBB pacing capture threshold. In the example of FIG. 15, the bipolar BBB pacing capture threshold may be determined by control circuit 80 to be 3.0 volts since anodal capture was intermittent during pacing at 2.75 volts (as evidenced by both positive and negative polarity QRS signals) and anodal capture was lost at 2.5 volts (as evidenced by only negative, narrow QRS signals). Control circuit 80 may select a bipolar pacing electrode configuration with the pacing pulse amplitude set to at least 3.0 V or higher to provide a pacing safety margin above the capture threshold.

Figure 16:
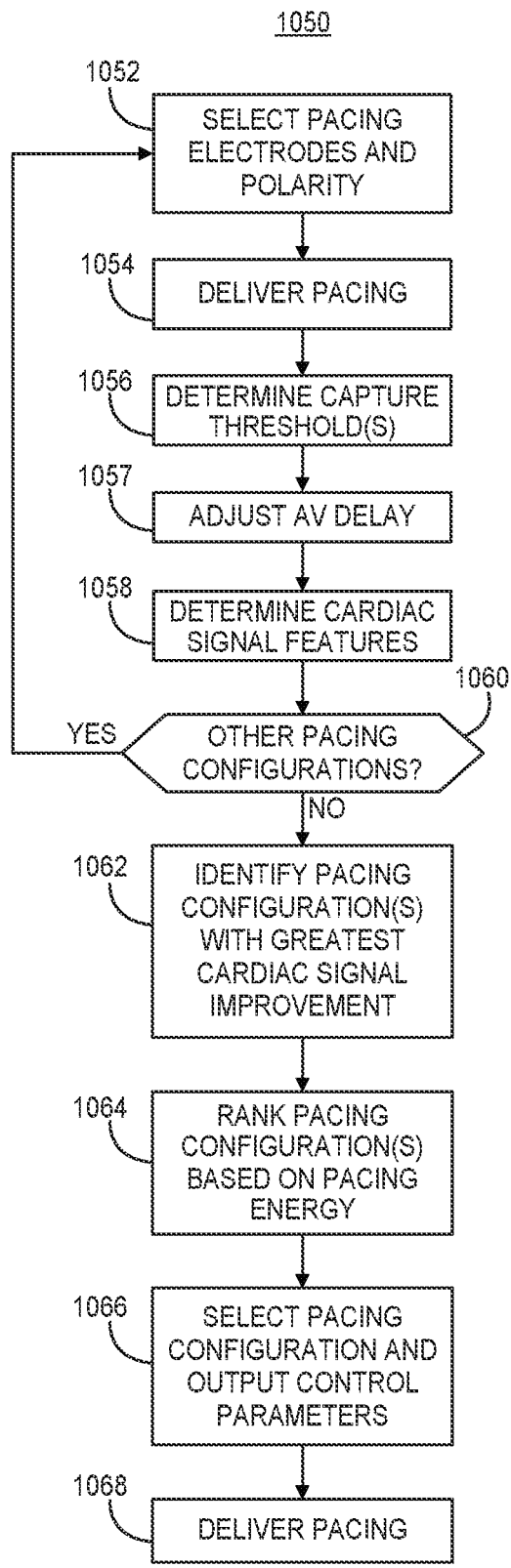
FIG. 16 is a flow chart of a method for selecting a pacing electrode configuration for bundle branch pacing according to one example.

FIG. 16 is a flow chart 1050 of a method for selecting a pacing electrode configuration according to one example. The process of flow chart 1050 may be executed by external device processor 52 or pacemaker control circuit 80 or a combination of both in a cooperative manner. The process of flow chart 1050 includes selecting a pacing electrode configuration at block 1052 by selecting electrodes and electrode polarities for delivering bundle branch pacing. For the sake of illustration, the first electrode configuration may be the bipolar BBB pacing configuration using the tip electrode 32 selected as the cathode electrode and the ring electrode 34 as the anode electrode for cathodal capture of the LBB and anodal capture of the RBB.

At block 1054, therapy delivery circuit 84 (or external device pulse generator 60) generates pacing pulses delivered according to the selected pacing electrode configuration. At block 1056, control circuit 80 adjusts the pacing pulse amplitude and/or width to determine the pacing capture threshold(s) for the selected pacing electrode configuration. In the illustrative example of the starting configuration being bipolar BBB pacing with cathodal pacing of the LBB and anodal pacing of the RBB, control circuit 80 may execute a capture threshold search to determine the anodal capture threshold, the cathodal capture threshold and the bipolar BBB capture threshold being the higher one of the anodal and cathodal capture thresholds. Techniques described above in conjunction with FIGS. 14 and 15 may be used to search for the capture thresholds associated with the bipolar BBB pacing configuration. At block 1056, the determined capture thresholds may be stored in memory 82. When the process of flow chart 1050 is performed all or in part by external device processor 52, it is understood that the capture thresholds may be determined at block 1056 based on determining and analyzing ECG signal features or a combination of EGM and ECG signal features. Any of the example capture detection criteria described above may be utilized by the processor 52 or control circuit processor 148 for determining capture thresholds at block 1056.

During the pacing capture threshold test, the pacing pulses may be delivered at a premature pacing interval, e.g., a shortened AV delay or overdrive ventricular pacing rate. After determining the capture threshold(s), control circuit 80 may adjust the AV delay at block 1057 when dual chamber sensing is available for synchronizing the ventricular pacing pulses to atrial pace or sense events. Control circuit 80 may adjust the AV delay at block 1057 so that cardiac signal features determined at block 1058 as described below are determined when the bundle branch pacing pulse is delivered at an appropriate or optimized AV delay from a preceding atrial P-wave or atrial pacing pulse. Example techniques for adjusting the AV delay are generally disclosed in U.S. Patent Publication No. 2019/0111264 (Zhou), incorporated herein by reference in its entirety. In some examples, the AV delay may be adjusted to different settings at block 1057 by control circuit 80. Control circuit 80 may determine an EGM signal QRS width at each AV delay setting. Control circuit may determine which AV delay the QRS width is narrowest and select the AV delay as the optimal AV delay setting. When the AV delay is optimized, particularly when only the LBB or only the RBB is being paced, the bundle branch pacing evoked responses are expected to fuse with any intrinsic electrical conduction along the His-Purkinje system. In other examples, control circuit 80 may withhold pacing for at least one cycle and determine a time interval from an atrial event (sensed or paced) to an intrinsic QRS. The AV delay may be set based on this intrinsic AV time interval to promote fusion between a delivered pacing pulse and the intrinsic QRS.

Control circuit 80 may determine cardiac signal features at block 1058 that correspond to pacing using the selected pacing electrode configuration, an optimized AV delay and a pacing pulse output that is equal to or greater than the determined capture threshold. The cardiac signal features determined at block 1058 may include QRS width and/or RV activation time determined from the unipolar EGM signal sensed using the ring electrode 34, the QRS width and/or LV activation time determined from the unipolar EGM signal sensed using the tip electrode 32, a difference between RV and LV activation times determined from the unipolar EGM signals, and/or the QRS maximum peak amplitude determined from the bipolar EGM signal sensed between the tip electrode 32 and ring electrode 34. One or more cardiac signal features may be determined to represent a metric of ventricular electrical synchrony. The one or more cardiac signal features determined at block 1058 may be stored in memory 82 in association with the current pacing configuration and associated capture threshold(s).

At block 1060, control circuit 80 (or external device processor 52) determines whether additional pacing configurations are available. If so, control circuit 80 may return to block 1052 and select a different pacing configuration, which may include different pacing electrodes and/or polarity assignments. In the illustrative example of the first pacing configuration being a bipolar configuration with the cathode electrode in the area of the LBB, the second pacing configuration may be a bipolar pacing configuration with the cathode electrode in the area of the RBB (e.g., ring electrode 34) and the anode electrode in the area of the LBB (e.g., tip electrode 32). Control circuit 80 or external device processor 52 repeats the process of blocks 1054 through 1058 for determining and storing associated capture thresholds and cardiac signal features for the second pacing electrode configuration.

At block 1060, control circuit 80 may determine that a third pacing configuration is available, e.g., unipolar pacing of each of the RBB and LBB. The tip electrode 32 may be selected at block 1052 as a unipolar pacing cathode electrode paired with the pacemaker housing 15 for LBB pacing. The ring electrode 34 may be selected at block 1052 as a unipolar pacing cathode electrode also paired with the pacemaker housing 15 for RBB pacing. In this way, dual unipolar BBB pacing may be delivered. In other examples, the dual unipolar BBB pacing configurations may include using a defibrillation coil electrode 35 instead of the pacemaker housing 15. In the dual unipolar BBB pacing configuration, the two unipolar pacing electrode vectors may share a common anode electrode or two different anode electrodes may be used. In some cases, a single unipolar pacing electrode configuration may achieve BBB capture. Accordingly, a pacing configuration may be selected as a single unipolar pacing electrode configuration to determine if RBB pacing capture, LBB pacing capture, or both RBB and LBB pacing capture is achieved.

After selecting a dual unipolar BBB pacing electrode configuration, control circuit determines the unipolar RBB capture threshold and the unipolar LBB capture threshold at block 1056 by controlling therapy delivery circuit 84 to deliver pacing pulses (block 1054) at a shortened AV delay or overdrive pacing rate and according to different pacing pulse output settings to each of the RBB cathode electrode and the LBB cathode electrode. The unipolar pacing capture threshold test may be performed sequentially for RBB pacing and for LBB pacing while pacing to the opposite bundle branch is withheld. In other examples, bilateral pacing may be delivered as the pacing output is simultaneously increased (or decreased) to both bundle branches. Control circuit 80 may determine the lowest pacing output at which each bundle branch is captured. For instance, control circuit 80 may detect RBB capture in response to detecting a shortened RV activation time from a RBB unipolar EGM signal sensed by sensing circuit 86. Control circuit 80 may detect LBB capture in response to a shortened LV activation time from a unipolar LBB EGM signal. Control circuit 80 may detect BBB capture when the activation time difference decreases (between two unipolar EGM signals) or a bipolar EGM morphology change is detected, as examples. When both the RBB and LBB are paced in unison using the unipolar pacing electrode vectors, a decrease in the QRS width and/or decrease in the activation time difference may be detected for detecting unipolar BBB pacing capture. As described above, the determination of capture thresholds may be performed in whole or in part based on an analysis of ECG signals by external device processor 52 in some examples, e.g., by detecting an LBB block pattern during RBB pacing and detecting a RBB block pattern during LBB pacing.

After achieving unipolar BBB pacing capture, control circuit 80 (and/or external processor 52) may adjust the AV delay at block 1057 as described above and determine cardiac signal features at block 1058 for storage in memory 82 in conjunction with the dual unipolar BBB pacing electrode configuration capture thresholds. It is recognized that in some examples, the cardiac signal features determined at block 1058 may include cardiac signal features determined at block 1056 in the process of determining capture thresholds. For example, a maximum amplitude, QRS width and/or activation time difference may be determined for verifying BBB pacing capture. The maximum amplitude, QRS width and/or activation time difference may be stored as the cardiac signal features associated with the dual unipolar BBB pacing electrode configuration.

After storing the cardiac electrical signal features at block 1058, control circuit may select a different pacing electrode configuration at block 1060. Other pacing electrode configurations that may be selected at block 1060 may include only LBB pacing using a unipolar pacing electrode configuration, only LBB pacing using a bipolar pacing electrode configuration (no anodal capture), only RBB pacing using a unipolar pacing electrode configuration, only RBB pacing using a bipolar pacing electrode vector (no anodal capture). In some examples, when two bipolar leads are placed in the interventricular septum, e.g., a bipolar lead in the right septum in proximity to the RBB and a bipolar lead in the left septum in proximity to the LBB as shown in FIG. 2B, or when a quadripolar lead is positioned in the septum to position one bipolar electrode pair near the LBB and one bipolar electrode pair near the RBB (see FIG. 2C), each of the RBB and the LBB may be paced individually by two different bipolar electrode pairs in yet another pacing electrode configuration selection. The BBB pacing capture threshold in the case of dual bipolar pacing electrode vectors may be determined at block 1056 as the higher one of the RBB capture threshold and the LBB capture threshold.

In still other examples, other pacing configurations identified at block 1060 may include electrodes positioned for ventricular myocardial pacing. For example, a coronary sinus lead may be advanced within a cardiac vein to a position along the left ventricle for pacing the LV myocardium (see FIG. 2D). In some examples, electrodes may be implanted along the RV apex or in the interventricular septum which may enable pacing and capture of the RV myocardium (see FIG. 2D). Accordingly, in some examples, a pacing electrode configuration selected at block 1052 may include one or more pacing electrode vectors for pacing the RBB and/or the LBB in combination with one or more pacing electrode vectors for pacing the LV myocardium and/or the RV myocardium. The capture thresholds which may be determined and stored at block 1056 may correspond to LBB capture, RBB capture, BBB capture, LV myocardial capture, and/or RV myocardial capture or any combination thereof. For a given combination of LBB capture, RBB capture, BBB capture, LV myocardial capture and/or RV myocardial capture, different pacing configurations may be available, including different unipolar and/or bipolar electrode configurations with different selectable electrode polarity assignments. The pacing capture thresholds for each pacing location associated with each of the available test pacing electrode configurations (and polarity assignments) may be stored in memory 82 (or external device memory 53).

EGM and/or ECG signal analysis may be performed to determine cardiac signal features during bipolar BBB pacing, RBB only pacing, LBB only pacing, dual unipolar BBB pacing, dual bipolar BBB pacing, BBB+RV myocardial pacing, BBB+LV myocardial pacing, LBB+LV myocardial pacing, RBB+LV myocardial pacing, LBB+RV myocardial pacing, RBB+RV myocardial pacing signal, etc., depending in part on the lead/electrode configurations available. In some examples, pacing electrode configurations may include housing-based electrodes 132 and 134 of a leadless pacemaker. The cardiac signal features determined and stored at block 1058 may include any of the signal features described herein including, but not limited to, RV activation time, LV activation time, interventricular (e.g., RV to LV) activation time difference, overall QRS morphology, evidence of RBB block pattern, evidence of LBB block pattern, QRS width, QRS area, number of peaks, peak-to-peak amplitude, QS pattern, or other feature determined from one or more ECG signal vectors and/or one or more EGM signals (unipolar and/or bipolar) received by a processor, e.g., of control circuit 80 and/or external device processor 52.

After acquiring capture threshold results and cardiac signal features for each tested pacing electrode configuration, an optimal pacing electrode configuration may be determined by the control circuit processor 148 or external device processor 52 that provides the most physiologically normal cardiac electrical signal (e.g., based on narrow QRS width and minimized interventricular activation time difference) and a pacing pulse output within acceptable pacing capture threshold limits or a total pacing energy required for delivering pacing pulses to multiple pacing sites within a total pacing energy limit.

At block 1062, control circuit 80 may identify a pacing electrode configuration having the greatest cardiac signal feature improvement. Control circuit 80 may rank tested pacing electrode configurations according to QRS width, interventricular activation time difference, bipolar EGM QRS amplitude or other cardiac signal features. For example, the pacing electrode configuration having the narrowest QRS width, shortest (or zero) interventricular activation time difference, and/or lowest bipolar EGM R-wave amplitude may be identified at block 1062 as the pacing electrode configuration associated with the greatest cardiac signal improvement representing the most physiologically, normal conduction and synchronized ventricular electrical activation. A ranking of the tested pacing electrode configurations may be determined based on cardiac signal features that may be evaluated individually or in combination or in weighted combinations, which may include determining relative differences or changes in the cardiac signal features compared to no pacing or compared to a selected reference pacing electrode configuration.

At block 1064, control circuit 80 may compare the pacing pulse output of the pacing electrode configuration(s) identified to have the greatest cardiac signal feature improvement. When multiple pacing electrode configurations result in the same or equivalent cardiac signal features corresponding to the greatest improvement in ventricular electrical synchrony, the pacing electrode configuration requiring the least pacing energy may be determined at block 1064. For example, depending on the capture thresholds, a bipolar BBB pacing configuration that includes anodal and cathodal capture may require lower pacing energy than delivering two unipolar or two bipolar pacing pulses to the LBB and RBB for achieving BBB pacing and may provide greater electrical RV and LV synchrony than pacing either the RBB or LBB alone. The pacing pulse energy required to deliver pacing pulses according to a selected pacing electrode configuration includes the pacing pulse output used to generate each pacing pulse delivered by each pacing electrode vector included in the pacing electrode configuration. If the same or similar cardiac signal features are determined during bipolar BBB pacing (with anodal and cathodal capture using a single pacing pulse) as the cardiac signal features determined during BBB pacing using two different bipolar or unipolar pacing electrode vectors for capturing the RBB and LBB, the bipolar BBB configuration may be the optimal pacing electrode configuration. The bipolar BBB pacing configuration may be selected by control circuit 80 at block 1066 and the pacing electrode polarity and pacing pulse amplitude and width may be set based on the stored pacing capture thresholds determined for bipolar BBB pacing.

However, when anodal capture cannot be achieved or the bipolar BBB pacing capture threshold is unacceptably high, or the bipolar BBB pacing configuration does not result in the greatest cardiac signal feature improvement, an alternative pacing electrode configuration having lower pacing energy requirements and/or greater cardiac signal feature improvement may be selected at block 1066. The pacing energy requirement for a given pacing electrode configuration may be determined by control circuit 80 to be unacceptably high when the pacing capture amplitude is greater than a predetermined amplitude, e.g., greater than 3 V, 4 V, or 5 V as examples. Alternatively, control circuit 80 may determine the pacing energy requirement is unacceptable when the pacing capture amplitude is greater than a predetermined percentage higher than other pacing configuration capture threshold amplitudes, e.g., more than double or more than 50% higher than other pacing electrode configurations. In some examples, pacing of a single bundle branch, e.g., LBB only pacing or RBB only pacing, may result in similar improvements in cardiac signal features indicative of improved ventricular electrical synchrony compared to BBB pacing and require much less pacing energy. In this case, single bundle branch pacing, e.g., LBB only pacing, may be selected at block 1066 as the optimal pacing configuration.

Control circuit 80 may be configured to select a pacing electrode configuration, electrode polarity assignments, and pacing pulse amplitude and pulse width based on the cardiac signal features and capture thresholds determined for each of the tested pacing electrode configurations. In other examples, external device processor 52 may generate data representing the cardiac signal features and pacing capture thresholds determined for each tested pacing electrode configuration and generate a display on display unit 54. A user may review the displayed data for selecting and programming a pacing electrode configuration and pacing pulse output parameters for achieving an optimal tradeoff between maximizing electrical synchrony of the ventricles and minimizing the pacing energy required (to thereby conserve the useful life of power source 98). At block 1068, therapy delivery circuit 84 delivers ventricular pacing according to the selected pacing electrode configuration and pacing pulse output control parameters.

In various examples presented herein, one or more EGM signals may be analyzed for detecting BBB capture according to any of the examples presented above which may include determining one or more of QRS duration, LV activation time from a pacing pulse to a QRS peak, RV activation time from a pacing pulse to a QRS peak (or other fiducial point of the QRS signal), interventricular activation time difference (difference between RV and LV activation time), as examples. A change or increase in an EGM feature corresponding to worsening ventricular electrical synchrony may be detected by pacemaker control circuit 80 as a loss of capture detection during any of the capture monitoring techniques described above. The loss of capture detection may be loss of LBB capture during BBB pacing, loss of RBB capture during BBB pacing and/or total loss of RBB and LBB capture in various examples.

Detection of any type of loss of capture by control circuit 80 during BBB pacing may be responded to by the control circuit 80 by adjusting the pacing pulse output which may include increasing pacing pulse amplitude, increasing pacing pulse width, switching electrode polarity, and/or changing pacing pulse shape. When BBB pacing capture cannot be achieved, e.g., after a maximum number of attempts, a different pacing configuration may be selected based on the cardiac signal feature improvement and pacing energy requirements previously determined at blocks 1062 and 1064.

It should be understood that, depending on the example, certain acts or events of any of the methods described herein can be performed in a different sequence, in parallel, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single processor, circuit or unit for purposes of clarity, it should be understood that the techniques of this disclosure may be performed by a combination of processors, units or circuits associated with, for example, a medical device system.

In one or more examples, the functions described may be implemented in hardware, software, firmware, or any combination thereof. If implemented in software, the functions may be stored as one or more instructions or code on a computer-readable medium and executed by one or more hardware-based processing units. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system, comprising:
   a pulse generator configured to generate pacing pulses;
   a sensing circuit for sensing a first cardiac electrical signal; and
   processing circuitry configured to:
   receive at least the first cardiac electrical signal that is sensed by the sensing circuit during bilateral bundle branch pacing delivered from the pulse generator via a bipolar electrode pair comprising an anode positioned along a first bundle branch and a cathode positioned along a second bundle branch opposite the first bundle branch;
   determine at least one feature from the first cardiac electrical signal;
   determine that the at least one feature meets first bundle branch capture criteria indicating that the bilateral bundle branch pacing has captured the first bundle branch; and
   determine anodal bundle branch capture in response to the first bundle branch capture criteria being met; and
   determine a pacing pulse output based on determining the anodal bundle branch capture; and
   control the pulse generator to generate pacing pulses according to the determined pacing pulse output.

2. The medical device system of claim 1, wherein the processing circuitry is further configured to:
   determine the pacing pulse output for bilateral bundle branch pacing in response to determining the anodal bundle branch capture.

3. The medical device system of claim 1, wherein the processing circuitry is configured to:
   determine the at least one feature from the first cardiac electrical signal by determining at least one of a QRS width, a QRS amplitude, a QRS morphology, a QRS polarity, and an activation time.

4. The medical device system of claim 1, wherein the sensing circuit is further configured to:
   receive the first cardiac electrical signal as a first unipolar signal via a first one of the anode and the cathode as a sensing electrode.

5. The medical device system of claim 4, wherein:
   the sensing circuit is configured to receive a second cardiac electrical signal as a second unipolar signal via a second one of the anode and the cathode; and
   the processing circuitry is configured to determine the at least one feature by determining an activation time difference as a time interval between the first feature of the first cardiac electrical signal and a second feature of the second cardiac electrical signal; and
   determine that the activation time difference meets the first bundle branch capture criteria.

6. The medical device system of claim 1, wherein the sensing circuit is further configured to pass at least the first cardiac electrical signal to the processing circuitry by sensing a bipolar signal via the anode and the cathode.

7. The medical device system of claim 6, further comprising:
   the pulse generator configured to generate pacing pulses delivered via the anode and the cathode at each of a plurality of pacing pulse outputs;
   wherein the processing circuitry is further configured to:
   determine the at least one feature from the first cardiac electrical signal by:
      determining, from the bipolar signal, a first QRS morphology corresponding to a first pacing pulse output of the plurality of pacing pulse outputs;
      determining, from the bipolar signal, a second QRS morphology corresponding to a second pacing pulse output of the plurality of pacing pulse outputs, wherein the second pacing pulse output is greater than the first pacing pulse output and the second QRS morphology is different than the first QRS morphology; and
      detecting in the bipolar signal a change between the first QRS morphology and the second QRS morphology; and
   determine that the at least one feature meets the first bundle branch capture criteria in response to detecting the change in the bipolar signal between the first QRS morphology and the second QRS morphology.

8. The medical device system of claim 1, further comprising:
the pulse generator further configured to:
generate a unipolar pacing pulse delivered via the cathode; and
generate a bipolar pacing pulse delivered via the cathode and the anode;
the sensing circuit further configured to sense at least the first cardiac electrical signal by:
receiving the first cardiac electrical signal as a first unipolar signal via the anode; and
receiving a second cardiac electrical signal as a second unipolar signal via the cathode; and
wherein the processing circuitry is further configured to:
determine, from the first unipolar signal and the second unipolar signal following the unipolar pacing pulse, a first activation time difference from a first fiducial point of the first unipolar signal to a second fiducial point of the second unipolar signal;
determine, from the first unipolar signal and the second unipolar signal following the bipolar pacing pulse, a second activation time difference from the first fiducial point of the first unipolar signal to the second fiducial point of the second unipolar signal;
determine that the second activation time difference is less than the first activation time difference; and
determine that the at least one feature meets the first bundle branch capture criteria in response to the second activation time difference being less than the first activation time difference.

9. The medical device system of claim 8, wherein:
the pulse generator is configured to deliver a bipolar pacing pulse via the anode and the cathode at each of a plurality of pacing pulse outputs;
the processing circuitry is further configured to:
determine a first lowest pacing pulse output of the plurality of pacing pulse outputs that is associated with anodal bundle branch capture being determined in response to the first bundle branch capture criteria being met;
determine a bipolar bilateral bundle branch pacing capture threshold as the first lowest pacing pulse output of the plurality of pacing pulse outputs;
set the pacing pulse output based on the bipolar bundle branch pacing capture threshold; and
control the pulse generator to deliver bilateral bundle branch pacing by delivering bipolar pacing pulses at the pacing pulse output for capturing the first bundle branch via the anode and the second bundle branch via the cathode.

10. The medical device system of claim 9, wherein the processing circuitry is further configured to:
determine that the bipolar bilateral bundle branch capture threshold is greater than a maximum pacing output limit;
determine a second lowest pacing pulse output of the plurality of pacing pulse outputs that is associated with the second cardiac electrical signal meeting second bundle branch capture criteria; and
setting the pacing pulse output based on the second lowest pacing pulse output that is associated with the second cardiac electrical signal meeting second bundle branch capture criteria; and
control the pulse generator to deliver single bundle branch pacing by delivering pacing pulses at the pacing pulse output for capturing the second bundle branch via the cathode.

11. A method, comprising:
receiving at least a first cardiac electrical signal that is sensed during bilateral bundle branch pacing delivered from a bipolar electrode pair comprising an anode positioned along a first bundle branch and a cathode positioned along a second bundle branch opposite the first bundle branch;
determining at least one feature from the first cardiac electrical signal;
determining that the at least one feature meets first bundle branch capture criteria indicating that the bilateral bundle branch pacing has captured the first bundle branch;
determining anodal bundle branch capture in response to the first bundle branch capture criteria being met;
determining a pacing pulse output based on determining the anodal bundle branch capture; and
generating pacing pulses according to the determined pacing pulse output.

12. The method of claim 11, further comprising:
determining the pacing pulse output for bilateral bundle branch pacing in response to determining the anodal bundle branch capture.

13. The method of claim 11, further comprising:
determining the at least one feature from the first cardiac electrical signal by determining at least one of a QRS width, a QRS amplitude, a QRS morphology, a QRS polarity, and an activation time.

14. The method of claim 11, further comprising receiving the first cardiac electrical signal as a first unipolar signal via a first one of the anode and the cathode as a sensing electrode.

15. The method of claim 14, further comprising:
receiving a second cardiac electrical signal as a second unipolar signal via a second one of the anode and the cathode; and
determining the at least one feature by determining an activation time difference as a time interval between the first feature of the first cardiac electrical signal and a second feature of the second cardiac electrical signal; and
determine that the activation time difference meets the first bundle branch capture criteria.

16. The method of claim 11, further comprising receiving at least the first cardiac electrical signal by sensing a bipolar signal via the anode and the cathode.

17. The method of claim 16, further comprising:
delivering pacing pulses via the anode and the cathode at each of a plurality of pacing pulse outputs;
determining the at least one feature from the first cardiac electrical signal by:
determining, from the bipolar signal, a first QRS morphology corresponding to a first pacing pulse output of the plurality of pacing pulse outputs;
determining, from the bipolar signal, a second QRS morphology; and corresponding to a second pacing pulse output of the plurality of pacing pulse outputs, wherein the second pacing pulse output is greater than the first pacing pulse output and the second QRS morphology is different than the first QRS morphology;
detecting a change in the bipolar signal between the first QRS morphology and the second QRS morphology; and
determining that the at least one feature meets the first bundle branch capture criteria in response to detecting in the bipolar signal the change between the first QRS morphology and the second QRS morphology.

18. The method of claim 11, further comprising:
generating a unipolar pacing pulse delivered via the cathode;
generating a bipolar pacing pulse delivered via the cathode and the anode;
receiving at least the first cardiac electrical signal by:
receiving a first unipolar signal via the anode; and
receiving a second cardiac electrical signal as a second unipolar signal via the cathode;
determining, from the first unipolar signal and the second unipolar signal following the unipolar pacing pulse, a first activation time difference from a first fiducial point of the first unipolar signal to a second fiducial point of the second unipolar signal;
determining, from the first unipolar signal and the second unipolar signal following the bipolar pacing pulse, a second activation time difference from the first fiducial point of the first unipolar signal to the second fiducial point of the second unipolar signal;
determining that the second activation time difference is less than the first activation time difference; and
determining that the at least one feature meets the first bundle branch capture criteria in response to the second activation time difference being less than the first activation time difference.

19. The method of claim 18, further comprising:
delivering a bipolar pacing pulse via the anode and the cathode at each of a plurality of pacing pulse outputs;
determining a first lowest pacing pulse output of the plurality of pacing pulse outputs that is associated with anodal bundle branch capture being determined in response to the first bundle branch capture criteria being met;
determining a bipolar bilateral bundle branch pacing capture threshold as the first lowest pacing pulse output of the plurality of pacing pulse outputs;
setting the pacing pulse output based on the bipolar bundle branch pacing capture threshold; and
delivering bipolar bilateral bundle branch pacing by delivering bipolar pacing pulses at the pacing pulse output for capturing the first bundle branch via the anode and the second bundle branch via the cathode.

20. The method of claim 19, further comprising:
determining that the bipolar bilateral bundle branch capture threshold is greater than a maximum pacing output limit;
determining a second lowest pacing pulse output of the plurality of pacing pulse outputs that is associated with the second cardiac electrical signal meeting second bundle branch capture criteria;
setting the pacing pulse output based on the second lowest pacing pulse output that is associated with the second cardiac electrical signal meeting second bundle branch capture criteria; and
delivering single bundle branch pacing by delivering pacing pulses at the pacing pulse output for capturing the second bundle branch via the cathode.

21. A non-transitory computer readable medium storing instructions which, when executed by processing circuitry of a medical device system, cause the device system to:
receive at least a first cardiac electrical signal that is sensed during bilateral bundle branch pacing delivered from a bipolar electrode pair comprising an anode positioned along a first bundle branch and a cathode positioned along a second bundle branch opposite the first bundle branch;
determine at least one feature from the first cardiac electrical signal;
determine that the at least one feature meets first bundle branch capture criteria indicating that the bilateral bundle branch pacing has captured the first bundle branch;
determine anodal bundle branch capture in response to the first bundle branch capture criteria being met;
determine a pacing pulse output based on determining the anodal bundle branch capture; and
generate pacing pulses according to the determined pacing pulse output.

* * * * *